(12) United States Patent
Tsichlis

(10) Patent No.: US 6,660,906 B1
(45) Date of Patent: Dec. 9, 2003

(54) TPL2 TRANSGENIC KNOCKOUT MICE

(75) Inventor: Philip N. Tsichlis, Willow Grove, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/522,775

(22) Filed: Mar. 8, 2000

(51) Int. Cl.$^7$ .................... A01K 67/027; C12N 15/00; C12N 15/09; C12N 15/63; C12N 15/70

(52) U.S. Cl. .................... 800/18; 800/25; 435/325; 536/23.5

(58) Field of Search ................ 800/13, 14, 18, 800/25; 435/320.1, 455, 463, 325; 536/23.1, 23.5

(56) References Cited

FOREIGN PATENT DOCUMENTS

WO    WO 00/11191    3/2000

OTHER PUBLICATIONS

Moens et al; Defects in heart and lung development in compound heterozygotes for two different targeted mutations at the N–myc locus, 1993, Development, 119: 485–499.*
Moreadith et al; Gene targeting in embryonic stem cels: the new physiology and metabolism, 1997, J. Mol. Med. , 75:208–216.*
Mullins et al; Molecular Medlince in genetically engineered animals, 1996, J. Clin. Invest., 98: S37–S40.*
Seamark et al; Progress and emerging problems in livestock transgenesis: a summary perspective, 1994, Reprod. Fertil. Dev., 6: 653–657.*
Capecchi, M.R., Targeted gene replacement, Scientific American, 1994, pp. 52–59.
Enry et al., Involvement of the Tpl–2/cot oncogene in MMTV tumorigenesis, Oncogene, 1996, vol. 13, No. 9, pp. 2015–2020.
Makris et al., Structure of a Moloney Murine Leukemia Virus–virus–like 30 recombinant: implications for transduction of the c–Ha–ras proto–oncogene, Journal of Virology, 1993, vol. 67, No. 3, pp. 1286–1291.
Patriotis et al., Tumor progression locus 2 (*Tpl–2*) encodes a protein kinase involved in the progression of rodent T–cell lymphomas and in T–cell activation, Proc. Natl. Acad. Sci, USA. Mar. 1993, vol. 80, No. 6, pp. 2251–2555.
Sourvinos et al., Overexpression of the Tpl–2/Cot oncogene in human breast cancer, Oncogene, 1999, vol. 18, No. 35, pp. 4968–4973.
Grammatikakis et al. (1999) p50$^{cdc37}$ Acting in Concert with Hsp90 is Required for Raf–1 Function, Molecular and Cellular Biology, 19:1661–1672.
Lin et al. (1999) The Ankyrin Repeat–containing Adaptor Protein Tvl–1 is a Novel Substrate and Regulator of Raf–1, Journal of Biological Chemistry, 274:14706–14715.

Poyet et al. (2000) Activation of the IκB Kinases by RIP via IKKγ/NEMO–mediated, Journal of Biological Chemistry, 275:37966–37977.
Beutler, B.(1990) The complex regulation and biology of TNF (cachectin). Crit Rev. Oncog. 2, 9–18.
Ceci et al. (1997) Tpl–2 is an oncogenic kinase that is activated by carboxyterminal truncation. *Genes & Development* 11:688–700.
Hambleton et al. (1995) Activation of Raf–1 and mitogen–activated protein kinase in murine macrophages partially mimics lipopolysaccharide–induced signaling events. J Exp. Med 182, 147–154.
Han et al. (1990) The essential role of the UA–rich sequence in endotoxin–induced cachectin/TNF synthesis. Eur. Cytokine Netw. 1, 71–75.
Heller et al. (1992) The p70 tumor necrosis factor receptor mediates cytotoxicity. Cell 70:47–56.
Hsu et al. (1995) The TNF Receptor 1–Associated Protein TRADD Signals Cell Death and NF–kappa B Activation Cell 81:495–504.
Hsu et al. (1996) TRADD–TRAF2 and TRADD–FADD interactions define two distinct TNF receptor 1 signal transduction pathways. Cell 84:299–308.
Ichijo et al. (1997) Induction Of Apoptosis By Ask1, a Mammalian Mapkkk That Activates Sapk/Ink and P38 Signaling Pathways. Science 275:90–94.
Kontoylannis et al. (1999) Impaired On/Off Regulation of TNF Biosynthesis in Mice Lacking TNF AU–Rich Elements: Implications for Joint and Gut–Associated Immunopathologies, Immunity 10:387–398.
Kotlyarov et al. (1999) MAPKAP kinase 2 is essential for LPS–induced TNF–alpha biosynthesis. Nat. Cell Biol. 1, 94–97.
Lee et al. (1994) A protein kinase involved in the regulation of inflammatory cytokine biosynthesis. Nature 372:739–746.
Malinin et al. (1997) MAP3K–Related Kinase Involved in NF–kappa–B Induction by TNF, CD95 and IL–1. Nature 385:540–544.
Marino et al. (1997) Characterization of tumor necrosis factor–deficient mice. Proc. Natl. Acad. Sci. U. S. A 94, 8093–8098.

(List continued on next page.)

*Primary Examiner*—Peter Paras
(74) *Attorney, Agent, or Firm*—Nanda P.B.A. Kumar; William J. McNichol, Jr.; Reed Smith LLP.

(57) ABSTRACT

The present invention is directed to animal having functionally disrupted endogenous Tpl2. These animals are resistant to Lps induced endotoxin shock and TNFα-mentioned inflammatory disease. A method of identifying Tpl2 specific inhibitors of endotoxin shock or antagonists to inflammation on and a method of treating or preventing TNFα-mediated inflammatory diseases and Lps induced endotoxin shock in animals are also within the scope of this invention. The present invention is also directed to Tpl2 encoding nucleic acid molecules (SEQ ID NOS: 1 and 3) and polypeptides (SEQ ID NOS: 2 and 4) encoded by such molecules.

8 Claims, 19 Drawing Sheets

OTHER PUBLICATIONS

Pasparakis et al. (1996). Immune and inflammatory responses in TNF alpha–deficient mice: a critical requirement for TNF alpha in the formation of primary B cell follicles, follicular dendritic cell networks and germinal centers, and in the maturation of the humoral immune response. J. Exp. Med 184, 1397–1411.

Patriotis et al. (1994) Tpl–2 acts in concert with Ras and Raf–1 to activate mitogen–activated protein kinase. Proc. Natl. Acad. Sci. U. S. A. 91, 9755–9759.

Pfeffer et al. (1993) Mice deficient for the 55 kd tumor necrosis factor receptor are resistant to endotoxic shock, yet succumb to L. monocytogenes infection. Cell 73, 457–467.

Prichett et al. (1995) Mechanism of action of bicyclic imidazoles defines a translational regulatory pathway for tumor necrosis factor alpha. J Inflamm. 45, 97–105.

Raabe et al. (1998) Relative contribution of transcription and translation to the induction of tumor necrosis factor–alpha by lipopolysaccharide. J Biol.Chem. 273, 974–980.

Rothe et al. (1993) Mice lacking the tumor necrosis factor receptor 1 are resistant to TNF– mediated toxicity by highly susceptible to infection by Listeria monocytogenes. Nature 364, 798–802.

Salmeron et al. (1996) Activation of MEK–1 and SEK–1 by Tpl–2 proto–oncoprotein, a novel MAP kinase kinase kinase. EMBO J 15, 817–826.

Sha et al. (1995) Targeted disruption of the p50 subunit of NF–kappa B leads to multifocal defects in immune responses. Cell 80, 321–330.

Srinivasula et al. (1999) CLAP, a novel caspase recruitment domain–containing protein in the tumor necrosis factor receptor pathway, regulates NF–kappa B activation and apoptos. J Biol. Chem. 274, 17946–17954.

Swantek, et al. (1997) Jun N–terminal kinase/stress–activated protein kinanse (JNK/SAPK) is required for lipopolysaccharide stimulation of tumor necrosis factor alpha (TNF–alpha) translation glucocorticoids inhibit TNF–alpha translation by blocking JNL/SAPK. Mol. Cell Biol. 17, 6274–6282.

Tartaglia et al. (1993) Stimulation of human T–cell proliferation by specific activation of the 75–kDa tumor necrosis factor receptor. Journal of Immunology 151:4637–41.

Tsatsanis et al. (1998a) Tpl–2 induces IL–2 expression in T–cell lines by triggering multiple signaling pathways that activate NFAT and NF–kappaB. Oncogene. 17, 2609–2618.

Tsatsanis et al. (1998b) The Tpl–2 protooncoprotein activates the nuclear factor of activated T cells and induces interleukin 2 expression in T cell lines. Proc. Natl. Acad. Sci. U. S. A. 95, 3827–3832.

* cited by examiner

A

B

A1

A2

B

C

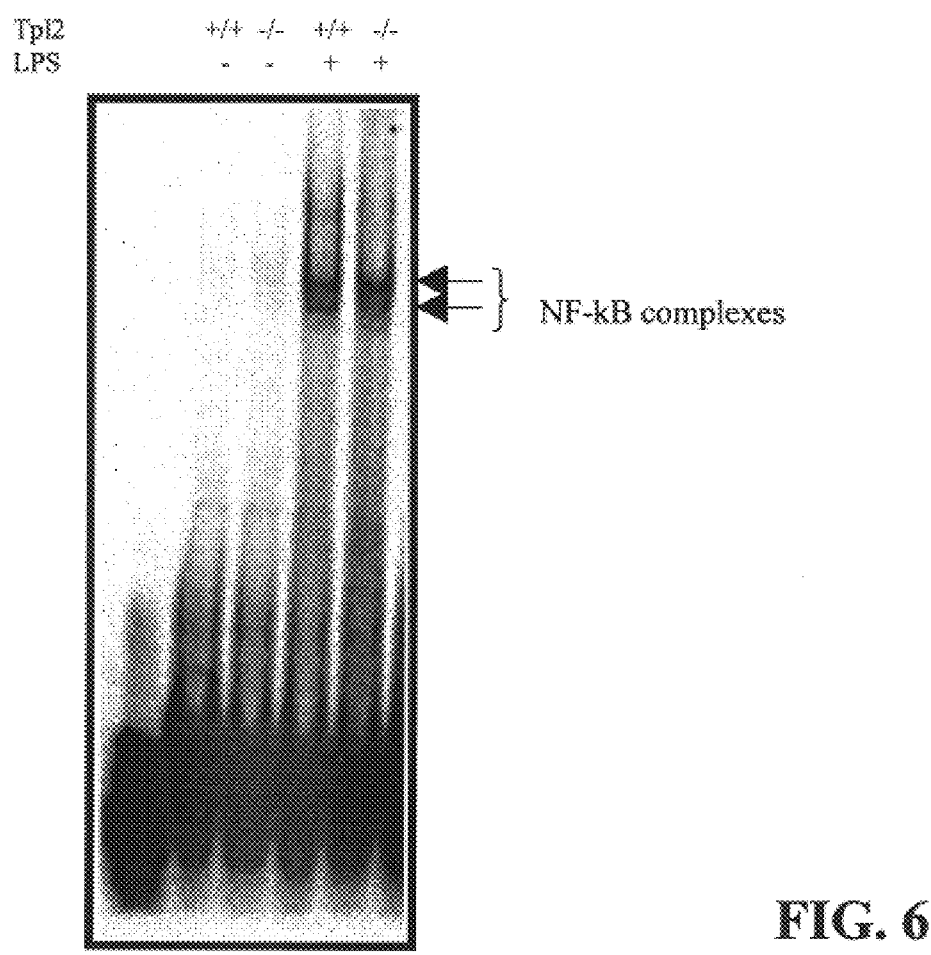
FIG. 6
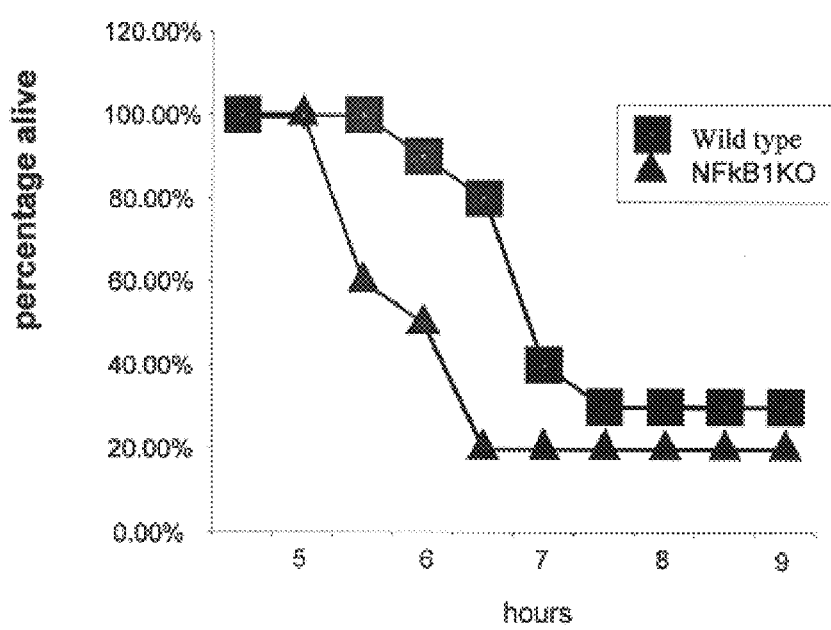

| | | | | |
|---|---|---|---|---|
| 1 | CACTATAGGG | CGAATTGGGC | CCTCTAGATG | CATGCTCGAG | CGGCCGCCAG |
| 51 | TGTGATGGAT | ATCTGCAGAA | TTCGCCCTT | | |
| 52 | | | | | |
| 53 | CGCGAAGAAGC | CAGGGGAATA | | | |
| 101 | GGTAGCCACA | TCTTGTTTGC | AGATAAGAAA | GGAAGCTAAC | GCAGTATCTG |
| 151 | CAAAGCCAGG | AGTCTGACTC | AGTACTTTTC | TCACTCATGC | ATACAAAGCA |
| 201 | GCTAAAAATG | ACACAGCTTA | TTTACCATGC | CCCTGACACT | GCACTGAGCA |
| 251 | CTTTATGAGC | TTGAACTCTG | TTAATCCTCA | CGACCACCTC | ATGAGACTCT |
| 301 | CCAGAAAGAG | CAACAGTAAT | GGAGTACATG | AGCACTGGAA | GTGACAATAA |
| 351 | AGAAGAGATT | GATTTATTAA | TTAAACATTT | AAATGTGTCT | GATGTAATAG |
| 401 | ACATTATGGA | AAATCTTTAT | GCAAGTGAAG | AGCCAGCAGT | TTATGAACCC |
| 451 | AGTCTAATGA | CCATGTGTCA | AGACAGTAAT | CAAAACGATG | AGCGTTCTAA |
| 501 | GTCTCTGCTG | CTTAGTGGCC | AAGAGGTACC | ATGGTTGTCA | TCAGTCAGAT |
| 551 | ACGGAACTGT | GGAGGATTTG | CTTGCTTTTG | CAAACCATAT | ATCCAACACT |
| 601 | GCAAAGCATT | TTTATGGACA | ACGACCACAG | GAATCTGGAA | TTTTATTAAA |
| 651 | CATGGTCATC | ACTCCCCAAA | ATGGACGTTA | CCAAATAGAT | TCCGATGTTC |
| 701 | TCCTGATCCC | CTGGAAGCTG | ACTTACAGGA | ATATTGGTTC | TGATTTTATT |
| 751 | CCTCGGGGCG | CCTTTGGAAA | GGTATACTTG | GCACAAGATA | TAAAGACGAA |
| 801 | GAAAAGAATG | GCGTGTAAAC | TGATCCCAGT | AGATCAATTT | AAGCCATCTG |
| 851 | ATGTGGAAAT | CCAGGCTTGC | TTCCGGCACG | AGAACATCGC | AGAGCTGTAT |
| 901 | GGCGCAGTCC | TGTGGGGTGA | AACTGTCCAT | CTCTTTATGG | AAGCAGGCGA |
| 951 | GGGAGGGTCT | GTTCTGGAGA | AACTGGAGAG | CTGTGGACCA | ATGAGAGAAT |
| 1001 | TTGAAATTAT | TTGGGTGACA | AAGCATGTTC | TCAAGGGACT | TGATTTTCTA |
| 1051 | CACTCAAAGA | AAGTGATCCA | TCATGATATT | AAACCTAGCA | ACATTGTTTT |
| 1101 | CATGTCCACA | AAAGCTGTTT | TGGTGGATTT | TGGCCTAAGT | GTTCAAATGA |
| 1151 | CCGAAGATGT | CTATTTTCCT | AAGGACCTCC | GAGGAACAGA | GATTTACATG |
| 1201 | AGCCCAGAGG | TCATCCTGTG | CAGGGGCCAT | TCAACCAAAG | CAGACATCTA |
| 1251 | CAGCCTGGGG | GCCACGCTCA | TCCACATGCA | GACGGGCACC | CCACCCTGGG |
| 1301 | TGAAGCGCTA | CCCTCGCTCA | GCCTATCCCT | CCTACCTGTA | CATAATCCAC |
| 1351 | AAGCAAGCAC | CTCCACTGGA | AGACATTGCA | GATGACTGCA | GTCCAGGGAT |
| 1401 | GAGAGAGCTG | ATAGAAGCTT | CCCTGGAGAG | AAACCCCAAT | CACCGCCCAA |
| 1451 | GAGCCGCAGA | CCTACTAAAA | CATGAGGCCC | TGAACCCGCC | CAGAGAGGAT |
| 1501 | CAGCCACGCT | GTCAGAGTCT | GGACTCTGCC | CTCTTGGAGC | GCAAGAGGCT |
| 1551 | GCTGAGTAGG | AAGGAGCTGG | AACTTCCTGA | GAACATTGCT | GATTCTTCGT |
| 1601 | GCACAGGAAG | CACCGAGGAA | TCTGAGATGC | TCAAGAGGCA | ACGCTCTCTC |
| 1651 | TACATCGACC | TCGGCGCTCT | GGCTGGCTAC | TTCAATCTTG | TTCGGGGACC |
| 1701 | ACCAACGCTT | GAATATGGCT | GAAGGATGCC | ATGTTTGCTC | TAAATTAAGA |
| 1751 | CAGCATTGAT | CTCCTGGAGG | CTGGTTCT | | |
| 1752 | | | | | |
| 1753 | AA GGGCGAATTC | CAGCACACTG | | | |
| 1801 | GCGGCCGTTA | CTAGTGGATC | CGAGCTCGGT | ACCAAGCTTG | ATGCATAGCT |
| 1851 | TGAGTATTCT | ATAGTGTCAC | CTAAATAGCT | TGGCGTAATC | ATGGTCATAG |
| 1901 | CTGTTTCCTG | TGTGAAATTG | TTATCCGCTC | ACAATTCCAC | ACAACATACG |
| 1951 | AGCCGGAAGC | ATAAAGTGTA | AAGCCTGGGG | TGCCTAATGA | GTGAGCTAAC |
| 2001 | T | | | | |

FIG. 16

```
  1 MEYMSTGSDN KEEIDLLIKH LNVSDVIDIM ENLYASEEPA VYEPSLMTMC QDSNQNDERS
 61 KSLLLSGQEV PWLSSVRYGT VEDLLAFANH ISNTAKHFYG QRPQESGILL NMVITPQNGR
121 YQIDSDVLLI PWKLTYRNIG SDFIPRGAFG KVYLAQDIKT KKRMACKLIP VDQFKPSDVE
181 IQACFRHENI AELYGAVLWG ETVHLFMEAG EGGSVLEKLE SCGPMREFEI IWVTKHVLKG
241 LDFLHSKKVI HHDIKPSNIV FMSTKAVLVD FGLSVQMTED VYFPKDLRGT EIYMSPEVIL
301 CRGHSTKADI YSLGATLIHM QTGTPPWVKR YPRSAYPSYL YIIHKQAPPL EDIADDCSPG
361 MRELIEASLE RNPNHRPRAA DLLKHEALNP PREDQPRCQS LDSALLERKR LLSRKELELP
421 ENIADSSCTG STEESEMLKR QRSLYIDLGA LAGYFNLVRG PPTLEYG*
```

FIG. 17

```
   1    ggaatttccc atcgcggggg ctcgggtgtt ctgggccagc cggcaggccc tttctgttta
  61    cggagagaaa ggggaaatgg aaaaggcggg gaggacgctg gcgtcggcta cgccgccccg
 121    gggccagttc agacgccgag agtccggggc tgcagcgtac cgctcctccc gctgcggatc
 181    gcccggcctt tggtcggccg ccgtcgtcc ggacgcccgt acgtctggct cccgctggca
 241    agccacccgc tgcccaccaa gcccgagctc cgggcgggca cacggaacac tcagactccc
 301    cagcaggcac cacagtg 318    atggagtaca tgagcaccgg aagcgacgag aaagaagaga ttg
 361    atttattaat taaccattta aacgtgtcgg aagtcctgga catcatggag aacctttatg
 421    caagtgaaga gcctgcagtg tatgagccca gtctgatgac catgtgtcca gacagcaatc
 481    aaaacaagga acattcagag tcgctgcttc ggagtggcca ggaggtgccc tggttgtcgt
 541    ctgtcagata tgggactgtg gaggatctgc ttgcatttgc aaaccatatc tcgaatacga
 601    caaagcattt ttacggatgt cggccccaag aatctgggat tttattaaat atggtaatca
 661    gtccccagaa tggtcgctac caaatcgact cggatgttct ccttgtcccg tggaagctga
 721    cgtacaggag cattggttct ggtttcgttc ctcgggggc cttggaaaa gtgtacttag
 781    cacaagacat gaagacaaag aaaagaatgg catgtaaact gatccctgta gatcagttta
 841    agccatcaga tgtggaaatc caggcctgct tccggcacga aacattgcc gagttatacg
 901    gtgcggtcct atggggcgac actgtccatc tcttcatgga agccggcgag ggagggtctg
 961    tcctggagaa gctggagagc tgtgggccca tgagagaatt tgaaattatc tgggtgacaa
1021    agcacgttct caagggactt gattttctgc actccaagaa agtcatccac cacgatatca
1081    aacctagcaa cattgtattc atgtctacga aagctgtgtt ggtagatttt ggcctgagtg
1141    ttcaaatgac agaagatgtc tatctcccca aggacctccg gggaacagag atctacatga
1201    gcctgaggt gattctgtgc aggggccatt ccacaaaagc agacatctac agccttggag
1261    ccacgctcat tcacatgcag acaggcaccc caccctgggt gaagcgctac cctcgatcgg
1321    cctatccctc ctacctgtac ataatccaca gcaggcacc tcccctggaa gatattgctg
1381    gtgactgcag tccaggcatg agggagctga tagaagccgc cctggagagg aaccccaacc
1441    accgcccaaa agcagcagac tactgaaac acgaagccct gaatccccca agagaggacc
1501    agccacggtg tcagagtctg gactctgccc tctttgaccg gaagaggctg ctgagcagga
1561    aggagctaga acttcctgag aacattgctg attcatcatg cacaggaagc accgaggagt
1621    ctgaagtgct caggagacag cgttccctct acattgatct cggagctctg gctggctact
1681    tcaatattgt tcgtggtcca ccaaccctgg aatatggctg a 1722           tggatgact ctattggcaa
1741    cagtagggcg gatatttctc tcctggatgt tggtttcaca gatcctacac agcagctctg
1801    gatagtgaat tttacccaat tttttttagga agcagggagg aggtctctag tgacacaaga
1861    atgtcaaagc cctggccccc tttgtgaagc tcctctggca tgttccagag cccaaggttc
1921    tcatttctca ggtggtggga ctggacaaaa gggagtggtg agctcaggaa agaatcattt
1981    ctgatgacaa ttctattcac tttgcacttt aatggacatt aaaaaatagc tctcacaaga
2041    tagtaaccta aaatacctgt ttttggttct tatataacca tgggttcttc attcaactca
2101    gaagacctga tctgtgtata tatttgtgtg tattatatgg taactctttg taccttggtt
2161    ggtagagtct agtataagtt tagttaatag tattttgggt ggatagaaca actctaatat
2221    tacagcaatt cactggacta gtgtctcaca aatgactgat ttactcagag ccattaagca
2281    gcaggccact agtgagagtt tctgttatgt tcctatggaa acactgtgta ttgtacgtgc
2341    tatgcttaaa acatttaaaa cacaatgttt taaatgtgga cagaactgtg taaaccacat
2401    aatttctgta catcccaaag gatgagaaat gtgaccttca agaaatgga aacatttgta
2461    aattctttgt agtgatacct ttgtaattaa tgaaactatt tttctttaaa gtgtttctat
2521    attaaaaata gcatactgtg tatgtttat tccaaaattc cttcatgaat cttcatata
2581    tatgtgta tatttttaa cattgtaaag tatgagtatt cttatttaaa gtatattttt
2641    acattatgca aatgaacttc aacgttttag tccaatgtga ctggtcaaat aaaccaaata
2701    aactgagtat tttgtcttaa
```

FIG. 18

```
  1 MEYMSTGSDE KEEIDLLINH LNVSEVLDIM ENLYASEEPA VYEPSLMTMC PDSNQNKEHS
 61 ESLLRSGQEV PWLSSVRYGT VEDLLAFANH ISNTTKHFYG CRPQESGILL NMVISPQNGR
121 YQIDSDVLLV PWKLTYRSIG SGFVPRGAFG KVYLAQDMKT KKRMACKLIP VDQFKPSDVE
181 IQACFRHENI AELYGAVLWG DTVHLFMEAG EGGSVLEKLE SCGPMREFEI IWVTKHVLKG
241 LDFLHSKKVI HHDIKPSNIV FMSTKAVLVD FGLSVQMTED VYLPKDLRGT EIYMSPEVIL
301 CRGHSTKADI YSLGATLIHM QTGTPPWVKR YPRSAYPSYL YIIHKQAPPL EDIAGDCSPG
361 MRELIEAALE RNPNHRPKAA DLLKHEALNP PREDQPRCQS LDSALFDRKR LLSRKELELP
421 ENIADSSCTG STEESEVLRR QRSLYIDLGA LAGYFNIVRG PPTLEYG
```

FIG. 19

SEQUENCE LISTING

```
<160> NUMBER OF SEQ ID NOS: 13

<210> SEQ ID NO 1
<211> LENGTH: 1699
<212> TYPE: DNA
<213> ORGANISM: Human Tpl2 polynucleotide

<400> SEQUENCE: 1
```

-continued

```
cgcgaagaag ccaggggaat aggtagccac atcttgtttg cagataagaa aggaagctaa      60
cgcagtatct gcaaagccag gagtctgact cagtactttt ctcactcatg catacaaagc     120
agctaaaaat gacacagctt atttaccatg cccctgacac tgcactgagc actttatgag     180
cttgaactct gttaatcctc acgaccacct catgagactc tccagaaaga gcaacagtaa     240
tggagtacat gagcactgga agtgacaata agaagagat tgatttatta attaaacatt      300
taaatgtgtc tgatgtaata gacattatgg aaaatcttta tgcaagtgaa gagccagcag     360
tttatgaacc cagtctaatg accatgtgtc aagacagtaa tcaaaacgat gagcgttcta     420
agtctctgct gcttagtggc caagaggtac catggttgtc atcagtcaga tacggaactg     480
tggaggattt gcttgctttt gcaaaccata tatccaacac tgcaaagcat ttttatggac     540
aacgaccaca ggaatctgga attttattaa acatggtcat cactccccaa aatggacgtt     600
accaaataga ttccgatgtt ctcctgatcc cctggaagct gacttacagg aatattggtt     660
ctgattttat tcctcggggc gcctttggaa aggtatactt ggcacaagat ataaagacga     720
agaaaagaat ggcgtgtaaa ctgatcccag tagatcaatt taagccatct gatgtggaaa     780
tccaggcttg cttccggcac gagaacatcg cagagctgta tggcgcagtc ctgtggggtg     840
aaactgtcca tctcttatg gaagcaggcg agggagggtc tgttctggag aaactggaga      900
gctgtggacc aatgagagaa tttgaaatta tttgggtgac aaagcatgtt ctcaagggac     960
ttgatttct acactcaaag aaagtgatcc atcatgatat taaacctagc aacattgttt     1020
tcatgtccac aaaagctgtt ttggtggatt ttggcctaag tgttcaaatg accgaagatg     1080
tctattttcc taaggacctc cgaggaacag agatttacat gagcccagag gtcatcctgt     1140
gcagggccca ttcaaccaaa gcagacatct acagcctggg ggccacgctc atccacatgc     1200
agacgggcac cccaccctgg gtgaagcgct accctcgctc agcctatccc tcctacctgt     1260
acataatcca aagcaagca cctccactgg aagacattgc agatgactgc agtccaggga     1320
tgagagagct gatagaagct tccctggaga gaaaccccaa tcaccgccca agagccgcag     1380
acctactaaa acatgaggcc ctgaacccgc ccagagagga tcagccacgc tgtcagagtc     1440
tggactctgc cctcttggag cgcaagaggc tgctgagtag gaaggagctg gaacttcctg     1500
agaacattgc tgattcttcg tgcacaggaa gcaccgagga atctgagatg ctcaagaggc     1560
aacgctctct ctacatcgac ctcggcgctc tggctggcta cttcaatctt gttcggggac     1620
caccaacgct tgaatatggc tgaaggatgc catgtttgct ctaaattaag acagcattga     1680
tctcctggag gctggttct                                                  1699
```

<210> SEQ ID NO 2
<211> LENGTH: 467
<212> TYPE: PRT
<213> ORGANISM: Artificial Sequence
<220> FEATURE:
<223> OTHER INFORMATION: Human Tpl2 polypeptide sequence

<400> SEQUENCE: 2

Met Glu Tyr Met Ser Thr Gly Ser Asp Asn Lys Glu Glu Ile Asp Leu
1               5                   10                  15

Leu Ile Lys His Leu Asn Val Ser Asp Val Ile Asp Ile Met Glu Asn
                20                  25                  30

Leu Tyr Ala Ser Glu Glu Pro Ala Val Tyr Glu Pro Ser Leu Met Thr
            35                  40                  45

Met Cys Gln Asp Ser Asn Gln Asn Asp Glu Arg Ser Lys Ser Leu Leu

```
              50                  55                  60
Leu Ser Gly Gln Glu Val Pro Trp Leu Ser Ser Val Arg Tyr Gly Thr
 65                  70                  75                  80

Val Glu Asp Leu Leu Ala Phe Ala Asn His Ile Ser Asn Thr Ala Lys
                 85                  90                  95

His Phe Tyr Gly Gln Arg Pro Gln Glu Ser Gly Ile Leu Leu Asn Met
                100                 105                 110

Val Ile Thr Pro Gln Asn Gly Arg Tyr Gln Ile Asp Ser Asp Val Leu
            115                 120                 125

Leu Ile Pro Trp Lys Leu Thr Tyr Arg Asn Ile Gly Ser Asp Phe Ile
130                 135                 140

Pro Arg Gly Ala Phe Gly Lys Val Tyr Leu Ala Gln Asp Ile Lys Thr
145                 150                 155                 160

Lys Lys Arg Met Ala Cys Lys Leu Ile Pro Val Asp Gln Phe Lys Pro
                165                 170                 175

Ser Asp Val Glu Ile Gln Ala Cys Phe Arg His Glu Asn Ile Ala Glu
                180                 185                 190

Leu Tyr Gly Ala Val Leu Trp Gly Glu Thr Val His Leu Phe Met Glu
                195                 200                 205

Ala Gly Glu Gly Gly Ser Val Leu Glu Lys Leu Glu Ser Cys Gly Pro
210                 215                 220

Met Arg Glu Phe Glu Ile Ile Trp Val Thr Lys His Val Leu Lys Gly
225                 230                 235                 240

Leu Asp Phe Leu His Ser Lys Lys Val Ile His His Asp Ile Lys Pro
                245                 250                 255

Ser Asn Ile Val Phe Met Ser Thr Lys Ala Val Leu Val Asp Phe Gly
                260                 265                 270

Leu Ser Val Gln Met Thr Glu Asp Val Tyr Phe Pro Lys Asp Leu Arg
                275                 280                 285

Gly Thr Glu Ile Tyr Met Ser Pro Glu Val Ile Leu Cys Arg Gly His
                290                 295                 300

Ser Thr Lys Ala Asp Ile Tyr Ser Leu Gly Ala Thr Leu Ile His Met
305                 310                 315                 320

Gln Thr Gly Thr Pro Pro Trp Val Lys Arg Tyr Pro Arg Ser Ala Tyr
                325                 330                 335

Pro Ser Tyr Leu Tyr Ile Ile His Lys Gln Ala Pro Pro Leu Glu Asp
                340                 345                 350

Ile Ala Asp Asp Cys Ser Pro Gly Met Arg Glu Leu Ile Glu Ala Ser
                355                 360                 365

Leu Glu Arg Asn Pro Asn His Arg Pro Arg Ala Ala Asp Leu Leu Lys
                370                 375                 380

His Glu Ala Leu Asn Pro Pro Arg Glu Asp Gln Pro Arg Cys Gln Ser
385                 390                 395                 400

Leu Asp Ser Ala Leu Leu Glu Arg Lys Arg Leu Leu Ser Arg Lys Glu
                405                 410                 415

Leu Glu Leu Pro Glu Asn Ile Ala Asp Ser Ser Cys Thr Gly Ser Thr
                420                 425                 430

Glu Glu Ser Glu Met Leu Lys Arg Gln Arg Ser Leu Tyr Ile Asp Leu
                435                 440                 445

Gly Ala Leu Ala Gly Tyr Phe Asn Leu Val Arg Gly Pro Pro Thr Leu
                450                 455                 460

Glu Tyr Gly
465
```

<210> SEQ ID NO 3
<211> LENGTH: 2720
<212> TYPE: DNA
<213> ORGANISM: Rat Tpl2 polynucleotide sequence

<400> SEQUENCE: 3

| | | | | | | |
|---|---|---|---|---|---|---|
| ggaatttccc | atcgcggggg | ctcggtgtt | ctgggccagc | cggcaggccc | tttctgttta | 60 |
| cggagagaaa | ggggaaatgg | aaaaggcggg | gaggacgctg | gcgtcggcta | cgccgccccg | 120 |
| gggccagttc | agacgccgag | agtccggggc | tgcagcgtac | cgctcctccc | gctgcggatc | 180 |
| gcccggcctt | tggtcggccg | ccggtcgtcc | ggacgcccgt | acgtctggct | cccgctggca | 240 |
| agccacccgc | tgcccaccaa | gcccgagctc | cgggcgggca | cacggaacac | tcagactccc | 300 |
| cagcaggcac | acagtgatg | gagtacatga | gcaccggaag | cgacgagaaa | gaagagattg | 360 |
| atttattaat | taaccattta | aacgtgtcgg | aagtcctgga | catcatggag | aacctttatg | 420 |
| caagtgaaga | gcctgcagtg | tatgagccca | gtctgatgac | catgtgtcca | gacagcaatc | 480 |
| aaaacaagga | acattcagag | tcgctgcttc | ggagtggcca | ggaggtgccc | tggttgtcgt | 540 |
| ctgtcagata | tgggactgtg | gaggatctgc | ttgcatttgc | aaaccatatc | tcgaatacga | 600 |
| caaagcattt | ttacggatgt | cggccccaag | aatctgggat | tttattaaat | atggtaatca | 660 |
| gtccccagaa | tggtcgctac | caaatcgact | cggatgttct | ccttgtcccg | tggaagctga | 720 |
| cgtacaggag | cattggttct | ggtttcgttc | tcgggggggc | ctttggaaaa | gtgtacttag | 780 |
| cacaagacat | gaagacaaag | aaaagaatgg | catgtaaact | gatccctgta | gatcagttta | 840 |
| agccatcaga | tgtggaaatc | caggcctgct | tccggcacga | gaacattgcc | gagttatacg | 900 |
| gtgcggtcct | atgggcgac | actgtccatc | tcttcatgga | agccggcgag | ggagggtctg | 960 |
| tcctggagaa | gctggagagc | tgtgggccca | tgagagaatt | tgaaattatc | tgggtgacaa | 1020 |
| agcacgttct | caagggactt | gattttctgc | actccaagaa | agtcatccac | cacgatatca | 1080 |
| aacctagcaa | cattgtattc | atgtctacga | agctgtgtt | ggtagatttt | ggcctgagtg | 1140 |
| ttcaaatgac | agaagatgtc | tatctccca | aggacctccg | gggaacagag | atctacatga | 1200 |
| gccctgaggt | gattctgtgc | aggggccatt | ccacaaaagc | agacatctac | agccttggag | 1260 |
| ccacgctcat | tcacatgcag | acaggcaccc | caccctgggt | gaagcgctac | cctcgatcgg | 1320 |
| cctatccctc | ctacctgtac | ataatccaca | gcaggcacc | tccctggaa | gatattgctg | 1380 |
| gtgactgcag | tccaggcatg | agggagctga | tagaagccgc | cctggagagg | aaccccaacc | 1440 |
| accgcccaaa | agcagcagac | ctactgaaac | acgaagccct | gaatccccca | agagaggacc | 1500 |
| agccacggtg | tcagagtctg | gactctgccc | tctttgaccg | gaagaggctg | ctgagcagga | 1560 |
| aggagctaga | acttcctgag | aacattgctg | attcatcatg | cacaggaagc | accgaggagt | 1620 |
| ctgaagtgct | caggagacag | cgttccctct | acattgatct | cggagctctg | gctggctact | 1680 |
| tcaatattgt | tcgtggtcca | ccaaccctgg | aatatggctg | atggatgact | ctattggcaa | 1740 |
| cagtagggcg | gatatttctc | tcctggatgt | tggtttcaca | gatcctacac | agcagctctg | 1800 |
| gatagtgaat | tttacccaat | ttttttagga | agcagggagg | aggtctctag | tgacacaaga | 1860 |
| atgtcaaagc | cctggccccc | tttgtgaagc | tcctctggca | tgttccagag | cccaaggttc | 1920 |
| tcatttctca | ggtggtggga | ctggacaaaa | gggagtggtg | agctcaggaa | agaatcattt | 1980 |
| ctgatgacaa | ttctattcac | tttgcacttt | aatggacatt | aaaaaatagc | tctcacaaga | 2040 |
| tagtaaccta | aaatacctgt | ttttggttct | tatataacca | tgggttcttc | attcaactca | 2100 |

```
gaagacctga tctgtgtata tatttgtgtg tattatatgg taactctttg taccttggtt   2160
ggtagagtct agtataagtt tagttaatag tattttgggt ggatagaaca actctaatat   2220
tacagcaatt cactggacta gtgtctcaca aatgactgat ttactcagag ccattaagca   2280
gcaggccact agtgagagtt tctgttatgt tcctatggaa acactgtgta ttgtacgtgc   2340
tatgcttaaa acatttaaaa cacaatgttt taaatgtgga cagaactgtg taaaccacat   2400
aatttctgta catcccaaag gatgagaaat gtgaccttca agaaatggaa acatttgta   2460 aattctttgt agtgataccT ttgtaattaa tgaaactatt tttctttaaa gtgtttctat   2520
attaaaaata gcatactgtg tatgttttat tccaaaattc cttcatgaat ctttcatata   2580
tatatgtgta tatattttaa cattgtaaag tatgagtatt cttatttaaa gtatatttt    2640 acattatgca aatgaacttc aacgttttag tccaatgtga ctggtcaaat aaaccaaata   2700
aactgagtat tttgtcttaa                                               2720
```

<210> SEQ ID NO 4
<211> LENGTH: 467
<212> TYPE: PRT
<213> ORGANISM: Artificial Sequence
<220> FEATURE:
<223> OTHER INFORMATION: Rat Tpl2 polypeptide sequence

<400> SEQUENCE: 4

```
Met Glu Tyr Met Ser Thr Gly Ser Asp Glu Lys Glu Glu Ile Asp Leu
 1               5                  10                  15

Leu Ile Asn His Leu Asn Val Ser Glu Val Leu Asp Ile Met Glu Asn
                20                  25                  30

Leu Tyr Ala Ser Glu Glu Pro Ala Val Tyr Glu Pro Ser Leu Met Thr
            35                  40                  45

Met Cys Pro Asp Ser Asn Gln Asn Lys Glu His Ser Glu Ser Leu Leu
        50                  55                  60

Arg Ser Gly Gln Glu Val Pro Trp Leu Ser Ser Val Arg Tyr Gly Thr
65                  70                  75                  80

Val Glu Asp Leu Leu Ala Phe Ala Asn His Ile Ser Asn Thr Thr Lys
                85                  90                  95

His Phe Tyr Gly Cys Arg Pro Gln Glu Ser Gly Ile Leu Leu Asn Met
            100                 105                 110

Val Ile Ser Pro Gln Asn Gly Arg Tyr Gln Ile Asp Ser Asp Val Leu
        115                 120                 125

Leu Val Pro Trp Lys Leu Thr Tyr Arg Ser Ile Gly Ser Gly Phe Val
    130                 135                 140

Pro Arg Gly Ala Phe Gly Lys Val Tyr Leu Ala Gln Asp Met Lys Thr
145                 150                 155                 160

Lys Lys Arg Met Ala Cys Lys Leu Ile Pro Val Asp Gln Phe Lys Pro
                165                 170                 175

Ser Asp Val Glu Ile Gln Ala Cys Phe Arg His Glu Asn Ile Ala Glu
            180                 185                 190

Leu Tyr Gly Ala Val Leu Trp Gly Asp Thr Val His Leu Phe Met Glu
        195                 200                 205

Ala Gly Glu Gly Gly Ser Val Leu Glu Lys Leu Glu Ser Cys Gly Pro
    210                 215                 220

Met Arg Glu Phe Glu Ile Ile Trp Val Thr Lys His Val Leu Lys Gly
225                 230                 235                 240

Leu Asp Phe Leu His Ser Lys Lys Val Ile His His Asp Ile Lys Pro
                245                 250                 255
```

-continued

```
Ser Asn Ile Val Phe Met Ser Thr Lys Ala Val Leu Val Asp Phe Gly
                260                 265                 270
Leu Ser Val Gln Met Thr Glu Asp Val Tyr Leu Pro Lys Asp Leu Arg
            275                 280                 285
Gly Thr Glu Ile Tyr Met Ser Pro Glu Val Ile Leu Cys Arg Gly His
        290                 295                 300
Ser Thr Lys Ala Asp Ile Tyr Ser Leu Gly Ala Thr Leu Ile His Met
305                 310                 315                 320
Gln Thr Gly Thr Pro Pro Trp Val Lys Arg Tyr Pro Arg Ser Ala Tyr
                325                 330                 335
Pro Ser Tyr Leu Tyr Ile Ile His Lys Gln Ala Pro Pro Leu Glu Asp
            340                 345                 350
Ile Ala Gly Asp Cys Ser Pro Gly Met Arg Glu Leu Ile Glu Ala Ala
        355                 360                 365
Leu Glu Arg Asn Pro Asn His Arg Pro Lys Ala Ala Asp Leu Leu Lys
    370                 375                 380
His Glu Ala Leu Asn Pro Pro Arg Glu Asp Gln Pro Arg Cys Gln Ser
385                 390                 395                 400
Leu Asp Ser Ala Leu Phe Asp Arg Lys Arg Leu Leu Ser Arg Lys Glu
                405                 410                 415
Leu Glu Leu Pro Glu Asn Ile Ala Asp Ser Ser Cys Thr Gly Ser Thr
            420                 425                 430
Glu Glu Ser Glu Val Leu Arg Arg Gln Arg Ser Leu Tyr Ile Asp Leu
        435                 440                 445
Gly Ala Leu Ala Gly Tyr Phe Asn Ile Val Arg Gly Pro Pro Thr Leu
    450                 455                 460
Glu Tyr Gly
465
```

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gcccagaccc tcacactcag     20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
aacacccatt cccttcacag     20

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gtgggccgct ctaggcacca a     21

```
<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
ctctttgatg tcacgcacga tttc                                              24

<210> SEQ ID NO 9
<211> LENGTH: 32
<212> TYPE: DNA
<213> ORGANISM: Artificial Sequence
<220> FEATURE:
<223> OTHER INFORMATION: Probe

<400> SEQUENCE: 9
acaagggact ttccgctggg gactttccag gg                                     32

<210> SEQ ID NO 10
<211> LENGTH: 17
<212> TYPE: DNA
<213> ORGANISM: Artificial Sequence
<220> FEATURE:
<223> OTHER INFORMATION: Probe

<400> SEQUENCE: 10
ccctggaaag tccccag                                                      17

<210> SEQ ID NO 11
<211> LENGTH: 32
<212> TYPE: DNA
<213> ORGANISM: Artificial Sequence
<220> FEATURE:
<223> OTHER INFORMATION: Probe

<400> SEQUENCE: 11
acaagggact ttccgctggg gactttccag gg                                     32

<210> SEQ ID NO 12
<211> LENGTH: 26
<212> TYPE: DNA
<213> ORGANISM: Artificial Sequence
<220> FEATURE:
<223> OTHER INFORMATION: Fragment of IL-2 promoter

<400> SEQUENCE: 12
tcgacagagg ggaatctccc agaggc                                            26

<210> SEQ ID NO 13
<211> LENGTH: 26
<212> TYPE: DNA
<213> ORGANISM: Artificial Sequence
<220> FEATURE:
<223> OTHER INFORMATION: Fragment of IL-2 promoter with mutations

<400> SEQUENCE: 13
tcgactctgg gaaatgtccc tgaggc                                            26
```

TPL2 TRANSGENIC KNOCKOUT MICE

FIELD OF THE INVENTION

The present invention relates to moleculy and newly identified polynucleotides and proteins as targets for blocking the activation of certain signal transduction pathways. Specifically, the invention provides methods and compositions for treating inflammatory disorders. More specifically, the invention provides methods for generating animals that have functionally disrupted Tpl2 gene, and methods and compositions targeted to the Tpl2 gene.

BACKGROUND OF THE INVENTION

Protection from microbial pathogens is mediated by a variety of inducible effector mechanisms that are triggered upon encounter with pathogens. The sum of these mechanisms defines antimicrobial immunity which is subclassified into innate and adaptive (See Janeway, Jr. 1989, Cold Spring Harb. Symp. Quant. Biol. 54 Pt 1, 1–13). Innate immunity is triggered by pathogen-associated molecular patterns (PAMPs) which are shared by groups of microbial pathogens and which are recognized by pattern recognition receptors (PRRs) in host cells. (See Medzhitov et al., 1997a, Cell 91, 295–298). PRRs in turn include signaling and endocytic receptors, as well as secreted proteins which bind the microbes and facilitate their phagocytosis or destruction by the complement system. Pathogen-associated molecular patterns are represented by molecules localized on microbial walls. Prominent among them is lipopolysaccharide (LPS) or endotoxin which is derived from the Gram-negative bacteria. LPS consists of four distinct regions: the O-specific chain, the outer core, the inner core, and the lipid A moiety which is responsible for most of the biological effects attributed to LPS. (See Rietschel et al., 1992, Sci. Am. 267, 54–61). Other PAMPs include peptidoglycans which are present primarily in the walls of Gram-positive microorganisms, trehalose diesters which are produced by mycobacteria and corynebacteria, and other Gram-positive bacterial products such as lipotechoic acid. (See Springer, 1990, Nature 346, 425–434; Warren et al., 1986, Annu. Rev. Immunol. 4, 369–388; Lederer, 1979, Springer Semin. Immunopathol. 2, 133–148; Wicken et al., 1980, Biochim. Biophys. Acta 604, 1–26). LPS binds the soluble LPS-binding protein (LBD) and the complex binds CD14, a monocyte/macrophage receptor molecule that is expressed in both soluble and membrane-associated forms. CD14 presents the LPS-LBD complex to the LPS receptor TLR4 (See Medzhitov et al., 1997, Nature 388, 394–397), a member of the Toll family of receptors. TLR4 is the signaling receptor and responds to LPS even in the absence of CD14, whose role is to form, in combination with TLR4, a high affinity receptor.

There are at least 10 members of the Toll receptor family in mammals. (See Rock et al., 1998, Proc. Natl. Acad. Sci. U. S. A. 95, 588–593). Expression of one of these, TLR2, in 293 cells rendered them responsive to LPS suggesting that it is the LPS receptor. More interesting, while TLR4 recognizes LPS, TLR2 recognizes molecules derived from yeast and Gram-positive bacteria. (See Takeuchi et al., 1999, Immunity. 11, 443–451) There are two types of mouse models for the septic shock syndrome. In the first type the syndrome is induced by the administration of a large dose of LPS and is characterized by the development of symptoms over a period of several days to a week (See Fink et al., 1990, J Surg. Res. 49, 186–196; Wise et al, 1980, Circ. Res. 46, 854–859). Mice deficient in ICE (See Li et al., 1995, Cell 80, 401–411) or caspase-11 (See Wang et al., 1998, Cell 92, 501–509), which are required for the processing of IL-1β (See Black et al., 1989, FEBS Lett. 247, 386–390), are resistant to high dose LPS-induced shock, suggesting that IL-1β is the main cytokine responsible for this syndrome. In the second type of model, the syndrome is induced by the administration of a low dose of LPS combined with the transcriptional inhibitor D-Galactosamine (See Galanos et al., 1979, Proc. Natl. Acad. Sci. U. S. A 76, 5939–5943). This gives rise to a rapidly developing syndrome that culminates in death within 6–10 hours. The induction of TNFα by LPS in macrophages, the main cellular target for LPS/D-Galactosamine induced shock, is mediated by both transcriptional and posttranscriptional mechanisms. Particularly important in the posttranscriptional regulation of TNFα is an AU-rich element (ARE) in the 3-untranslated region of the TNFα mRNA (See Han et al., 1990, J Exp. Med 171, 465–475; Han et al., 1990, Eur. Cytokine Netw. 1, 71–75), which regulates the stability of the message and the efficiency by which it is translated (See Kruys et al., 1990, Enzyme 44, 193–202; Kruys et al., 1994, Biochimie 76, 862–866). This element represses translation.

Signals originating in the LPS-triggered TLR4 receptor activate several signaling pathways in target cells such as B cells, which respond by proliferation, and macrophages, which respond by expressing a large number of cytokines and other molecules. Such molecules target the pathogens either directly or indirectly by functionally modifying other cells (See Nathan, 1987, J Clin Invest 79, 319–326). Although these biological responses protect the host against invading pathogens, however, they may also cause harm. Thus, massive stimulation of innate immunity, occurring as a result of severe Gram-negative bacterial infections, leads to excess production of cytokines and other molecules, and the development of a fatal syndrome, the septic shock syndrome, which is characterized by fever, hypotension, disseminated intravascular coagulation and multiple organ failure. (See Parillo, 1993, N Engl J Med 328, 1471–1477). The present invention provides methods and compositions for treating the septic shock syndrome and other inflammatory diseases.

SUMMARY OF THE INVENTION

In the present invention, it has been found that biological and/or pharmacological agent induced and TNFα-dependent septic shock syndrome (or endotoxin shock) and other inflmmatory diseases in animals including humans can be treated by eliminating or interfering with the functional role of the endogenous Tpl2 gene. In general, the present invention provides animals, cells or cell lines having functionally disrupted endogenous Tpl2, methods, and compositions for the treatment of inflammatory diseases that are induced by various biological and pharmacological agents.

In one aspect of the invention, a knock out animal having a functionally disrupted endogenous Tpl2 gene is provided. The knock out animal can be created by the insertion of an exogenous sequence into said gene or by replacement of part of the endogenous Tpl2 gene with an exogenous sequence which results in the animal that lacks the functional Tpl2 protein. Such an animal can be characterized by, for example, its increased resistance to LPS induced endotoxin shock relative to a wild type animal. The knock out animal can also be characterized by its resistance to TNFα-mediated inflammatory diseases by comparison with an animal that expresses a functional Tpl2 gene. The knock out animal can be homozygous for the functionally disrupted endogenous Tpl2 gene or heterozygous for the functionally disrupted endogenous Tpl2 gene. The knock out animals can be mice, rats, rabbits, goats, pigs or monkeys. Spleen cells or microphages isolated from these animals are also provided. A cell line established from immortalized or transformed macro phages isolated from these animals are also provided.

An animal with a structurally intact Tpl2 gene but functionally disrupted endogenous Tpl2 is also provided. For example, functionally disrupted endogenous Tpl2 can be due to the antisense inhibition of mRNA expression or due to the expression of dominant negative mutant Tpl2. These animals can also be characterized by their resistance to LPS induced endotoxin shock or TNFα-mediated inflanmmatory diseases by comparison with an animal that expresses a functional Tpl2.

In another aspect of the invention, a method of identifying Tpl2 specific inhibitors of endotoxin shock is provided. This method includes (a) administering to a first animal expressing a functional Tpl2 gene, and to a second animal having a functionally disrupted endogenous Tpl2 gene, an amount of an endotoxin shock inducing agent wherein the first animal is susceptible to endotoxin shock induced by the agent; (b) administering to the first and second animals, an amount of a putative Tpl2 inhibitor; and (c) determining whether the first animal shows induced resistance to endotoxin shock comparable to that observed in the second animal. The induced resistance to endotoxin shock in the first animal is due to the Tpl2 specific inhibitor.

In still another aspect of the invention, a method of identifying an antagonist to inflammation that is dependent upon a functional Tpl2 gene, is provided. This method includes the following steps: (a) administering to a first animal that expresses a functional Tpl2 gene and to a second animal having a functionally disrupted endogenous Tpl2 gene, an effective amount of an agonist that induces a greater inflammatory response in the first animal than in the second animal; (b) administering to the first and second animals of step (a) a putative Tpl2 inhibitor; and (c) determining the level of inflammatory response in the first animal compared to that of the second animal after step (b). The agonist can be a biological agent or it can be a pharmacological agent such as bleomycin.

In yet another aspect of the invention, a method of determining whether a compound that is known to inhibit Tpl2 activity in vitro also inhibits LPS induced endotoxin shock by specifically inhibiting Tpl2 in vivo. The method includes: (a) administering to a first animal expressing a functional Tpl2 gene and to a second animal having functionally disrupted endogenous Tpl2 gene an effective amount of LPS to induce endotoxin shock in the first animal; (b) administering to the first and second animals an effective amount of the compound that is known to inhibit Tpl2 activity in vitro; and (c) determining whether the first animal shows reduced endotoxin shock comparable to that in the second animal.

In yet another aspect of the invention, a method of determining whether a compound that is known to inhibit Tpl-2 activity in vitro also inhibits TNFα-mediated inflammatory diseases is provided. This method includes: (a) administering to a first animal expressing a functional Tpl2 gene and to a second animal having functionally disrupted endogenous Tpl2 gene an effective amount an agent that induces TNFα production or TNFα-mediated inflammatory response; (b) administering to the first and second animals an effective amount of the compound that is known to inhibit Tpl2 activity in vitro; and (c) determining whether the first animal shows reduced inflammatory response comparable to that in the second animal. Inflammatory diseases include Rheumatoid Arthritis.

In a further aspect, a method of treating or preventing TNFα-mediated inflammatory diseases or LPS induced endotoxin shock in an animal is provided which includes: (a) transfecting bone marrow derived cells in vitro with a DNA construct which encodes sequences that interferes with the expression or function of the endogenous Tpl2 in said cells; and (b) administering an effective amount of said cells after step (a) to the animal. The sequences can be Tpl2 kinase mutant sequences or Tpl2 antisense sequences.

In another aspect of the invention a composition having a DNA construct which encodes sequences that interfere with the expression or function of the endogenous Tpl2 is provided. The sequences include Tpl2 sequences carrying one or more dominant negative mutations and antisense Tpl2 sequences.

In further aspects of the invention, nucleic acids and polypeptides which have been isolated (i.e., altered "by the hand of man" from its natural state, or if it occurs in nature, it has been changed or removed from its original environment) are provided. In one aspect, an isolated Tpl2 polypeptide is provided which can be: (a) an isolated polypeptide comprising an amino acid sequences having at least 95% identity to the amino acid sequence of SEQ ID NO: 2 or 4 over the entire length of SEQ ID NO: 2 or 4; (b) an isolated polypeptide comprising the amino acid sequence of SEQ ID NO: 2 or 4; (c) an isolated polypeptide that is the amino acid sequence of SEQ ID NO: 2 or 4; or (d) a polypeptide that is encoded by a recombinant polynucleotide comprising the polyncleotide sequence of SEQ ID NO: 1 or 3.

In another aspect of the invention, an isolated Tpl2 polynucleotide is provided which can be: (a) an isolated polynucleotide comprising a polynucleotide sequence encoding a polypeptide that has at least 95% identity to the amino acid sequence of SEQ ID NO: 2 or 4, over the entire length of SEQ ID NO: 2 or 4; (b) an isolated polynucleotide comprising a polynucleotide sequence that has at least 95% identity over its entire length to a polynucleotide sequence encoding the polypeptide of SEQ ID NO: 2 or 4; (c) an isolated polynucleotide comprising a nucleotide sequence that has at least 95% identity to that of SEQ ID NO: 1 or 3 over the entire length of SEQ ID NO: 1 or 3; (d) an isolated polynucleotide comprising a nucleotide sequence encoding the polypeptide of SEQ ID NO: 2 or 4; (e) an isolated polynucleotide that is the polynucleotide of SEQ ID NO: 1 or 3; (f) an isolated polynucleotide of at least 30 nucleotides in length obtainable by screening an appropriate library under stringent hybridization conditions with a probe having the sequence of SEQ ID NO: 1 or 3 or a fragment of SEQ ID NO: 1 or 3 of at least 30 nucleotides in length; or (g) a polynucleotide sequence complementary to said isolated polynucleotide of (a), (b), (c), (d), (e) or (f).

BRIEF DESCRIPTION OF THE FIGURES

FIG. 6 shows Tpl2 and LPS-induced activation of NF-κB.

FIG. 16 is the polynucleotide sequence, SEQ ID NO: 1, of human Tpl2 cells.

FIG. 17 is the polypeptide sequence, SEQ ID NO: 2, deduced from the polynucleotide sequence, SEQ ID NO: 1, of human Tpl2.

FIG. 18 is the polynucleotide sequence, SEQ ID NO: 3, of rat Tpl2.

FIG. 19 is the polypeptide sequence, SEQ ID NO: 4, deduced from the polynucleotide sequence, SEQ ID NO: 3, of rat Tpl2.

DETAILED DESCRIPTION OF THE INVENTION

The present invention relates to animals, cells or cell lines having functionally disrupted endogenous Tpl2, methods, and compositions for the treatment of inflammatory diseases that are induced by various bilogical and pharmacological agents.

The Tpl2 protooncogene, also known as Cot, encodes a cytoplasmic serine threonine protein kinase which is activated by provirus integration in MoMuLV induced rodent T cell lymphomas and MMTV induced mammary carcinomas. The Tpl2 is expressed primarily in hematopoietic cells. Provirus integration always occurs in the last intron of the gene and gives rise to mRNA transcripts that encode a carboxy-terminally truncated kinase. The truncated kinase is constitutively active and highly oncogenic. Transgenic mice expressing the truncated form of Tpl2 under the control of a T cell-specific promoter develop T cell lymphoblastic lymphomas by the age of 3 months. (See Ceci et al., 1997, Genes Dev. 11, 688–700).

It is shown by the present invention that the septic shock syndrome and other inflmmatory disorders resulting from various agents in animals including humans can be treated by eliminating or interfering with the functional role of the endogenous Tpl2 gene in animals. For example, by using Tpl2 knockout animals, it is shown here that these animals are resistant to LPS/D-Galactosamine-induced endotoxin shock and that their resistance is due to a posttranscriptional defect in the induction of TNFα in response to LPS, that Tpl2 is required for the activation of the ERK 1 and 2 by LPS, that the ERK pathway is obligatory for the posttranscriptional regulation of TNFα and that one of the targets of the Tpl2/ERK signals responsible for the posttranscriptional regulation of the TNFα mRNA is the AU-rich element in the 3'UTR of the TNFα message. It is also shown here that Tpl2 is involved in the transduction TNFα-generated signals.

Thus, the Tpl2 nucleic acid, and the proteins encoded therefrom (collectively Tpl2 molecules) can be advantageously used as targets for the development of novel therapeutic agents which eliminate the functional role of Tpl2. The Tpl2 molecule of the invention can also be used as research tools to facilitate the elucidation of the mechanistic action of the novel genetic and protein interactions involved in the inflammatory disorders. Accordingly, the present invention provides for the development of methods and compositions for treating inflammatory disorders. Eliminating the functional role of Tpl2 can be achieved by adopting the methods known in the art such as gene targeting or gene knock out, antisense technology or transfecting the cells with constructs that carry dominant mutations in the Tpl2 gene (e.g., dominant mutation in the kinase domain of Tpl2) These knockout animals and the constructs used to generate knockout animals are especially useful in the development of compositions and methods of treating inflammation.

Figure 1:
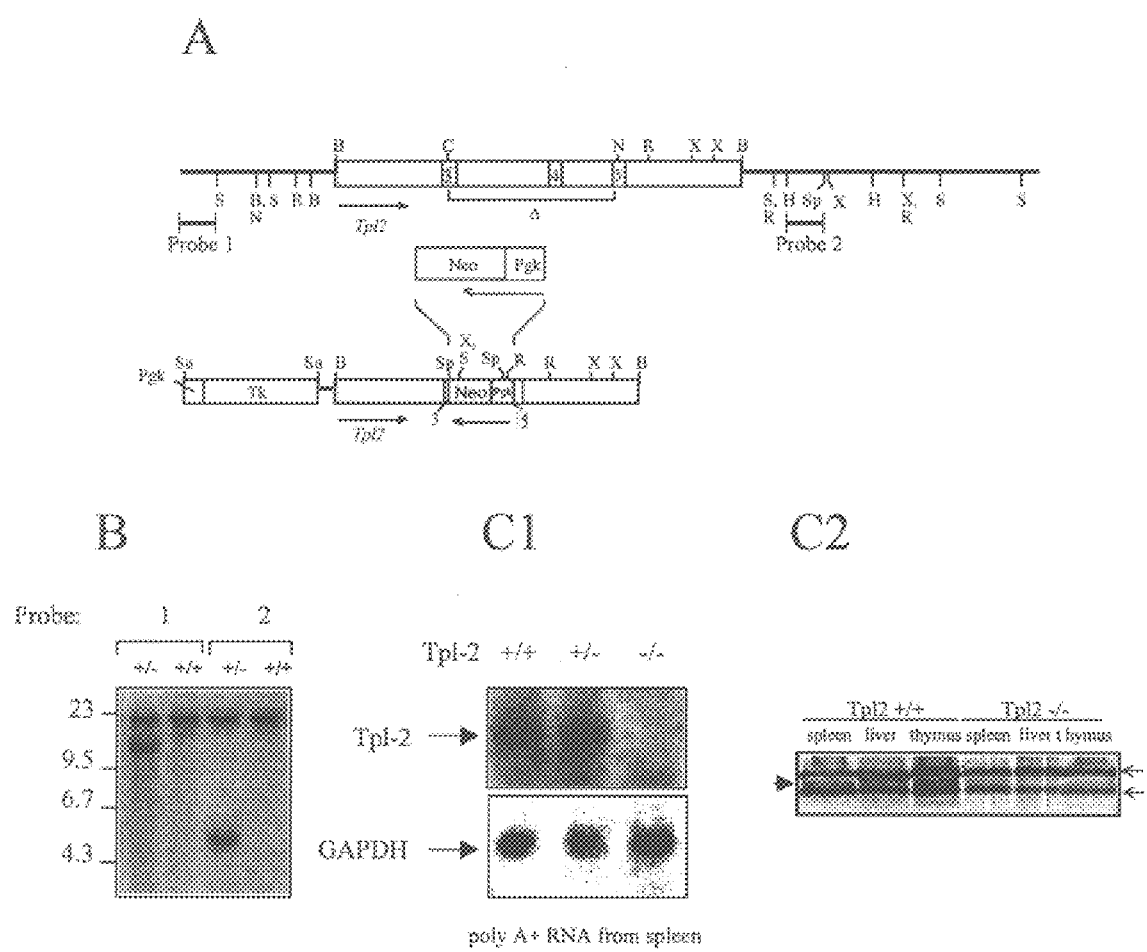
FIG. 1 shows a schematic representation of a method for the construction of Tpl2 targeting construct (A), and establishment of Tpl-2 –/– mice(B, C1 and C2).
Figure 2:
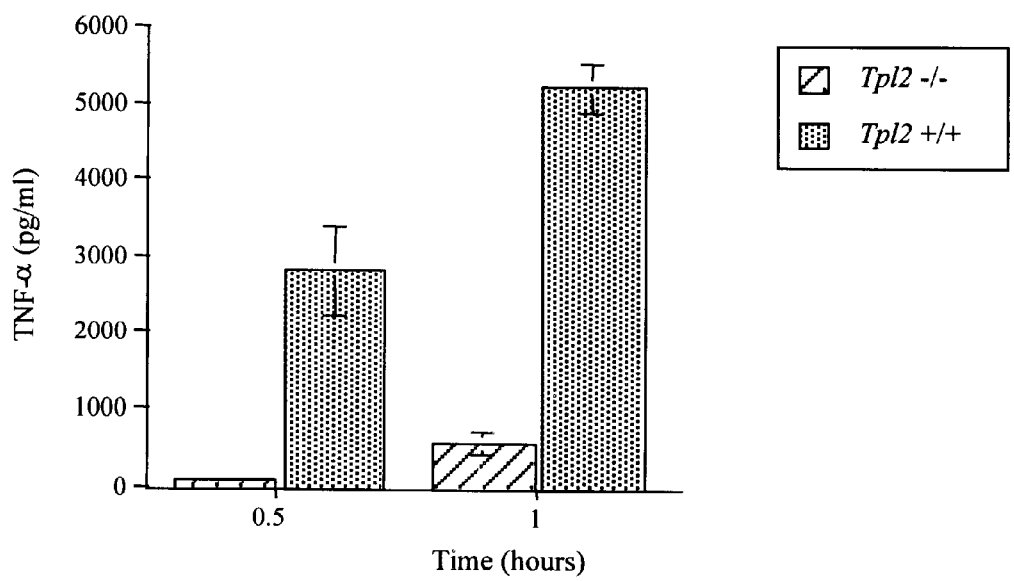
FIG. 2 shows the in vivo effect of Tpl-2 deficiency after treatments with LPS or TNFα.
Figure 2:
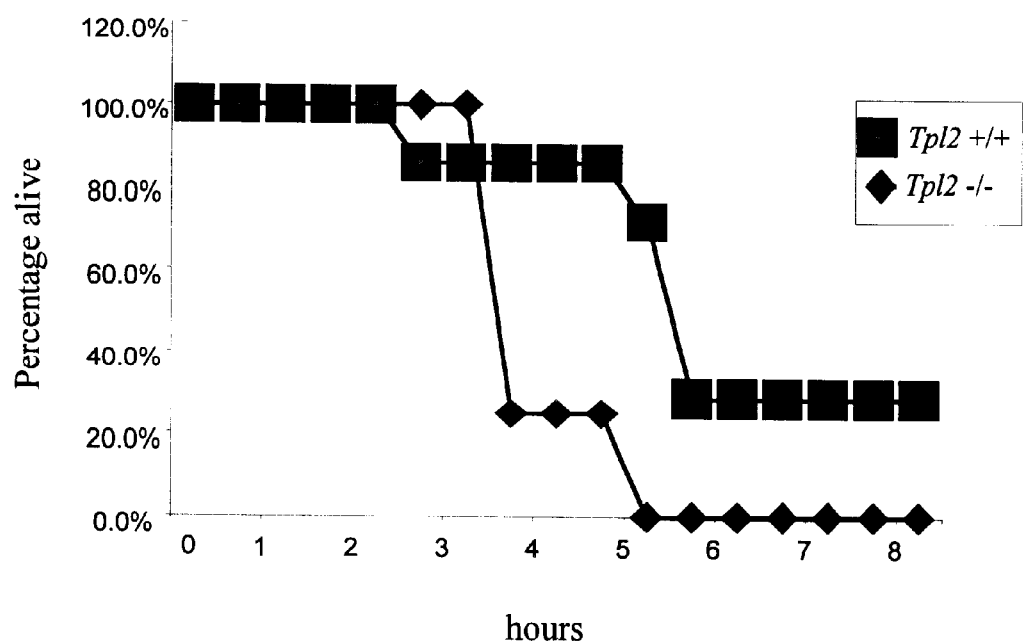

In one preferred embodiment of the invention, to determine the physiological role of the Tpl2 protein at the animal level, Tpl2 knockout mice has been generated by disrupting the Tpl2 gene in ES cells via homologous recombination (FIGS. 1A and 1B). The Tpl2 targeting construct contained the G418-resistance gene flanked by genomic sequences derived from exons 3 and 5 (FIG. 1A). Homologous recombination between the Tpl2 sequences in the construct and the genomic Tpl2 DNA deleted a portion of the Tpl2 catalytic domain including the ATP binding site. Injection of ES cell clones carrying the disrupted Tpl2 gene into blastocysts derived from C57BL/6 mice gave rise to Tpl2 +/−/Tpl2 +/+ chimeras. The chimeras were backcrossed to C57BL/6. Mice utilized in the experiments reported here were derived by brother-sister mating of Tpl2 −/− or Tpl2 +/+ littermates obtained after 9 consecutive backcrosses to C57Bl/6. Thymocytes and splenocytes and liver cells from Tpl2 knockout mice do not express Tpl2 (FIGS. 1C1 and 1C2). The Tpl2 knockout mice developed normally and did not exhibit obvious phenotypic defects. Given that Tpl2 is primarily expressed in hematopoietic tissues, these mice were further analyzed with regard to their hematologic and immunologic phenotype. The results showed that spleens and thymuses are histologically normal and that they contain all the expected cell subsets at the proper ratio. Specifically, the spleens and thymuses of Tpl2 −/− and Tpl2 +/+ mice were shown to contain the same percentage of cells expressing all the CD4/CD8 or B220/Thy12 combinations of markers. Moreover, the spleens and thymuses of the Tpl2 knockout and control mice contained the same overall percentage of cells carrying the markers CD4, CD8, Thy12, B220, Mac-1, Ter-1, CD3, IL-2Rα, TCRαβ and TCRγδ (data not shown). The Tpl2 knockout mice also showed normal antibody responses to the T cell dependent antigen KLH and to the T cell independent antigen LPS-TNP. Following inoculation with lymphocytic choriomeningitis virus (LCMV), they showed normal T cell-mediated cytotoxic responses against LCMV-infected cells (data not shown). Finally anti-CD3 plus anti-CD28-stimulated splenocytes from 8 week old Tpl2 −/− and Tpl2 +/+ mice produced similar levels of cytokines including IL-2, TNFα, IL-4 and IFNγ and incorporated similar amounts of $^3$H-thymidine (data not shown).

To determine whether Tpl2 has a role in the response to inflammatory signals, Tpl2 −/− and Tpl2 +/+ mice were inoculated intraperitoneally (ip) with D-Galactosamine plus increasing doses of lipopolysaccharide (LPS). D-Galactosamine is a hepatotoxic transcriptional inhibitor, which sensitizes the animals to the cytotoxic effects of TNFα. Specifically eight to 12 weeks old mice were sensitized with 1 mg/g of body weight D-glactosamine and injected with the indicated amounts of LPS (from *Salmonella enteritidis*, Sigma L-6011).

The results (See Table 1 below) revealed that Tpl2 knockout mice are resistant to the induction of endotoxin shock. Thus, while all the Tpl2 +/+ mice died within 5–9 hours following injection of LPS, most of the Tpl2 −/− mice survived. The surviving Tpl2 −/− mice were followed for a period of 7 days without any evidence of late occurring ill effects.

TABLE 1

Resistance of Tpl-2 −/− mice to LPS/D-galactosamine-induced endotoxin shock.

| Genotype | Amount of LPS injected (in µg) | Death at 6 hours |
|---|---|---|
| Tpl-2 +/+ | 0.1 | 5/5 |
|  | 1 | 3/3 |
|  | 10 | 9/9 |
| Tpl-2 −/− | 0.1 | 1/7 |
|  | 1 | 0/3 |
|  | 10 | 2/9 |
| Tpl-2 +/− | 1 | 3/3 |

The syndrome arising in LPS/D-Galactosamine-treated mice is characterized by hepatocyte apoptosis and depends on the action of TNFα (See Pasparakis et al., 1996, J Exp. Med 184, 1397–1411; Pfeffer et al., 1993, Cell 73, 457–467), whether Tpl2 −/− mice secrete TNFα in response to LPS was also examined. The results showed that while TNFα was detected in the serum of control mice at 30 minutes, and at 1 hour, following LPS stimulation, it could barely be detected in the serum of Tpl2 −/− mice (FIG. 2A). IL-1β was induced in both the Tpl2 −/− and the control mice (data not shown). To verify that the LPS resistance phenotype is due to the observed defect in TNFα induction and not to a defect in TNFα signaling, Tpl2 −/− and control mice were injected IP with 25 mg D-Galactosamine and with 1.2 µg TNFα intravenously (IV). The results showed that both the Tpl2 −/− and the control mice are TNFα sensitive(FIG. 2B). To determine whether Splenocytes, thioglycollate-elicited peritoneal macrophages (TEPM) and bone marrow derived macrophages (BMDM) from Tpl2 knockout mice are defective in TNFα induction by LPS, short term cultures of unfractionated splenocytes, TEPM and BMDM were stimulated with of LPS. Culture supernatants were collected at the indicated time points and assayed for TNFα using an ELISA assay. FIGS. 3A and B show that both splenocytes and macrophages from Tpl2 knockout mice were defective in TNF(X secretion in response to LPS. This is not due to a general impairment in cytokine release, because at least one cytokine (IL-12) was produced by the Tpl2 −/− macrophages at higher levels than in the Tpl2 +/+ macrophage controls (data not shown). The low responsiveness of the Tpl2 deficient cells to LPS was specific for LPS in that splenocytes from Tpl2 −/− and control animals secreted equivalent levels of TNFα when stimulated with anti-CD3 plus anti-CD28 (FIG. 3A) or PMA plus ionomycin (data not shown).

Moreover, the low responsiveness to LPS was specific for TNFα secretion in that LPS-induced proliferation of spenocytes was equivalent in cells derived from wild type and Tpl2 −/− mice (FIG. 3A, right panel).

To determine whether it was the secretion or the synthesis of TNFα that was defective in cells derived from Tpl2 −/− mice, peritoneal macrophages were treated with LPS plus monensin, which inhibits the transport of proteins from the Golgi apparatus (See Uchida et al., 1980, J Biol. Chem. 255, 8638–8644). Six hours later, the cells were permeabilized with saponin and they were stained with FITC-labeled anti-TNFα antibody. Stained cells were analyzed by flow cytometry. The results (FIG. 3B, right panel) showed that macrophages from Tpl2 −/− mice are defective in TNFα synthesis rather than secretion.

From the finding that the defect in TNFα synthesis in Tpl2 −/− macrophages is LPS specific, it can be determined that Tpl2 functions at the top of the cascade of TNFα induction prior to its convergence with TNFα induction cascades initiated by other stimuli. However, it is unlikely that Tpl2 functions at the level of the LPS receptor because Tpl2 −/− mice secrete IL-1β in response to LPS (data not shown) and splenic B cells from Tpl2 −/− mice proliferate equally well with splenic B cells from Tpl2 +/+ mice following LPS stimulation (FIG. 3A, right panel). To confirm this conclusion, we examined the expression of CD14, the macrophage high affinity receptor at the surface of TEPM from Tpl2 −/− and Tpl2 +/+ mice. The results revealed that peritoneal macrophages from Tpl2 knockout and control mice express similar levels of CD14. Moreover, splenocytes from mice of both genotypes proliferated equally well in response to LPS. We therefore concluded that Tpl2 does not function at the level of the LPS receptor.

Whether the inability of Tpl2 −/− mice to produce normal levels of TNFα in response to LPS is due to a transcriptional or post transcriptional defect was also examined to define the mechanism by which Tpl2 transduces LPS signals and regulate TNFα induction. To this end, Tpl2 −/− and Tpl2 +/+ mice were inoculated with 1 µg LPS IP. RNA from the spleens of the inoculated animals, harvested 1 hour later, was analyzed for TNFα induction using Northern blotting or an RNase protection assay. The results (FIGS. 4A1 and 4A2) showed that the induction of TNFα mRNA is equivalent in spleens of Tpl2 −/− and Tpl2 +/+mice. In parallel experiments, TEPM and BMDM form from Tpl2 −/− and Tpl2 +/+ mice were placed in culture at a concentration of 1×10$^6$ cells/ml. Expression of TNFα was examined by RNase protection before, and 1 hour after stimulation with LPS. The results of this experiment (FIGS. 4B1 and 4B2) were similar to the results of the in vivo experiment in that they also showed that the induction of TNFα mRNA was similar in Tpl2 −/− and Tpl2 +/+ macrophages. The results show that when overexpressed in a variety of cell types, Tpl2 activates the ERK, JNK and p38MAPK pathways, NFAT and NF-κB. Since Tpl2 functions downstream from the LPS receptor but at the top of the LPS-induced TNFα induction cascade, it may contribute to the activation of all these pathways by LPS. It is shown here that the defect in TNFα induction in response to LPS in Tpl2 −/− mice is posttranscriptional.

Next TEPM of Tpl2 −/− and Tpl2 +/+ were stimulated with LPS. Cell lysates harvested before and at the indicated time points after stimulation were analyzed for the activation of MEK1, MEK2, ERK1 and ERK2, as well as for JNK1 and JNK2, and p38MAPK. Activation of the kinases was determined both by Western blotting using antibodies that specifically recognize the phosphorylated, activated forms of these kinases as well as by immunocomplex in vitro kinase assays. The results (FIGS. 5A and 5B) revealed that the inactivation of Tpl2 specifically blocks the activation of ERK1 and ERK2. Identical results were obtained with bone marrow derived macrophages (data not shown).

To determine whether the block in the activation of ERK1 and ERK2 by LPS is responsible for the defect in TNFα induction, we stimulated peritoneal macrophages from normal mice with LPS before and after treatment with the MEK inhibitor PD98059 (See Dudley et al., 1995, Oncogene 13, 2015–2020). Supernatants of these cultures harvested 2 hours later, were analyzed by ELISA for TNFα secretion. Moreover, cell lysates were analyzed for ERK1 and ERK2 activation. The results showed that when the activation of ERK1 and ERK2 is blocked, the induction of TNFα is also blocked (FIGS. 5C1 and 5C2). Activation of ERK1 and ERK2 is therefore obligatory for TNFα induction by LPS. The same experiment was repeated in bone marrow macrophages with similar overall results (data not shown).

To determine whether Tpl2 is required for the activation of NF-κB, NF-κB DNA binding activity in nuclear extracts of peritoneal macrophages before and 60 minutes after LPS stimulation was examined. The results in FIG. 6 show that LPS induced the activation of NF-κB equally well in Tpl2 −/− and Tpl2 +/+cells. In agreement with these data there was no difference in IKKα and β activation in response to LPS in the same cells (data not shown). Since recent studies claimed that Tpl2 plays a critical role in the processing and activation of p105 (NF-κB1) (See Lin et al., (1999), Immunity 10(2):271–80, 271–280), we examined the susceptibility of NF-κB1 knockout mice to LPS/D-galactosamine-induced endotoxin shock. The results showed that NF-κB1 knockout mice are susceptible to shock and excluded NF-κB1 as an important determinant of the described Tpl2 knockout phenotype. Thus Tpl2 is not required for LPS-induced activation of NF-κB. NK-κB1 knockout mice are susceptible to LPS/D-Galactosamine-induced endotoxin shock.

The AU-rich element in the 3'UTR of the TNFα mRNA (3'ARE) destabilizes the RNA and exerts an inhibitory effect on its translation (See Han et al., 1990, J Exp. Med 171, 465–475; Han et al, 1990, Eur. Cytokine Netw. 1, 71–75). TNFα-inducing signals target the 3'ARE and relieve its inhibitory effects. To determine whether the Tpl2-transduced LPS signals responsible for the induction of TNFα target the 3'ARE, we crossed the Tpl2 −/− mice to TNFα ΔARE/− mice which are heterozygous for two different mutations in the TNFα gene. Specifically, in these mice one allele of the TNFα gene is inactivated (−) while the other allele carries a deletion of the 3'ARE (ΔARE). After the appropriate crosses were carried out, we obtained mice of the genotypes shown in FIG. 7. BMDM from these mice (6 mice per group) were stimulated with LPS. Culture supernatants were harvested at the indicated time points and they were analyzed for TNFα by ELISA. The results showed that the loss of the 3'ARE minimizes the difference in TNFα induction by LPS between Tpl2 +/+and the Tpl2 −/− cells. Therefore, the Tpl2-transduced ERK1 and ERK2 activation signals responsible for the induction of TNFα function, at least in part, in a pathway that targets the 3'ARE of the TNFα mRNA. Thus the effect of Tpl2 on the induction of TNFα by LPS depends on the AU-rich element in the 3' untranslated region (3'UTR) of the TNFα mRNA.

The results presented herein show that Tpl2 −/− mice are resistant to LPS/D-Galactosamine-induced endotoxin shock. Their resistance results from a defect in the induction of TNFα in response to LPS. The defect was observed both in vivo as well as in cultures of unfractionated splenocytes and peritoneal and bone marrow derived macrophages. Thus, the expression of CD14, the macrophage high affinity receptor (See Wright et al., (1990), Science 249, 1431–1433) is normal in Tpl2 −/− macrophages. TNFα induction in response to LPS depends on Tpl2-transduced ERK activation signals which regulate the induction of TNFα primarily at the posttranscriptional level. These findings show that the posttranscriptional control of the induction of TNFα by LPS depends not only on the JNK and p38MAPK pathways, but also on the ERK pathway. One of the targets of the LPS-induced Tpl2/ERK activation signals that postranscriptionally regulate the expression of TNFα is the AU-rich elements in the 3'UTR (3'ARE) of the TNFα mRNA. However, the present data clearly show that Tpl2 is required for induction of endotoxin shock in LPS-inoculated mice because it is involved in the transduction of LPS signals that control the expression of TNFα rather than because it function as a transducer of TNFα signals. Thus, the findings presented in this disclosure provide definitive information regarding the physiological signaling role of the Tpl2 protooncogene. In addition, they show that the inactivation of Tpl2 is not only well tolerated in vivo (i.e., Tpl2 knock out animals develop normally) but it also provides protection from LPS-induced endotoxin shock. Thus, Tpl2 as an excellent target for the development of drugs against inflammation and the septic shock syndrome.

In a similar fashion, knock out animals such as rats, rabbits, pigs goats, monkeys and other mammals can be generated to study the effects of the elimination of the functional role of Tpl2 and to screen for drugs at the whole organism level.

Figure 8:
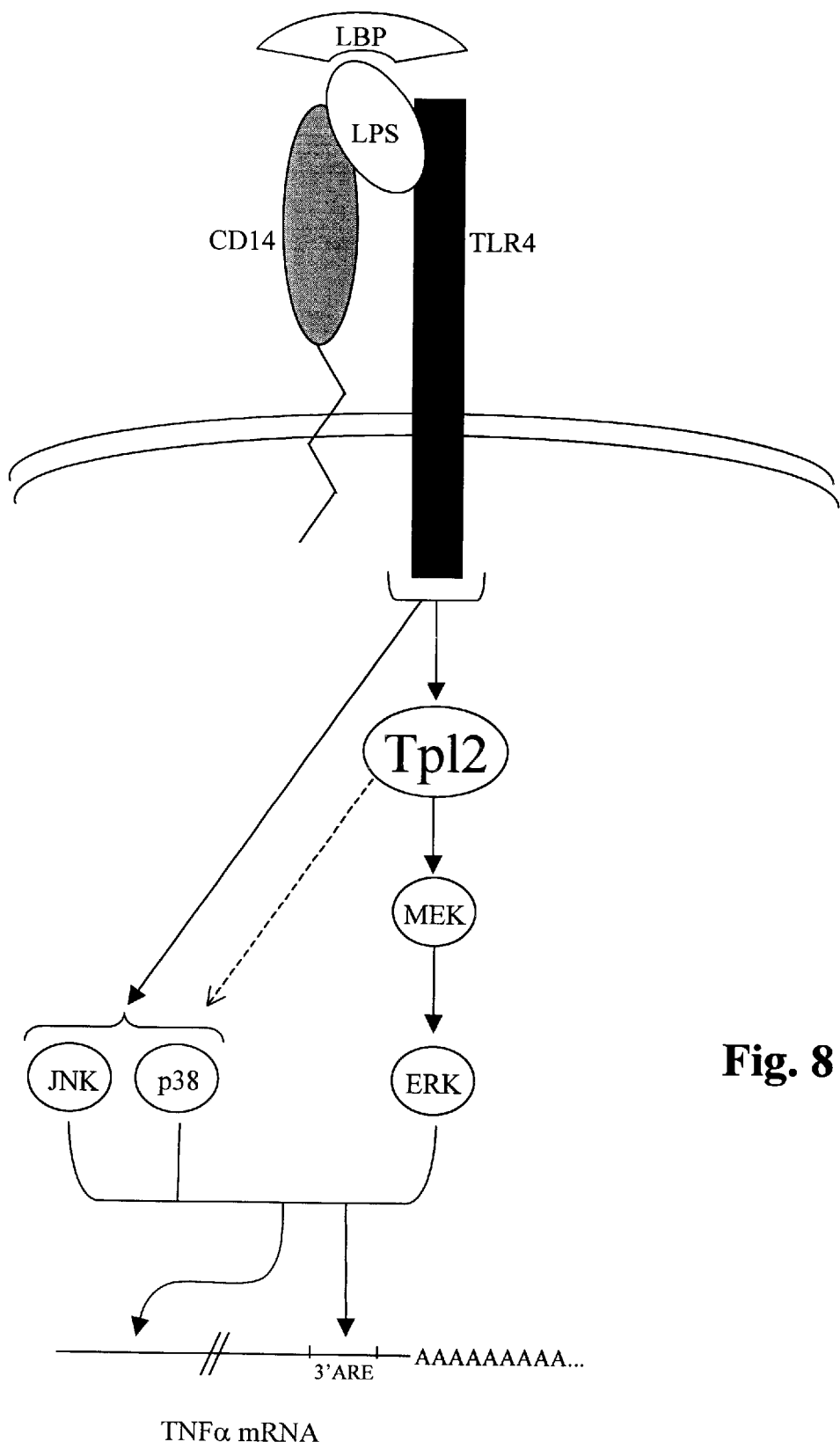
FIG. 8 is a model for the posttranscriptional induction of TNFα by LPS in macrophages.

A model for the posttranscriptional induction of TNFα by LPS in macrophages is shown in FIG. 8. The JNK, p38MAPK and ERK pathways function in concert. One of the targets of the concerted action of these pathways is the 3'ARE of the TNFα mRNA. Tpl2 may transduce signals that contribute to the activation of all three pathways. Earlier studies had shown that inhibition of the JNK or the p38MAPK pathway blocks the induction of TNFα by LPS (See Hambleton et al., 1995, J Exp. Med 182, 147–154; Lee et al., 1994, Nature 372, 739–746; Prichett et al., 1995, J Inflamm. 45, 97–105; Swantek et al., 1997, Mol. Cell Biol. 17, 6274–6282). The same studies have suggested that JNK and the p38MAPK may regulate the induction of TNFα posttranscriptionally perhaps by targeting the 3'ARE of the TNFα mRNA (See Kontoyiannis et al., 1999, Immunity. 10, 387–398). In the present invention it is shown that the MAPKinases ERK1 and ERK2 are also required for TNFα induction and that their activation by LPS depends on Tpl2. Moreover, it is shown here that the Tpl2 effect is mediated primarily by signals that target the 3'ARE in the TNFα mRNA.

As mentioned earlier, the Tpl-2 proto-oncogene encodes a cytoplasmic serine-threonine protein kinase that is activated by provirus integration during the progression stage of retrovirus-induced rodent T cell lymphomas. The integrated provirus is always inserted in the same transcriptional orientation as Tpl-2, in the last intron of the gene. Provirus integration at this site is associated with the expression of a Tpl-2 mRNA transcript that is truncated at its 3' end. The steady-state level of this mRNA is dramatically higher than that of the intact Tpl-2 mRNA in normal T cells and in T cell lymphomas with an unrearranged Tpl-2 locus. The 3' truncated Tpl-2 mRNA encodes a protein with an altered carboxy-terminus in which forty-three amino acids encoded by the last Tpl-2 exon are replaced by seven amino acids encoded by intron sequences.

The provirus integration in the Tpl-2 locus occurs during the progression stage of retrovirus-induced rodent T cell lymphomas, and may contribute to neoplastic transformation in cooperation with other oncogenes. The carboxyterminally truncated Tpl-2 may also initiate neoplastic transformation. Transgenic mice expressing the carboxyterminally truncated, but not the wild-type Tpl-2, develop spontaneous T cell lymphomas at an early age (Ceci, et al., 1997, Genes & Development 11:688–700). The enhanced oncogenic potential of the truncated Tpl-2 protein correlates with its higher catalytic activity and its higher ability to activate the MAPK and SAPK pathways (Ceci, et al., 1997, Genes & Development 11:688–700).

Although Tpl-2 was originally identified as a gene involved in leukemogenesis, more recent studies have shown that it is also expressed in non-hematopoietic tissues as well as in a variety of non-hematopoietic tumors and cell lines including NIH3T3 cells (Chan, et al., 1993, Oncogene 8:1329–33; Ohara, et al., 1995, Journal of Cell Science 108:97–103). Particularly interesting were recent findings showing that Tpl-2 is also activated by provirus insertion in mouse mammary tumor virus-induced mammary carcinomas. These findings indicate that Tpl-2 contributes to the induction and progression of not only hematopoietic but also of non-hematopoietic neoplasms. Early studies showing that Tpl-2 activates the MAPK and SAPK cascades (Ceci, et al., 1997, Genes & Development 11: 688–700.; Patriotis, et al., 1994, Proc. Natl. Acad. Sci. USA 91:9755–9; Salmeron, et al., 1996, Embo Journal 15:817–26), did not determine the physiological signals transduced by Tpl-2 and activating these cascades. It is disclosed by the present invention that Tpl-2 contributes to the transduction of TNF-α-generated signals. TNF-α is a cytokine that is derived primarily from activated macrophages and elicits highly diverse biological effects including mitogenesis (Tartaglia, et al., 1993, Journal of Immunology 151:4637–41), cell cycle arrest, apoptosis and differentiation (Raines, et al., 1993, Journal of Biological Chemistry 268:14572–5). In intact animals it plays an important role as an immunomodulator and as a mediator of cytotoxicity and inflammation (Rothe, et al., 1993, Nature 364:798–802). The TNF-α-induced signals are transduced by two distinct receptors, TNF-R1 (p55) and TNF-R2 (p75) (Barrett, et al., 1991, European Journal of Immunology 21:1649–56). Although most TNF-α signals are transduced by both receptors, apoptotic signals are transduced primarily by TNF-R1. The carboxy-terminus of TNF-R1, but not TNF-R2, shares with other proteins involved in apoptosis an ~80-amino acid protein-protein interaction domain known as the death domain (Tartaglia, et al., 1993, Cell 74:845–53). Through this domain TNF-α-engaged TNF-R1 binds in a hierarchical order to a series of other death domain containing proteins including TRADD (Hsu, et al, 1995, Cell 81:495–504), RIP (Stanger, et al., 1995, Cell 81:513–23) and FADD (Grimm, et al., 1996, Proceedings of the National Academy of Sciences of the United States of America 93:10923–7) and induces apoptosis. Associated with this receptor via TRADD is also a protein, TRAF2, which does not contain a death domain and is involved in the activation of NF-κB (Hsu, et al., 1996, Cell 84:299–308).

Signals originating in TNF-R1 activate two distinct pathways. One requires TRADD, RIP and FADD and induces apoptosis, while the other requires TRADD and TRAF2 and activates SAPK and NF-κB (Hsu, et al., 1995. Cell 81:495–504; Ichijo et al., 1997, Science 275:90–94). TRADD, which associates with the receptor in a TNF-α-dependent manner, is required for the transduction of signals along both pathways (Hsu, et al., 1996, Cell 84:299–308; Hsu, et al., 1995. Cell 81:495–504). It is shown by the present invention that Tpl-2 is involved in the activation of both pathways by TNF-α. In the absence of TNF-α, Tpl-2 interacts with TRADD. TNF-α stimulation activates Tpl-2 and abrogates its interaction with this protein thus, Tpl2 is involved in the transduction of TNF-α signals which is mediated via TRADD.

To determine whether Tpl-2 transduces TNF-α signals COS-1 or 293 cells were co-transfected, which express low levels of Tpl-2, with HA•JNK1 and the kinase-dead, dominant negative mutant Tpl-2K167M. Following overnight serum starvation, the cells were treated with EGF, TNF-α, IL-1β or UV irradiation and they were analyzed to determine the effect of these stimuli on the activity of HA.NK1. The results showed that Tpl-2K167M inhibits the TNF-α-induced activation of JNK1 but has no effect on the activation of this kinase by all other tested factors (FIG. 1). Additional experiments revealed that Tpl-2K167M also specifically inhibits the TNF-α-induced activation of the MAPK ERK1 (data not shown). Thus jit is shown here that Tpl-2 transduces TNF-A signals.

Tpl-2 transduces TNF-α signals that activate the MAPK and SAPK pathways in a variety of cell types including 293 cells (data not shown) which express primarily TNF-R1 (18, 39). Moreover, Tpl-2 is activated in murine NIH3T3 cells by human TNF-α (FIG. 2B) which in these cells triggers only TNF-R1. Thus it is shown in this disclosure that Tpl-2 transduces TNF-α signals originating in TNF-R1 may also transduce signals originating in TNF-R2.

To determine whether Tpl-2 contributes to the transduction of TNF-α apoptotic signals NIH3T3 cells were infected with the SRα retrovirus vector or with SRα-based constructs of either the wild-type Tpl-2 or the dominant negative mutant Tpl-2K167M. Each construct was introduced stably into three independent cultures of NIH3T3 cells. Cells grown to ~75% confluency were trypsinized and plated into 35 mm petri dishes at 0.75×10$^5$ cells per dish. Forty-eight hours later they were treated with murine or human TNF-α. Following an additional period of 24 or 48 h, the cells were trypsinized and stained with propidium iodide (PI). The percentage of cells stained with PI (dead cells) was determined by flow cytometry. The results showed that Tpl-2wt potentiates, while Tpl-2K167M inhibits TNF-α-induced cell death (FIG. 2A). Ethidium bromide staining and flow cytometry of cell nuclei confirmed that the observed cell death was due to apoptosis (data not shown). The same experiment was repeated three times with similar results.

The effects of TNF-α in NIH3T3.S26 cells expressing the dominant negative mutant Tpl-2K167M from a tetracycline-tTA-regulated promoter which is induced in the absence of tetracycline was also examined. To this end, cells cultured in the presence or absence of the tetracycline analog doxycycline (DOX) (FIG. 2B), were treated with human TNF-α. Thirty-six hours later, it was shown by light microscopy that expression of Tpl-2K167M protected the cells from the severe apoptotic effects of TNF-α (FIG. 2C). These results were confirmed by PI-staining and flow cytometry of the same cells (FIG. 2C, insets). Vector-transfected NIH3T3.S26 cells treated with DOX at similar doses showed no toxicity. In addition, treatment of these cells with TNF-α induces the same level of toxicity both in the presence and absence of DOX (data not shown).

Figure 3:
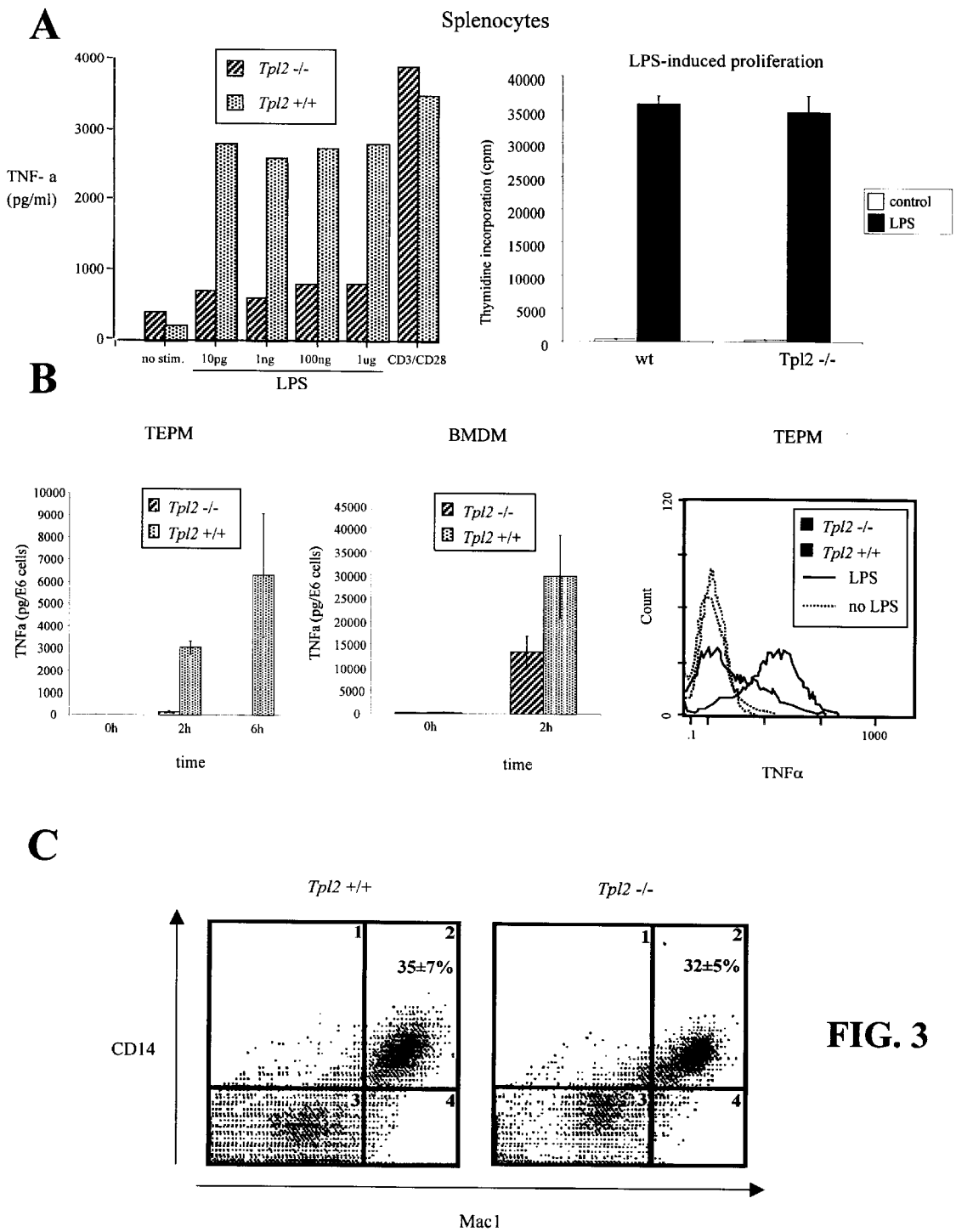
FIG. 3 shows LPS Treatments and TNFα production in Splenocytes, thioglycollate-elicited peritoneal macrophages (TEPM) and bone marrow derived macrophages (BMDM) from Tpl2 –/– mice and Tpl2 +/+ mice (or wt mice).

TNF-α induces apoptosis by activating members of the protease family of caspases. Activation of these proteases is detected both by monitoring the proteolytic cleavage of their substrates as well as by measuring their activity directly. To measure the activity of caspase-3, a caspase family member that is activated by TNF-α (29), an assay was used that monitors the cleavage of a tetrapeptide imitating the CPP32/YAMA cleavage site on poly (ADP-ribose) polymerase (PARP). This tetrapeptide (DEVD-AFC) is conjugated to a fluorescent dye which fluoresces only after cleavage. The results of this assay confirmed that whereas Tpl-2 wt potentiates, Tpl-2K167M inhibits the induction of caspase-3 activity following treatment with TNF-α (FIG. 3).

It is also shown here that, Tpl-2 contributes also to the transduction of TNF-α apoptotic signals. Since Tpl-2 is constitutively active when overexpressed in different cell types the acute overexpression of wild-type Tpl-2 may induce apoptosis in the absence of TNF-α. Wild-type Tpl-2 or Tpl-2K167M can be expressed in an extablished cell line such as the rat embryo fibroblast cell line REF52 from a tetracycline-rtTA-regulated promoter which is induced in the presence of tetracycline. For example, in one experiment, cells grown to ~75% confluency were trypsinized and seeded in 35 mm petri dishes at a density of $0.75 \times 10^5$ cells per dish. Twenty-four hours later, the cells were cultured in DMEM supplemented with either 10% or 0.5% FBS in the presence or absence of doxycycline (FIG. 4A). Following an additional 24 h period the percentage of dead cells was determined either by PI-staining and flow cytometry (FIG. 4B) or by trypan blue exclusion and light microscopy (data not shown). The DNA content of the cells was determined by staining cell nuclei with ethidium bromide and flow cytometry. The results confirmed that cell death induced by acute overexpression of wild-type but not kinase-dead Tpl-2 is due to apoptosis (FIG. 4C). The inability of Tpl-2K167M to induce apoptosis is because the apoptotic effect of Tpl-2 depends on its kinase activity.

It is known here that the pathway leading to the activation of the SAPK cascade following TNF-α stimulation converges with the NF-κB activation pathway It is shown here that Tpl-2 contributes to the transduction of TNF-α signals that activate NF-κB The following experiment was conducted: NIH3T3 cells stably infected with the SRα, Tpl-2 wt.SRα or Tpl-2K167M.SRα retrovirus constructs and expressing low levels of Tpl-2 were treated with human TNF-α for 5, 10, 15 or 60 min and they were harvested in an NP-40 lysis buffer. NF-κB DNA binding activity in the nuclear fraction of the resulting lysates was determined by electrophoretic mobility shift assays (EMSAs) using an NF-κB specific $^{32}$P-labeled double-stranded oligonucleotide probe derived from the HIV LTR. The results (FIG. 5A*a*) revealed that wild-type Tpl-2 potentiates, while Tpl-2K167M attenuates the activation of NF-κB by TNF-α. Western blots of the cytosolic fraction of the same cells probed with anti-IκB-α and anti-IκB-β antibodies (FIGS. 5A*b* and 5A*c*) confirmed that in NIH3T3 cells the activation of NF-κB following TNF-α treatment correlates with the degradation of IκB-α but not IκB-β (Thanos, et al., 1995, Cell 80:529–32; Thompson, et al., 1995, Cell 80:573–82). The same Western blots revealed that the level of IκB-α at 60 min following TNF-α treatment was highest in Tpl-2 wt.SRα and lowest in Tpl-2K167M.SRα-infected cells (FIGS. 5A*b* and 5A*d*). Since NF-κB induces expression of IκB-α but not IκB-β (de Martin, et al., 1993, EMBO Journal 12:2773–9; Le Bail, et al., 1993, EMBO Journal 12:5043–9), these results independently confirm that Tpl-2 contributes to the transduction of TNF-α signals that activate NF-κB in vivo.

The main EMSA-band induced by TNF-α in NIH3T3 cells contains p65/p50 heterodimers (Rothe, et al., 1995, Science 269:1424–7). The wild-type Tpl-2 enhances and Tpl-2K167M downregulates the formation of these complexes and it is disclosed here that the NF-κB-activation signals transduced by Tpl-2 contribute to the processing and nuclear translocation of p65 and p 105/p50 molecules.

To determine whether activation of Tpl-2 is sufficient to induce NF-κB activity the ability of overexpressed, constitutively active Tpl-2 to induce transcription from an NF-κB-dependent promoter was examined. To this end, EL4 cells were transiently transfected with a chloramphenicol-acetyl-transferase (CAT) reporter construct in which CAT is under the control of a minimal thymidine kinase (TK) promoter with one copy of the IL-2 promoter NF-κB binding site placed upstream. A construct containing a mutant binding site that fails to bind NF-κB (mNF-κB) was used as a control. Co-transfection of Tpl-2 wt with the reporter constructs in the combinations shown in FIG. 5B showed that Tpl-2 activates the NF-κB.CAT but not the mNF-κB.CAT promoter. Thus, it is shown that Tpl-2 activates NF-κB.

Figure 7:
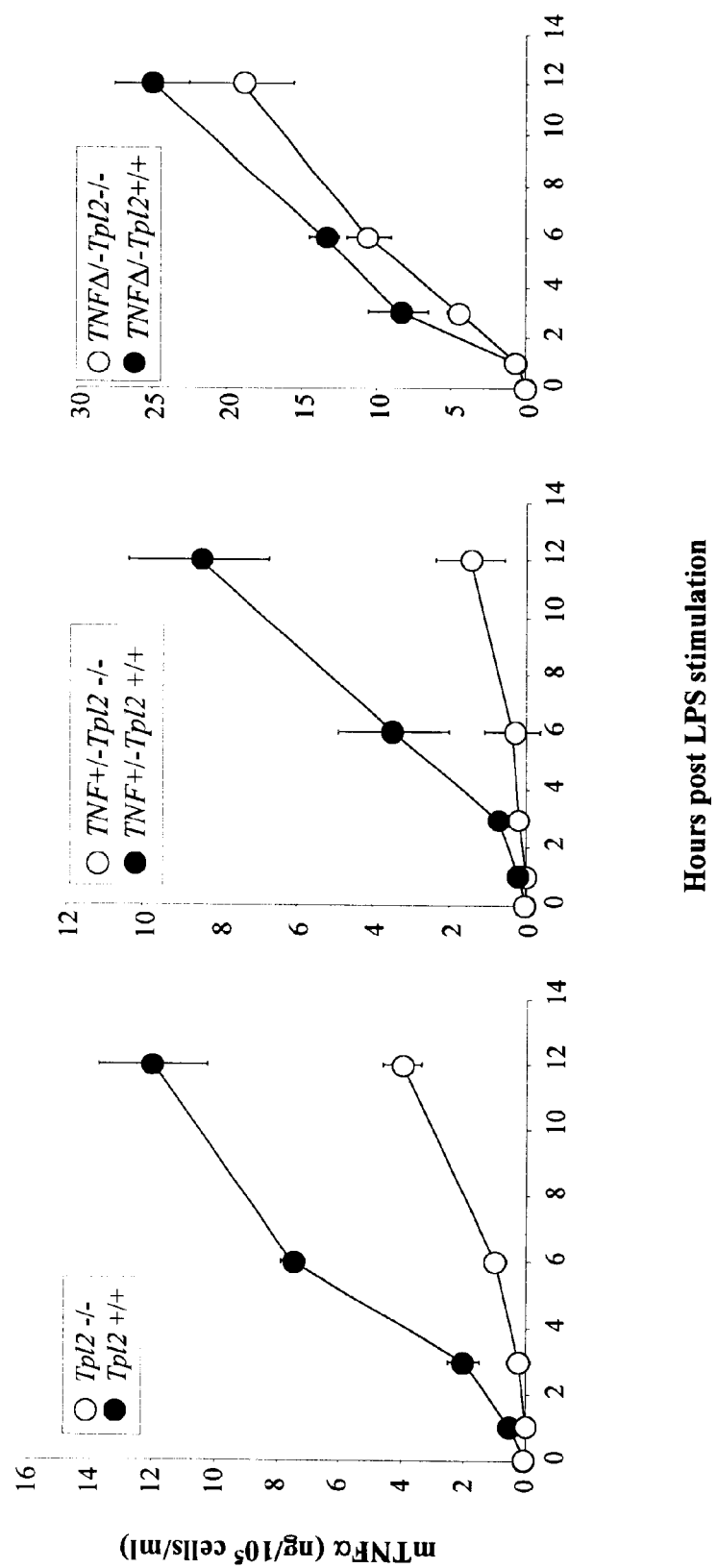
FIG. 7 are graphs showing the results related to the effect of Tpl2 on the induction of TNFα by LPS and influence of the AU-rich element in the 3'UTR of the TNFα mRNA.

It is also shown by this present invention that Tpl-2 interacts with TRADD and this Tpl-2 transduces TNF-α signals leading to apoptosis and to the activation of the MAPK and the SAPK/NF-κB pathways. For example, in one experiment, whether wild-type and kinase-dead Tpl-2 interact with TRADD was examined. To this end, 293 cells were transiently transfected with the pCMV5 expression vector or with pCMV5 expression constructs of c-myc-epitope tagged wild-type Tpl-2 (Tpl-2 wt.MT) or kinase-dead Tpl-2 (Tpl-2K167M.MT). Forty-eight hours later half of the transfected cultures were treated with TNF-α for 10 min. Both the TNF-α-treated and untreated cultures were then lysed in an NP-40 lysis buffer and the endogenous TRADD protein was immunoprecipitated using an affinity purified rabbit polyclonal antibody. A Western blot of the TRADD immunoprecipitates was then probed with the anti-c-myc tag monoclonal antibody 9E10.2 (FIG. 7, lanes 1–6). The same antibody was used to probe a Western blot of total lysates from the same cells (FIG. 7, lanes 7–10). A Tpl-2 co-migrating band co-immunoprecipitates with TRADD from lysates of untreated but not TNF-α -treated Tpl-2 wt-transfected 293 cells (lanes 1 and 2, respectively). The inability to detect a similar size band in TRADD immunoprecipitates from lysates of vector-transfected cells (lanes 3 and 4) confirmed that the co-immunoprecipitating band is Tpl-2. Co-immunoprecipitation of the kinase-dead Tpl-2 mutant (lanes 5 and 6) was observed in both TNF-α treated and untreated cells indicating that the abrogation of Tpl-2 binding to TRADD following TNF-α treatment depends on the activation of Tpl-2 by TNF-α.

Figure 15:
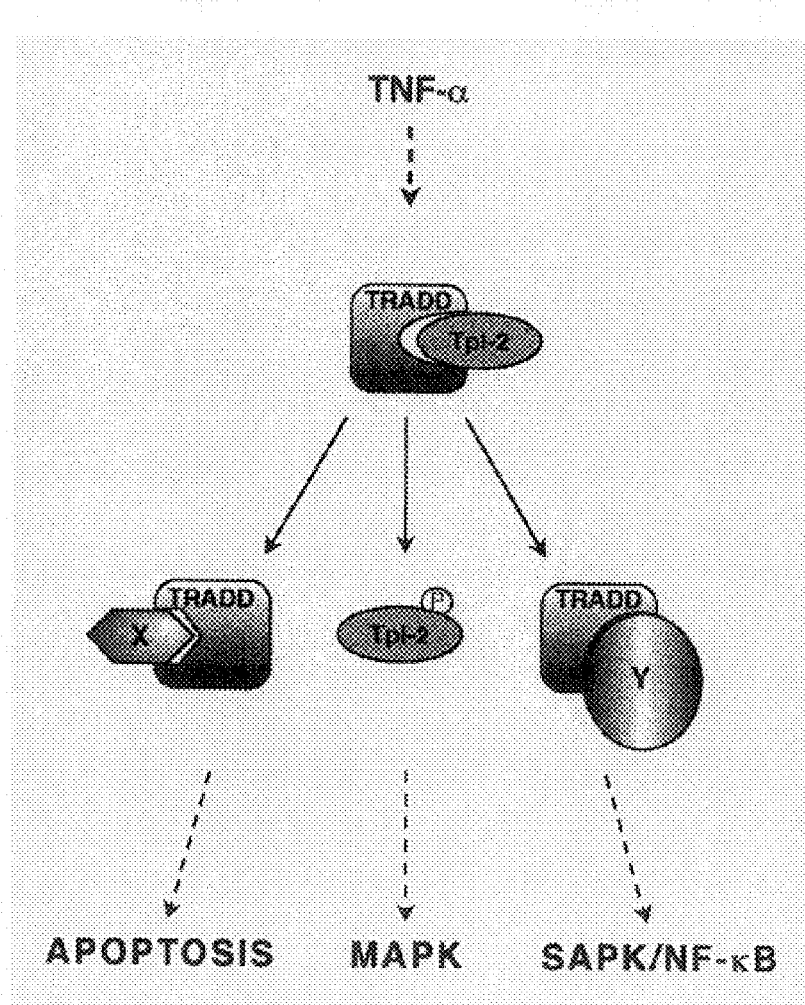
FIG. 15 shows a model for the role of Tpl2 in TNFα signaling.

A model for role of Tpl-2 in TNF-α signaling is shown in FIG. 15. Tpl-2 forms complexes with TRADD in the absence of TNF-α. Activation of Tpl-2 by TNF-α leads to the destabilization and disruption of the Tpl-2/TRADD complexes perhaps because of phosphorylation of TRADD. Following its release from Tpl-2, TRADD transduces downstream signals activating the apoptotic and SAPK/NF-κB pathways through its interaction with downstream target proteins (X and Y). The activated Tpl-2 that is released from TRADD may be responsible for the TNF-α-dependent activation of the MAPK.

According to another aspect of the invention, Tpl2 encoding nucleic acid molecules and polypeptides encoded by such nucleic acid molecules are provided. Shown in FIG. 16 is the cDNA sequence of human Tpl2 (called Cot clone) (SEQ ID NO: 1) from human cells. Referring to FIG. 16, SEQ ID NO: 1, first 79 nucleotides and last 103 nucleotides (i.e., nucleotide starting with the number 1753 to nucleotide with the number 2001) are vector PCRII/TOPO Sequences.

Starting from the nucleotide 80 to nucleotide 318 are 5'UTR. The nucleotides 319 through 1719 encode the polypeptide of SEQ ID NO: 2 (shown in FIG. 17 which is further described below). The stop condon begins at nucleotide 1720 of SEQ ID NO: 1. The start (ATG) and stop (TGA) condons are underlined in FIG. 16. The nucleotides after the stop condon in FIG. 16 i.e., nucleotide from 1723 to nucleotide 1778 are 3'UTR. Shown in FIG. 17 is a human Tpl2 polypeptide sequence (SEQ ID NO: 2) encoded by the human Tpl2 polynucleotide nucleotide sequence (SEQ ID NO: 1). Shown in FIG. 18 is the cDNA sequence of Tpl2 (called Cot 1) (SEQ ID NO: 3) from rat. Referring to FIG. 18, the polynucleotide of SEQ ID NO: 3 between nucleotide number 318 through number 1718 encodes the polypeptide of SEQ ID NO: 4 (shown in FIG. 19 which is further described below). The stop codon begins at nucleotide 1719. Shown in FIG. 19 is a rat Tpl2 polypeptide sequence (SEQ ID NO: 4) encoded by the rat Tpl2 polynucleotide sequence (SEQ ID NO: 3). These molecules have the benefit of nucleic acid among other things, being useful to screen compounds or agents for preventing septic shock syndrome or inflammatory disorders.

The nucleic acid molecules of the present invention can be prepared by any of the methods known in the art. For example, they can be prepared by synthesis from appropriate nucleotides or isolation from biological sources. These isolation methods utilize protocols well known in the art. The availability of nucleotide sequence information, such as a cDNA having SEQ ID NO: 1 or 3 enables preparation of an isolated nucleic acid molecule of the invention by oligonucleotide synthesis. Synthetic oligonucleotides can be prepared by the methods known in the art (for example, phosphoramidite method employed in the Applied Biosystems 38A DNA Synthesizer or similar devices). The resultant construct may be purified according to methods known in the art, such as high performance liquid chromatography (HPLC). It is known that long double-stranded polynucleotides, such as a DNA molecule of the present invention, must be synthesized in stages, due to the size limitations inherent in current oligonucleotide synthetic methods. Thus, for example, a Tpl2 encoding double-stranded nucleic acid molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire Tpl2 encoding double-stranded molecule. A synthetic DNA molecule so constructed may then be cloned and amplified in an appropriate vector.

Nucleic acid sequences encoding Tpl2 proteins can be isolated from appropriate biological sources using methods known in the art. In one embodiment, a cDNA clone is isolated from a cDNA expression library of human origin (as that shown in FIG. 9). In an alternative embodiment, utilizing the sequence information provided by the cDNA sequence, human genomic clones encoding Tpl2 proteins can be isolated. Alternatively, cDNA or genomic clones having homology with Tpl2 can be isolated from other species using oligonucleotide probes corresponding to predetermined sequences within the Tpl2 encoding nucleic acids.

In accordance with the present invention, nucleic acids having the appropriate level of sequence homology with the protein coding region of SEQ ID NO: 1 or 3 may be identified by using hybridization and washing conditions of appropriate stringency. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention. For example, hybridizations can be performed, according to the method of Sambrook et al., (supra) using a hybridization solution comprising: 5×SSC, 5×Denhardt's reagent, 1.0% SDS, 100 mg/ml denatured, fragmented salmon sperm DNA, 0.05% sodium pyrophosphate and up to 50% formamide.

The invention also relates to vectors having a polynucleotide or polynucleotides of the invention, host cells that are genetically engineered with vectors of the invention to expression systems that has a polynucleotide or polynucleotides of the present invention, to host cells that are genetically engineered with such expression systems, and to the production of polypeptides of the invention by recombinant techniques. Cell-free translation systems can also be employed to produce such proteins using RNAs derived from the DNA constructs of the invention. Recombinant polypeptides of the present invention can be expressed by processes well known to those skilled in the art in genetically engineered host cells including expression systems.

Nucleic acids of the present invention can be maintained as DNA in any convenient cloning vector. In a preferred embodiment, clones are maintained in a plasmid cloning/expression vector, such as pbluescript (Stratagene, La Jolla, Calif.), which is propagated in a suitable E. coli host cell.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as, calcium phosphate transfection, DEAE-dextran mediated transfection, transvection, microinjection, cationic lipid-mediated transfection, electroporation, transduction, ballistic introduction and coinfection.

Representative examples of appropriate hosts include bacterial cells such as cells of E. coli, Bacillus subtilis, and Streptococcus pneumoniae; fungal cells such as cells of a yeast, insect cells such as cells of Drosophila; animal cells such as CHO, COS, HeLa, melanoma cells; and plant cells such as cells of plants that can be readily cultured in vitro.

A great variety of expression systems where a nucleic acid of interest is operably linked to a promoter can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, adenoviruses, and retroviruses, and vectors derived from combinations thereof, such as those derived from plasmid and bacteriophage genetic elements, such as cosmids and phagemids. The expression system constructs may have control regions that regulate expression. Generally, any system or vector suitable to maintain, propagate or express polynucleotides and/or to express a polypeptide in a host can be used for expression. The appropriate DNA sequence may be inserted into the expression system by any of a variety of well-known and routine techniques, such as, for example, those set forth in standard laboratory manuals.

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Tpl2-encoding nucleic acid molecules of the invention include cDNA, genomic DNA, RNA, and fragments thereof. Thus, this invention provides oligonucleotides (sense or antisense strands of DNA or RNA) having sequences capable of hybridizing with at least one sequence of a nucleic acid molecule of the present invention, such as selected segments of the cDNA having SEQ ID NO:1 or 3. Such oligonucleotides are useful as probes for detecting or isolating Tpl2 genes. Antisense nucleic acid molecules can be targeted to translation initiation sites and/or splice sites to inhibit the production of the Tpl2 proteins. Such antisense molecules are typically between 15 and 30 nucleotides and length and span the translational start site of Tpl2 encoding mRNA molecules.

Further embodiments of the invention include biologically, clinically or therapeutically useful polynucleotides and polypeptides, and variants thereof, and compositions comprising the same. It will be appreciated by persons skilled in the art that variants (e.g., allelic variants) of these sequences exist in the human population, and thus various specific nucleotide sequences and variants thereof that would occur in a given population must be taken into account when designing and/or utilizing oligos of the invention. The usage of different wobble codons and genetic polymorphisms which give rise to conservative or neutral amino acid substitutions in the encoded protein are also examples of such variants. The variants can be, for example, an isolated polynucleotide comprising or consisting of: (a) a polynucleotide sequence that has at least 95% identity, even more preferably at least 97–99% or exact identity to SEQ ID NO: 1 or 3 over the entire length of SEQ ID NO: 1 or 3, or the entire length of that portion of SEQ ID NO: 1 or 3 which encodes SEQ ID NO: 2 or 4; (b) a polynucleotide sequence encoding a polypeptide that has at least 95% identity, even more preferably at least 97–99% or 100% exact, to the amino acid sequence of SEQ ID NO: 2 or 4, over the entire length of SEQ ID NO: 2 or 4. Accordingly, it is within the scope of the present invention to encompass such variants, with respect to the Tpl2 sequences disclosed herein or the oligos targeted to specific locations on the respective genes or RNA transcripts. Additionally, oligo sequences that may not be perfectly matched to a target sequence, but the mismatches do not materially affect the ability of the oligo to hybridize with its target sequence under the conditions described are also included.

Relatedness between two or more polypeptide sequences or two or more polynucleotide sequences can be measured in terms of "identity" or, for polypeptides, in terms of "similarity." While the term is used to indicate strong relatedness, this relatedness does not need to meet any criteria for evolutionary relatedness. Also, the calculation can be an absolute calculation of identity between two strings of sequences, to give the largest match between the sequences tested without discarding any reductions for non-matches between the sequences.

By way of example, a polynucleotide sequence of the present invention can be identical to a reference sequence (such as SEQ ID NO: 1 or a relevant segment thereof), that is it can be 100% identical, or it can include up to a certain integer number of nucleic acid alterations as compared to the reference sequence such that the percent identity is less than 100% identity. Such alterations can include nucleic acid deletions, substitutions (including transitions and transversions), or insertions, and wherein such alterations can occur relative to the 5' or 3' terminii of the reference polynucleotide sequence or anywhere between the terminal positions, interspersed either individually among the nucleic acids in the reference sequence or in one or more contiguous groups within the reference sequence. As an illustration, by a polynucleotide having a nucleotide sequence having at least, for example, 95% "identity" to a reference nucleotide sequence of SEQ ID NO: 1 it is intended that the nucleotide sequence of the polynucleotide is identical to the reference sequence except that the polynucleotide sequence can include an average of up to five point mutations per each 100 nucleotides of the reference nucleotide sequence of SEQ ID NO: 1. For polypeptide sequence comparisons, such alterations can be amino acid deletions, substitutions, including conservative and non-conservative substitutions, or insertions, and the alterations can occur relative to the amino- or carboxy-terminii of the reference polypeptide sequence or anywhere between those terminal positions, interspersed either individually among the amino acids in the reference sequence or in one or more contiguous groups within the reference sequence.

Thus, unless another meaning is specified, this application will speak of relatedness between two strings of sequence (a query string and a reference string) in terms of a query sequence that is identical with the reference sequence, or, if not identical, then over the entire length corresponding to the reference sequence, the nucleic acid sequence has an average of up to thirty (or twenty, ten, five, two or one) substitutions, deletions or insertions for every 100 nucleotides or amino acid residues of the reference sequence. In one embodiment there is one substitution, deletion or insertion for every 200 nucleotides or amino acid residues of the reference sequence. This measure can be viewed as 70% identity when there are thirty alterations per hundred, 80% when there are twenty alterations, 90% when there are 10 alterations, 95% when there are 5 alterations, 98% when there are 2 alterations, 99% when there is 1 alteration per hundred, and 99.5% identity when there is 1 alteration per two hundred.

In the art, the term "identity," which refers to a subset of "similarity," is used in connection with the output of various computer programs that compare sequences and seek to align the sequences. For example, Identity can be readily calculated by known methods, including but not limited to those described in books that deal with computer analysis of sequence data. Computational methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403–410 (1990). The BLAST X program is publicly available from NCBI and other sources (BLAST Manual, Altschul, S., et al., NCBI NLM NIH Bethesda, Md. 20894; Altschul, S., et al., *J. Mol. Biol.* 215: 403–410 (1990). The well known Smith Waterman algorithm can also be used to determine identity. Variant(s) as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant can or can not alter the amino acid sequence of a polypeptide encoded by the reference polynucleotide. Nucleotide changes can result in amino acid substitutions, additions, deletions, fusion proteins and truncations in the polypeptide encoded by the reference sequence, (for example, SEQ ID NO: 1 or 3). A typical variant of a polypeptide differs in amino acid sequence from another, reference polypeptide. Generally, differences are limited so that the sequences of the reference polypeptide and the variant are closely similar overall and, in many regions, identical. A variant and reference polypeptide can differ in amino acid sequence by one or more substitutions, additions, deletions in any combination. A substituted or inserted amino acid residue can or can not be one encoded by the genetic code. The present invention also includes include variants of each of the polypeptides of the invention, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Such conservative mutations include mutations that switch one amino acid for another within a group. (For example, within one of the following groups: Small aliphatic, nonpolar or slightly polar residues: Ala, Ser, Thr, Pro and Gly; or Polar, negatively charged residues and their amides: Asp, Asn, Glu and Gln; or Polar, positively charged residues: His, Arg and Lys). Particularly preferred are variants in which several, e.g., 5–10, 1–5, 1–3,1–2 or 1 amino acid(s) are substituted, deleted, or added in any combination. A variant of a polynucleotide or polypeptide can be a naturally occurring such as an allelic variant, or it can be a variant that is not known to occur naturally. Non-naturally occurring variants of polynucleotides and polypeptides can be made by mutagenesis techniques, by direct synthesis, and by other recombinant methods known to skilled artisans.

Another aspect of the invention relates to isolated polynucleotides, including at least one full length gene, that encodes a Tpl2 polypeptide having a deduced amino acid sequence of (SEQ ID NO: 2 or 4) and polynucleotides closely related thereto and variants thereof.

The term "polynucleotide encoding a polypeptide" as used herein encompasses polynucleotides that include a sequence encoding a Tpl2 polypeptide, having an amino acid sequence set out in (SEQ ID NO: 2 or 4). The term also encompasses polynucleotidesthat include a single continuous region or discontinuous regions encoding the polypeptide (for example, polynucleotides interrupted by integrated phage, an integrated insertion sequence, an integrated selectable marker sequence, an integrated vector sequence, an integrated transposon sequence, or due to RNA editing or genomic DNA reorganization) together with additional regions, that also may comprise coding and/or non-coding sequences.

Further particularly preferred embodiments are polynucleotides encoding Cot Clone (human Tpl2) variants, that have the amino acid sequence of Cot Clone polypeptide of (SEQ ID NO: 2) in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of Tpl2 polypeptide.

Preferred isolated Cot Clone polynucleotide (SEQ ID NO: 1) embodiments also include polynucleotide fragments, such as a polynucleotide having a nuclic acid sequence having at least 15, 20, 30, 40, 50 or 100 contiguous nucleic acids from the polynucleotide sequence of SEQ ID NO: 1, or a polynucleotide comprising a nucleic acid sequence having at least 15, 20, 30, 40, 50 or 100 contiguous nucleic acids truncated or deleted from the 5' and/or 3' end of the polynucleotide sequence of SEQ ID NO: 1.

Further preferred embodiments of the invention are polynucleotides that are at least 95% or 97% identical over their entire length to a polynucleotide encoding Tpl2 polypeptide having an amino acid sequence set out in SEQ ID NO: 2 or 4, and polynucleotides that are complementary to such polynucleotides. Furthermore, those with at least 97% are highly preferred among those with at least 95%, and among these those with at least 98% and at least 99% are particularly highly preferred, with at least 99% being the most preferred.

Preferred embodiments are polynucleotides encoding polypeptides that retain substantially the same biological function or activity as a mature polypeptide encoded by a DNA of SEQ ID NO: 1 or 3. For each and every polynucleotide of the invention there is provided a polynucleotide complementary to it. It is preferred that these complementary polynucleotides are fully complementary to each polynucleotide with which they are complementary. A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

As will be recognized, the entire polypeptide encoded by an open reading frame is often not required for activity. Accordingly, it has become routine in molecular biology to map the boundaries of the primary structure required for activity with N-terminal and C-terminal deletion experiments. These experiments utilize exonuclease digestion or convenient restriction sites to cleave coding nucleic acid sequence. For example, Promega (Madison, Wis.) sell an Erase-a-base™ system that uses Exonuclease III designed to facilitate analysis of the deletion products (protocol available at www.promega.com). The digested endpoints can be repaired (e.g., by ligation to synthetic linkers) to the extent necessary to preserve an open reading frame. In this way, the nucleic acid of SEQ ID NO: 1 or 3 readily provides contiguous fragments of SEQ ID NO: 1 or 3 sufficient to provide an activity, such as an enzymatic, binding or antibody-inducing activity. Nucleic acid sequences encoding such fragments of SEQ ID NO: 1 or 3 and variants thereof as described herein are within the invention, as are polypeptides so encoded. Contemplated also are Tpl2 protein or the fragment thereof encoded by SEQ ID NO: 1 or 3 or their variants which protein or the fragment thereof generates antibodies having binding specifically for the Tpl2 protein.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, that is a precursor to a proprotein, having a leader sequence and one or more prosequences, that generally are removed during processing steps that produce active and mature forms of the polypeptide.

Polypeptides and polynucleotides of the invention may also be used to assess the binding of small molecule substrates and ligands in, for example, cells, cell-free preparations, chemical libraries, and natural product mixtures.

Polypeptides and polynucleotides of the present invention are responsible for many biological functions, including many inflammatory disease states, in particular the diseases herein mentioned in the previous paragraph. It is therefore desirable to devise screening methods to identify compounds that agonize (e.g., stimulate) or that antagonize (e.g., inhibit) the function of the Tpl2 polypeptide or polynucleotide. Accordingly, in a further aspect, the present invention provides for a method of screening compounds to identify those that agonize or that antagonize the function of the Tpl2 polypeptide or polynucleotide of the invention. In general, agonists or antagonists (e.g., inhibitors) may be employed for therapeutic purposes for such diseases as mentioned above. Compounds may be identified from a variety of sources, for example, cells, cell-free preparations, chemical libraries, and natural product mixtures. Such agonists and antagonists so-identified may be natural or modified substrates, ligands, enzymes, etc., as the case may be, Tpl2 polypeptides and polynucleotides.

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Further, the screening methods may simply include the steps of mixing a candidate compound with a solution comprising a polypeptide or polynucleotide of the present invention, to form a mixture, measuring Tpl2 polypeptide and/or polynucleotide activity in the mixture, and comparing the Tpl2 polypeptide and/or polynucleotide activity of the mixture to a standard.

The invention also provides a method of screening compounds to identify those that enhance (agonist) or block (antagonist) the action of Tpl2 polypeptides or polynucleotides. Particularly provided herein are methods for screening for those compounds that are antiinflammatory. The method of screening may involve high-throughputtechniques. For example, to screen for agonists or antagonists, a synthetic reaction mix, a cellular compartment, such as a membrane, a cell, or an organism having Tpl2 polypeptide and a labeled substrate or ligand of such polypeptide is incubated in the absence or the presence of a candidate molecule that may be a Tpl2 agonist or antagonist. The ability of the candidate molecule to agonize or antagonize the Tpl2 polypeptide is reflected in decreased binding of the labeled ligand or decreased production of product from such substrate. Molecules that bind gratuitously, i.e., without inducing the effects of Tpl2 polypeptide are most likely to be good antagonists. Molecules that bind well and, as the case may be, increase the rate of product production from substrate, increase signal transduction, or increase chemical channel activity are agonists. Detection of the rate or level of enzymatic activity of Tpl2, as the case may be, production of product from substrate, signal transduction, or chemical channel activity may be enhanced by using a reporter system. Reporter systems that may be useful in this regard include but are not limited to calorimetric, labeled substrate converted into product, a reporter gene that is responsive to changes in Tpl2 polynucleotide or polypeptide activity, and binding assays known in the art.

In other embodiments of the invention there are provided methods for identifying compounds or agents that bind to or otherwise interact with and inhibit or activate an activity or expression of Tpl2 polypeptide and/or polynucleotide of the invention. This includes contacting a polypeptide and/or polynucleotide of the invention with a compound to be screened under conditions to permit binding to or other interaction between the compound and the polypeptide and/or polynucleotide to assess the binding to or other interaction with the compound, such binding or interaction preferably being associated with a second component capable of providing a detectable signal in response to the binding or interaction of the polypeptide and/or polynucleotide with the compound; and determining whether the compound binds to or otherwise interacts with and activates or inhibits an activity or expression of the Tpl2 polypeptide and/or polynucleotide by detecting the presence or absence of a signal generated from the binding or interaction of the compound with the polypeptide and/or polynucleotide.

Tpl2 polypeptide and/or polynucleotide of the present invention may also be used in a method for the structure-based design of an agonist or antagonist of the polypeptide and/or polynucleotide. This way requires the determination in the first instance of the three-dimensional structure of the polypeptide and/or polynucleotide, or complexes thereof; next to deduce the three-dimensional structure for the likely reactive site(s), binding site(s) or motif(s) of an agonist or antagonist; and synthesizing candidate compounds that are predicted to bind to or react with the deduced binding site(s), reactive site(s), and/or motif(s); and (d) testing whether the candidate compounds are indeed agonists or antagonists.

It will be further appreciated that this will normally be an iterative process, and this iterative process may be performed using automated and computer-controlled steps. In a further aspect, the present invention provides methods of treating abnormal conditions such as, for instance, a Disease, related to either an excess of, an under-expression of, an elevated activity of, or a decreased activity of Tpl2 polypeptide and/or polynucleotide.

If the expression and/or activity of the polypeptide and/or polynucleotide is in excess, several approaches are available. One approach comprises administering to an individual in need thereof an inhibitor compound (antagonist) as herein described, optionally in combination with a pharmaceutically acceptable carrier, in an amount effective to inhibit the function and/or expression of the polypeptide and/or polynucleotide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide and/or polynucleotide may be administered. Typical examples of such competitors include fragments of the Tpl2 polypeptide and/or polypeptide.

In still another approach, expression of the gene encoding endogenous Tpl2 polypeptide can be inhibited using expression blocking techniques. This blocking may be targeted against any step in gene expression, but is preferably targeted against transcription and/or translation. An examples of a known technique of this sort involve the use of antisense sequences. (See, for example, O'Connor, *J Neurochem* (1991) 56:560 in Oligodeoxynucleotides as Antisense Inhibitors of Gene Expression, CRC Press, Boca Raton, Fla. (1988)). Alternatively, oligonucleotides that form triple helices with the gene can be supplied (see, for example, Lee et al., *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo.

In animals, the induction of TNFα can be due to LPS as described above or due to other microbial or biological molecules, and/or pharmacological molecules, thereby resulting in, among other things, various inflammatory diseases including arthritis. Therefore, one alternative approach can be to inhibit the production of TNFα in cells; another approach can be to inhibit the transduction of TNFα signals to address the problem of inflammatory diseases. Thus, in another aspect of the invention, methods and compositions for the treatment or prevention of TNFα-mediated inflammatory diseases are provided.

Thus, the polynucleotide sequences provided herein may be used in the discovery and development of anti endotoxin shock and/or anti inflammatory compounds. The encoded protein, upon expression, can be used, for example, as a target for the screening of antiinflammatory drugs.

EXAMPLES

The following examples further illustrate the present invention, but of course. Should not be constructed as in any way limiting its scope. The examples below are carried out using standard techniques, that are well known and routine to those of skill in the art, except where otherwise described in detail. The examples are illustrative, but do not limit the invention. All animal methods of treatment or prevention described herein are preferably applied to mammals, most preferably to humans.

Example 1

Generation and Establishment of Tpl-2 −/− Mice

A) Construction of Tpl2 targeting construct and generation of Tpl2 −/− mice. To generate the Tpl2 targeting construct, Tpl2 was cloned from a 129/SV genomic library (Stratagene). Shown in FIG. 1A is a schematic representation of a method for the construction of the Tpl2 targeting construct. The upper panel in FIG. 1A shows the restriction map of a Tpl2 genomic clone isolated from a 129 mouse genomic DNA library. The code for the restriction enzymes in the map is as follows: B, BamHI, C-ClaI, H-HindIII, N-NheI, R-EcoRI, S-SacI, Sa-SalI, Sp-SphI, X-XbaI. The boxed BamHI-BamHI DNA fragment includes the sequences BamHI-ClaI and NheI-BamHI which were cloned into the targeting vector 5' and 3' of the G418 resistance gene respectively, and the Tpl2 sequences that were replaced by the G418 resistance cassete via homologous recombination. The lower panel in FIG. 1A shows the structure of the Tpl2 targeting construct.

Thus, the construct was designed to contain genomic sequences upstream of exon 3 and downstream of exon 5, 5' and 3' of the G418-resistance gene respectively (FIG. 1A). Homologous recombination between the electroporated construct and the endogenous Tpl2 gene, replaced the Tpl2 sequences between exons 3 and 5 with the G418 resistance cassette. One of the resulting mutant ES cell clones was injected into blastocysts derived from C57Bl/6J mice. The resulting chimeras were mated to C57Bl/6J mice and the Tpl2−/+ mice, derived from this cross, were backcrossed to C57Bl/6J for nine generations. Mice utilized in the experiments presented here were obtained by brother-sister mating of Tpl2 −/− and Tpl2 +/+animals.

B) Establishment of Tpl2 −/− mice. Mice were genotyped for their Tpl2 status by hybridizing Southern blots of SphI-digested DNA with probes 1 and 2. Expression of Tpl2 was measured in spleen by Northern blotting and in spleen liver and thymus by Western blotting. Western blots were probed with a rabbit polyclonal antibody against Tpl2 (Transduction Labs).

TNFα ΔARE/− mice are double heterozygotes for two TNFα mutations: one that deleted the ARE element in the 3'UTR of the TNFα mRNA (ΔARE) (See Kontoyiannis et al., 1999, Immunity. 10, 387–398) and a second one that inactivated the other TNFα allele (−) (See Kontoyiannis et al., 1999, Immunity. 10, 387–398). These mice were crossed to ninth generation Tpl2 −/− mice to generate TNFα ΔARE/+, Tpl2 +/− and TNFα −/+, Tpl2 +/− F1 animals. Mice of these two genotypes were crossed to each other to generate TNFα ΔARE/−, Tpl2 +/+ and TNFα ΔARE/−, Tpl2 −/− double mutant mice. NF-κB1 −/− mice (See Sha et al., 1995, Infect. Immun. 23, 287–293) were purchased from the Jackson Labs. Shown in FIG. 1B shows the results of screening for homologous recombination between the vector and the endogenous Tpl2 gene. ES cell genomic was digested with SphI and following electrophoresis and transfer it was hybridized to the probes 1 and 2 shown in A. The bands detected with probes 1 and 2 were approximately 11 kb and 5 kb respectively. Shown in FIG. C1 is the Northern blotting analysis of poly-A+ mRNA extracted from spleens of Tpl-2 −/−, Tpl-2 +/− and Tpl-2 +/+ mice. The blot was hybridized to a 1.5 kb PstI-PstI fragment retrieved from the Tpl2 cDNA (See Ceci et al, 1997, Genes Dev. 11, 688–700). Equal loading was confirmed by hybridizing the same blot to a GAPDH probe. The analysis shows that Tpl-2 −/− mice do not express Tpl-2. Western blot analysis of spleen, liver and thymus extracts from Tpl2 +/+and Tpl2 −/− mice is illustrated in FIG. C2. The blot was probed with the anti-Tpl2 antibody from Transduction Labs. The arrow on the left shows a band that is detected only in tissues from wild type animals and exhibits the elecrophoretic mobility of Tpl2.

To determine whether the inactivation of Tpl2 gave rise to histologically identifiable defects, paraffin sections of all organs of adult Tpl2 −/− mice, including thymus spleen and lymph nodes, were stained with hematoxyllin and eosin and they were examined by light microscopy. All three lymphoid organs exhibit normal histology.

To identify potential shifts in cell populations in the thymus and spleen of Tpl2 −/− mice, thymocytes and splenocytes were stained with antibodies against CD4, CD8, Thy2, B220, Mac-1, Ter-1, CD3, IL-2Rα, TCRαβ and TCRγδ (Pharmingen). The percentage of cells staining with different antibody combinations and the intensity of staining were determined by flow-cytometry.

To measure T cell-dependent and T cell-independent antibody responses Tpl2 −/− mice and Tpl2 +/+ controls were inoculated IP with 100 µg KLH (Sigma) in complete Freund adjuvant or 50 µg LPS-TNP (See Skelly et al, 1979, Infect. Immun. 23, 287–293) respectively. The former group of mice were inoculated twice, 4 weeks apart, to measure primary and secondary antibody responses while the latter group was inoculated once. All mice were bled weekly following the injection. Antibody titers were measured in serum using an ELISA procedure developed and optimized by us. In short, polystirene plates were coated with BSA-TNP (See Mäkelä et al, 1986, Haptens and carriers. In Handbook of experimental immunology, D. M. Weir, ed. (Oxford: Blackwell Scientific), p. 3.1–3.13.) and serum dilutions were added to the plates. Following overnight incubation at 4° C., serum was removed and the wells were extensively washed with PBS containing 0.1% Tween-20. Bound antibodies were detected with isotype specific biotinylated goat anti mouse antibodies from Southern Biotechnology Associates (Birmingham, AL). Cell-mediated cytotoxicity was measured in lymphocytic choriomeningitis virus (LCM)-infected mice as described (See Evans et al., 1993, J Immunol. 151, 6259–6264.). Proliferation of spleen cells following stimulation with 4 µg/ml Concanavallin A (Con A) (Sigma) or 1 µg/ml LPS (L6011-Sigma) was measured by $^3$H-thymidine incorporation (See Fernandez et al, 1995, Methods in Cellular Immunology. (Boca Raton: CRC Press), pp. 47–49). Induction of IL-2, IL-4 and INFγ in unfractionated splenocytes stimulated with anti-CD3 plus anti-CD28 antibodies (See Walter et al., 1994, Eur. Cytokine Netw. 5, 13–21.) was measured in culture supernatants by ELISA (BioSource) according to the manufacturer's protocol.

Example 2

Demonstration of the Resistance of Tpl-2 −/− Mice to LPS/D-galactosamine-induced Endotoxin Shock and Sensitivity of Tpl-2 −/− Mice to TNFα-induced Toxicity Eight to twelve week old Tpl2 −/−, NF-κB1 −/− and control mice of both sexes were inoculated IP with 1 mg/g body weight D-galactosamine (Sigma) (250 mg/ml in PBS) and with 0.1, 1 or 10 µg lipopolysaccharide (LPS) derived from *Salmonella enteritidis* (Sigma) (10, 100 or 1000 µg/ml solution in PBS). The syndrome arising from this treatment culminated in death at six to nine hours. In separate identical experiments the mice were bled at 30 minutes, and 1 hour after treatment and the concentration of TNFα was measured in the serum by ELISA. The concentration of IL1β was measured also by ELISA at 2 hours after treatment.

Eight to twelve week old mice of both sexes were also used for TNFα toxicity studies. These mice were inoculated IP with 1 mg/g body weight D-galactosamine. One hour later they were inoculated IV with 35 ng/g body weight TNFα (Endogen, Woburn, Mass.) and they were placed under observation.

FIG. 2A demonstrates that LPS-induced TNF-α secretion is impaired in Tpl2 −/− mice. To demonstrate this Tpl2 −/− and Tpl2 +/+ mice were injected IP with D-galactosamine and LPS from *Salmonella enteritidis*. Half an hour and 1 hour later sera samples were collected from the tail vein. TNFα levels were determined by ELISA (Pharmingen). Data are shown as mean value±standard deviation. FIG. 2B demonstrates that Tpl2 −/− mice are sensitive to TNFα-induced toxicity. Six Tpl2 +/+ mice and 10 Tpl2 −/− mice (8 to 12 weeks old) were injected with D-Galactosamine IP and one hour later with 35 ng/g body weight murine TNFα IV. Time of death was recorded starting from the time of injection of TNFα. These results presented in FIG. 2 showed that the resistance of Tpl2 −/− mice to LPS/D-Galactosmine induced endotoxin shock is due to a defect in TNFα secretion in response to LPS.

Example 3

LPS Treatments and TNFα Production in Splenocytes, TEPM and BMDM from Tpl2 −/− Mice and Tpl2 +/+ Mice (or wt Mice)

Results presented in FIG. 3 show that plenocytes, TEPM and BMDM from Tpl2 −/− mice are defective in TNFα production in response to LPS. Status of the high affinity LPS receptor.

Unfractionated splenocytes were distributed in 96 well plates (5×10$^5$ cells/well in 200 µl). The cells were treated with LPS from *Salmonella enteritidis* at the concentrations shown in the figure (FIG. 3A Left Panel). Alternatively, the cells were exposed to anti-CD3 plus anti-CD28 antibodies. Supernatants were collected after 24h of incubation and the TNFα titers were measured by ELISA. Unfractionated splenocytes were stimulated with 1 µg/ml LPS. 24 hours later they were pulsed with $^3$H-thymidine (0.1 µCi/well) (FIG. 3A Right Panel).

TEPM and BMDM from three Tpl2 +/+ and three Tpl2 −/− mice were distributed into 24 well plates (10$^6$ cells/ml). Attached cells were washed twice with DMEM supplemented with 0.5% FBS and they were cultured in the same medium overnight. Sixteen hours later they were placed back into 10% FBS containing medium with or without LPS (1 µg/ml final concentration). Culture supernatants were collected at different time points and the amount of secreted TNFα was measured by ELISA assay (OptEIA TNFα kit, Pharmingen) in both the LPS-treated and untreated samples. To control for the cell number, the cells were incubated at the end of the experiment with 0.33% neutral red in DMEM supplemented with 10% FBS. Following this, for 30 minutes at 37° C., they were washed with PBS and were lysed with 0.5% SDS. Neutral red absorption at 550 nm was measured in a spectrophotometer and it was used to normalize the TNFα levels across wells. For results, see FIG. 3B Left and middle panels.

TEPM from Tpl2 +/+ and Tpl2 −/− mice were incubated for 6 hours with LPS (1 µg/ml) and with monensin (2 µM) (GolgiStop, Pharmingen). Following harvest by scraping, the cells were washed and permeabilized with 0.1% saponin. Permeabilized cells were stained for intracellular TNFα with a FITC labeled anti-TNFα antibody from Pharmingen. For results, see FIG. 3B, Right panel.

TEPM recovered by washing the peritoneal cavity of thioglycollate-treated mice with cold HBSS were stained with anti-Mac-1 antibody from Pharmingen which recognizes a molecule specifically expressed in macrophages and with anti-CD14 (Pharmingen). Stained cells were identified by flow-cytometry. For results, see FIG. 3C.

Example 4

Induction of TNFα mRNA by LPS in vivo and in Culture

Figure 4:
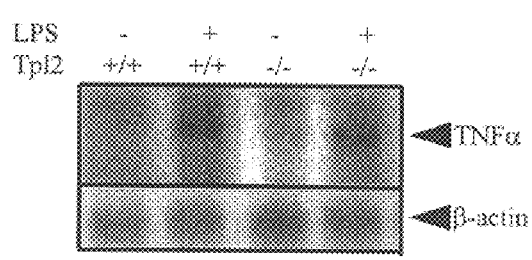
FIG. 4 shows induction of TNFα mRNA by LPS in vivo and in culture.
Figure 4:
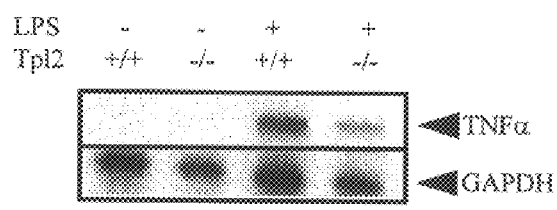
Figure 4:
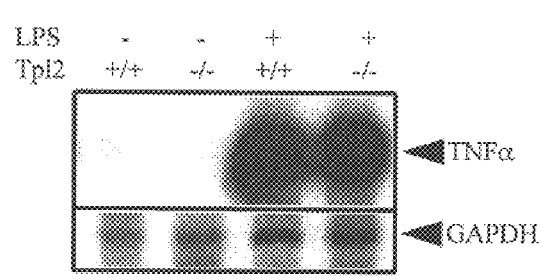
Figure 4:
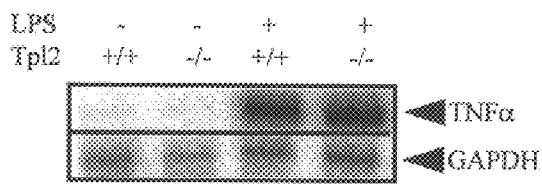

The results presented in FIG. 4 show that the defect in TNFα induction in response to LPS in Tpl2 −/− mice is posttranscriptional. Tpl2 +/+ and Tpl2 −/− mice were inoculated with D-Galactosamine and LPS and were sacrificed 1 hour later. Twelve µg of total spleen RNA from LPS-injected and uninjected control mice were Northern blotted and hybridized to TNFα and β-actin cDNA probes. Hybridization was visualized by autoradiography and quantitated by Phospholmager scanning. See FIG. 4A1. The levels of TNFα mRNA in the same spleen RNA samples was determined by RNase protection. GAPDH was used as a loading control. See FIG. 4A2

Shown in FIGS. 4B and C are TNFα mRNA levels in TEPM (C) and BMDM (D) as determined by RNase protection. GAPDH was used as a loading control. All cells were cultured in DMEM supplemented with 0.5% FBS overnight prior to their exposure to LPS.

Example 5

Activation of the ERK Pathway by LPS in Both TEPM and BMDM in Culture

Figure 5:
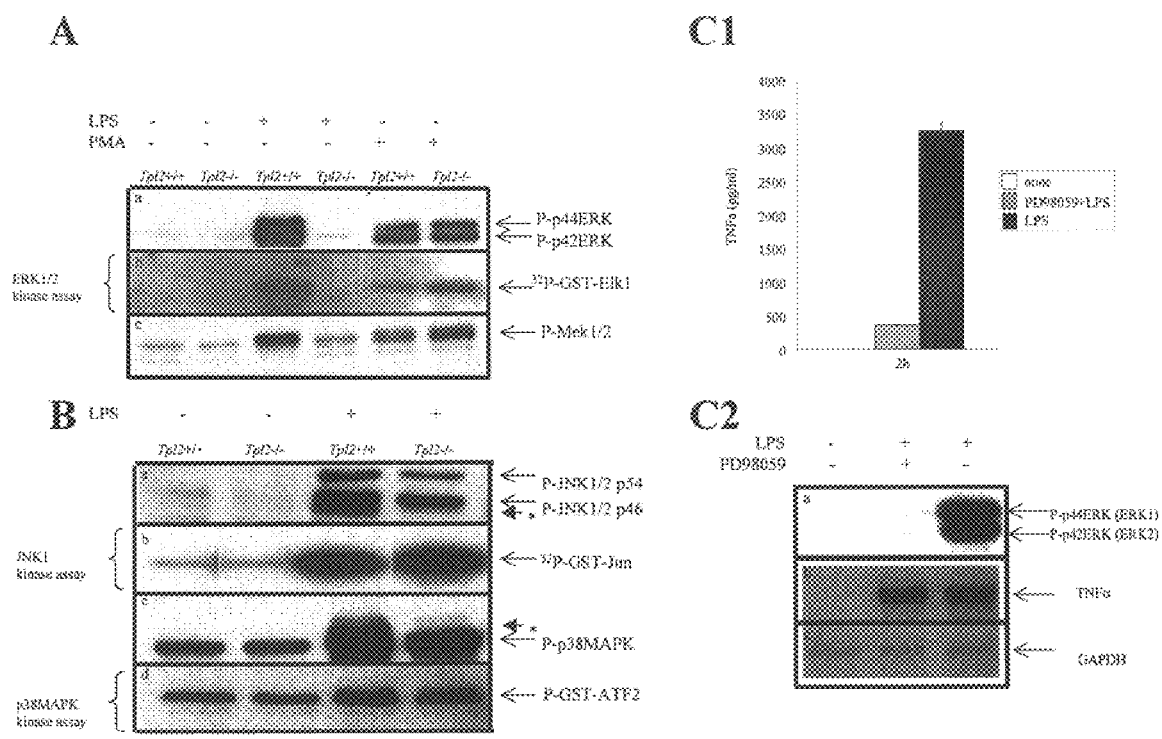
FIG. 5 shows activation of the ERK pathway by LPS in both TEPM and BMDM in culture.

Presented in FIG. 5 are the results to show that Tpl2 is required for the activation of the ERK pathway by LPS in both TEPM and BMDM in culture and activation of the ERK pathway is required for the induction of TNFα by LPS.

Western blots of LPS or PMA-stimulated and unstimulated rested TEPM were probed with antibodies against phospho ERK1, and phospho ERK2 (see FIG. 5A, panel a) or phopho MEK1 and phospho MEK2 (see FIG. 5A, panel c). Probing the same extracts with antibodies against total ERK1, ERK2, MEK1 and MEK2 revealed that expression of these kinases was equal in all samples (data not shown). ERK1 and ERK2 immunoprecipitates from the same cell samples were used for in vitro kinase assays. The substrate was GST-Elk1 (see FIG. 5A, panel b).

Western blots of LPS-stimulated and unstimulated rested TEPM were probed with antibodies against phospho JNK1 and phospho JNK2 (see FIG. 5B, panel a) or phospho p38MAPK (see FIG. 5B, panel c). The result show that all these kinases undergo phosphrylation in response to LPS in both the Tpl2 +/+ ant the Tpl2 –/– macrophages. Arrows marked by asterisks indicate cross reacting phosphorylated ERK bands (data not shown).

JNK1 (FIG. 5B, panel b) and JNK2 (data not shown) as well as p38MAPK (FIG. 5B, panel d) immunoprecipitates were used for in vitro kinase assays. The substrates were GST-Jun (for JNK) and GST-ATF2 (for p38MAPK). The p38MAPK kinase reaction was carried out with cold ATP. Phosphorylation of the substrate was detected by probing a Western blot of the product of the kinase reaction with an antibody against phospho-ATF2 from NEB.

For results shown in FIG. 5C1, PD98059-treated and untreated rested TEPM from Tpl2 +/+ mice were exposed to LPS. TNFα induction was measured by ELISA in culture supernatants harvested two hours later.

For results shown in FIG. 5C2, panel a, TEPM cultures parallel to the TEPM cultures in C1 were harvested at 30 minutes after exposure to LPS. A Western blot of the harvested lysates was probed with the anti-phospho-ERK1/phospho-ERK2 antibody used in panel Aa. The result shows that PD98059 blocks ERK activation. For results shown in Panels b and c total RNA from the same cells was used in a TNFα RNase protection assay. The result shows that PD98059 did not inhibit the induction of TNFα mRNA by LPS. Results similar to the ones shown in panels A, B and C1 and C2 were obtained also with BMDM cultures.

Example 6

Tpl2 and LPS-induced Activation of NF-κB

Presented in FIG. 6 are the results to show that Tpl2 is not required for LPS-induced activation of NF-κB and NF-κB1

–/– mice are sensitive to LPS/D-galactosamine induced endotoxin shock. EMSA of nuclear extracts of LPS-stimulated and unstimulated TEPM from Tpl2 +/+ and Tpl2 –/– mice incubated with a labeled double stranded oligonucleotide corresponding to the NF-κB binding site (FIG. 6A). For results shown in FIG. 6B, Ten NF-κB1 –/– mice (8–12 weeks old) and 10 wild type mice were inoculated with LPS and D-Galactosamine. The curves show percent survival at various time points up to 9 hour post inoculation.

Example 7

The Effect of Tpl2 on the Induction of TNFα by LPS and Influence of the AU-rich Element in the 3'UTR of the TNFα mRNA Shown in FIG. 7 are the results which demonstrate that the effect of Tpl2 on the induction of TNFα by LPS is influenced by the AU-rich element in the 3'UTR of the TNFα mRNA. BMDM from TNFα ΔARE/– Tpl2 –/– and TNFα ΔARE/– Tpl2 +/+ mice were stimulated with LPS. TNFα secretion in culture supernatants was measured by ELISA at the indicated time points. BMDM from Tpl2 +/+ and Tpl2 –/– as well as from TNFα +/– Tpl2 –/– and TNFα +/– Tpl2 +/+ mice were used as controls. BMDM from mice of both TNFα ΔARE/–, Tpl2 +/+ and TNFα ΔARE/– Tpl2 –/– genotypes express high basal levels of TNFα and exhibit similar levels of TNFα induction in response to LPS.

The following are the details of the procedures applicable to one or more of the above Examples.

The details on cell culture are as follows. Single cell suspensions of splenocytes were placed in ACK hypotonic buffer (0.15M $NH_4Cl$, 1 mM $KHCO_3$, 0.1M EDTA) (See Kruisbeek, 1993, Isolation and fractionation of mononuclear cell populations. Section I. Unit 3.1. In Current Protocols in Immunology, J. E. Coligan, A. M. Kruisbeek, D. H. Margulies, E. M. Shevach, and W. Strober, eds. (New York: John Wiley & Sons), p. 3.1.1–3.1.5) to lyse the red blood cells. Subsequently, they were washed twice in RPMI (BRL-Gibco), supplemented with non-essential amino acids (100 μM), β-mercaptoethanol (50 mM), penicillin (100 U/ml), streptomycin (100 μg/ml) and fetal bovine serum (FBS) (10%). Following this, they were cultured in the same medium.

To culture thioglycolate-elicited peritoneal macrophages (TEPM), mice were injected IP with 1.5 ml thioglycolate broth (Sigma). Four days later, the mice were sacrificed and their peritoneal cavities were washed three times with 5 ml of cold Hanks balanced salt solution (HBSS) (Gibco). Cell pellets were washed once with DMEM supplemented with 10% FBS and they were cultured at the concentration of $10^6$ cells/ml. Two hours later the dishes were washed with 10 ml of medium to remove non-adherent cells. At least 95% of the remaining adherent cells were macrophages (data not shown). Prior to LPS or PMA stimulation, TEPM were cultured overnight in DMEM supplemented with only 0.5% FBS.

Bone marrow-derived macrophages (BMDM) were isolated and cultured as described (See Warren et al., 1985, Annu. Rev. Immunol. 4, 369–388). In short, the bone marrow was flushed from femurs of wild type and mutant mice with 5 ml of DMEM supplemented with 10% FBS. Cell pellets were resuspended in ACK hypotonic buffer, to remove red blood cells, and were subsequently washed with DMEM with 10% FBS and cultured at the concentration of $10^7$ cells/ml in DMEM supplemented with 20% FBS and 30% L929 cell conditioned media (CSF-1 source) (See Warren et al., 1985, Annu. Rev. Immunol. 4, 369–388) in bacteriological Petri dishes. Six days later, adherent macrophages were trypsinized, counted and replated to be used experimentally. Prior to LPS or PMA stimulation BMDM were cultured overnight in DMEM supplemented with only 0.5% FBS.

To measure TNFα in culture supernatants of splenocytes or macrophages or in sera, we used an ELISA kit from Pharmingen (OptEIA TNFα kit). As a first step, polystyrene plates were coated with an anti-TNFα capture antibody provided with the kit. $2 \times 10^5$ splenocytes were cultured in 0.2 ml media in 96 well plates and $10^6$ TEPM or BMDM were cultured in 1 ml of media in 24 well plates. Following stimulation with LPS (splenocytes and macrophages) or anti-CD3 plus anti-CD28 (splenocytes) culture supernatants were collected at various time points post stimulation. Serial dilutions of the culture supernatants (1/1–1/50) or the serum (1/4–1/100) were transferred into antibody coated microtiter wells and they were incubated at 4° C. overnight. Following this, the wells were washed 3 with PBS containing 0.1% Tween-20. TNFα-anti-TNFα complexes coating the wells were incubated with biotinylated anti TNFα detection antibody and horseradish peroxidase-conjugated straptavidin. Following three additional washes with PBS-Tween 20, antigen-antibody complexes were detected by incubation with 50 μl 3,3',5,5'-tetramethylbenzidine (Sigma) substrate. TNFα concentration was determined by measuring absorption at 450 nm. Experimental absorption values were translated into TNFα concentration by placing them on a standard curve that plots absorption versus TNFα concentration. IL-1β, IL-2, IL-4 and IFNγ were measured using similar ELISA kits purchased from Biosource (Camarillo, Calif.).

Intracellular TNFα was measured in macrophages stimulated with 1 mg/ml LPS from *Salmonella enteritidis* for 6 hours. To inhibit transport to the plasma membrane and cleavage and release of TNFα, cells were treated with 2 μM of monensin (GolgiStop, Pharmingen). Prior to staining, cells were scraped from the Petri dish and washed in PBS supplemented with 5% calf serum. Subsequently they were permeabilized by resuspending them in PBS containing 5% calf serum and 0.1% (w/v) saponin (Sigma). Intracellular TNFα was stained by incubating the permeabilized cells with anti-TNFα FITC-labeled antibody from Pharmingen (A6088) (1.2 μg/ml final concentration, for 30 minutes on ice). Following washing with PBS containing 5% calf serum stained cells were identified by flow cytometry. Other antibodies used for flow cytometry were purchased from Pharmingen.

For Northern bloting and RNase protection assays, RNA was extracted from spleens of mice treated with LPS and D-Galactosamine or from LPS-stimulated cultured peritoneal and bone-marrow-derived macrophages using the method of Chomczynski (See Chomczynski, 1993, Biotechniques 15, 532–537). In short, cells were lysed in buffer containing guanindinium thiocyanate and the RNA was extracted from the lysates with acid phenol. Total RNA (12 μg) was subjected to electrophoresis in denaturing formaldehyde gels. Following this, the RNA was transferred to nylon membranes (MagnaGraph from MSI/Osmonics) and it was hybrydized to cDNA probes for TNFα and mouse actin (loading control). The probes were obtained by RT-PCR from LPS-stimulated RAW264.7 RNA using gene specific primers (5'-GCCCAGACCCTCACACTCAG-3' (SEQ ID NO:5) and 5'-AACACCCATTCCCTTCACAG-3' (SEQ ID NO:6) for TNFα; 5'-GTGGGCCGCTCTAGGCACCAA-3' (SEQ D NO:7) and 5'-CTCTTTGATGTCACGCACGATTTC-3' (SEQ ID NO:8) for mouse actin) (Morgan et al., (1993), Science 278, 1612–1615). RNase protection was carried out with 2 μg of total RNA from spleen cells and peritoneal or bone marrow macrophages using an RNase protection assay kit (Pharmingen, San Diego, Calif.) and following the manufacturer's instructions. The RNA/RNA hybrid complexes remaining after digestion of the nonhybridizing RNA with RNaseA and RNaseT1 were separated in 6% denaturing sequencing gels. Radioactivity in individual bands in both the Northern blots and the RNase protection experiments was measured Molecular Dynamics PhosphorImager.

For Western blotting, cells were lysed in SDS sample loading buffer (62.5 mM Tris-HCl, pH6.8, 2% SDS, 10% glycerol, 50 mM DTT, 0.1% bromphenol blue). Lysates were then subjected to 5 min boiling and ultrasonication. Protein concentration was measured in 1:100 diluted lysates using the Bradford assay (BioRad). Proteins in the extracts were separated by SDS polyacrylamide gel electrophoresis (50 μg protein/lane). Following electrophoresis, proteins were transferred to PVDF nylon membranes. Membranes were then blocked in TBS (Tris-buffered saline) containing 0.1% Tween-20 and 5% milk. Primary antibodies were added in 5% milk (for anti-phospho-ERK1/2 (Thr202/Tyr204) and anti-ERK1/2) or in 5% BSA (for anti-phospho-MEK1/2 (Ser217/221), anti-phospho-p38MAPK (Thr180/Tyr182), anti-phospho-JNK1/2 (Thr183/Tyr185), anti-MEK1/2, anti-p38MAPK and anti-JNK1/2) for a minimum 16 hours at 4° C. All antibodies were rabbit polyclonals and they were purchased form New England Biolabs (Beverly, Mass.). Excess antibodies were washed at room temperature three times for 5 minutes with TBS with 0.1% Tween-20. Washed membranes were incubated at room temperature for 1 hour with goat anti-rabbit antiserum conjugated with horseradish peroxidase. Excess antiserum was again washed three times with TBS-Tween for 5 minute at room temperature. Antigen-antibody complexes on the membranes were detected by chemiluminescence.

For in vitro kinase assays, cells were lysed in Triton-X-100 lysis buffer (20 mM Tris-HCl, pH 7.5, 150 mM NaCl, 1 mM EDTA, 1 mM EGTA, 1% Triton X-100, 2.5 mM Na pyrophosphate, 1 mM β-glycerophosphate, 1 mM $Na_3VO_4$, 1 mg/ml leupeptin, 1 mM PMSF). Protein quantitation was carried out using the Bradford assay (Biorad). ERK1/ERK2, JNK1 and JNK2 were immunoprecipitated from 100 μg of cellular extracts using antibodies from SantaCruz (ERK1/2, JNK1) or Upstate Biotechnology (JNK2) and 20 ml of protein A-agarose beads (Gibco). After overnight incubation, the beads were washed twice in lysis buffer and twice in kinase buffer (25 m mM Tris-HCl, pH 7.5, 5 mM β-glycerophosphate, 2 mM DTT, 0.1 mM $Na_3VO_4$, 10 mM $MgCl2$). The washed immunoprecipitates were incubated at 25° C. for 30 minutes with 20 μM ATP, 5 μCi [γ-$^{32}$P]-ATP [3000 mCi/mmol] and 1 μg of purified substrates in kinase buffer. The substrates were GST-Elk1 fusion for ERK1/ERK2 kinase assays) (See Marais et al., 1993, Cell 73, 381–393.) and GST-Jun fusion (for JNK1 and JNK2 kinase assays) (See Derijard et al., 1994, Cell 76, 1025–1037). The p38MAPK assay was carried out using an NEB kit which uses GST-ATF2 substrate. Immunoprecipitation was carried out using an anti phospho-p38MAPK (Thr180/Tyr182) antibody (NEB). The kinase reaction was carried out in the presence of 200 μM cold ATP. Phosphorylation of the GST-ATF2 substrate was detected by Western blotting with an anti-phospho ATF2 (Thr71) specific antibody (NEB).

For electrophoretic mobility shift assays, nuclear extracts of LPS-treated TEPM harvested 60 minutes after LPS treatment were prepared using the NePer kit (Pierce). Cells were harvested by scraping in PBS. Following this, they were pelleted and the pellets were lysed in 200 μl of an NP-40 low salt lysis buffer. Intact nuclei in the cell lysates were pelleted by centrifugation at 12,000×g and they Were lysed in 50 μl of a high-salt buffer. The protein in the final lysates was quantitated using the Bradford assay (Biorad). One μg of nuclear extracts was incubated with $10^5$ cpm of a $^{32}$P-labeled double stranded DNA oligonuclotide probe representing the NF-κB DNA binding site. Incubation was carried out for 30 min on ice in a binding buffer containing 20 mM HEPES (pH7.5), 0.5 mM EDTA, 5 mM MgCl2, 50 mg/ml bovine serum albumin, 0.05% NP-40, 60 mM KCl, 10 mM DTT, 10% glycerol, and 1.5μg of poly(dI/dC). Bound probe was separated from free probe by elecrophoresis in a 6% nondenaturing polyacrylamide gel. Electrophoresis was carried out at 5V/cm for approximately 1.5 hours. The double stranded probe was generated by annealing two complementary oligonucletides (5'-ACAAGGGACTTTCCGCT GGGGACTTTCCAGGG-3' (SEQ ID NO:9) and 5'-CCCTGGAAAGTCCCCAG-3' (SEQ ID NO:10), (Zabel et al., 1991)) and by filling the end using Klenow polymerase and radioactive nucleotides.

Example 8

Tpl2 Dependent Transduction and Inhibition of TNFα Signals

The following Procedures were followed: Recombinant human epidermal growth factor (EGF) was purchased from Gibco/BRL, human or murine tumor necrosis factor-α (TNF-α) and interleukin-1β (IL-1β) were purchased from Genzyme. The monoclonal anti-hemagglutinin tag antibody HA.11 was purchased from BaBco. Rabbit polyclonal antibodies against ERK1 (SC97), JNK1 (SC571), IκB-β (SC945-G), and TRADD (SC1164) were purchased from Santa Cruz Biotechnology. Anti-IκB-α (KD21-5) was kindly provided by Dr. R. Bravo, Bristol-Myers Squibb. Hybridoma cells producing the anti-c-myc tag monoclonal antibody 9E10.2 (Evan, et al., 1985, Molecular & Cellular Biology 5:3610–6) were purchased from ATCC. 9E10.2 monoclonal antibody was purified from ascites induced in SCID mice inoculated intraperitoneally (IP) with hybridoma cells.

For expression constructs, wild-type Tpl-2 and kinase-dead Tpl-2 (Tpl-2K167M) cDNAs were subcloned in the EcoRI site in the polylinker of the retroviral expression vector MSV-SRα (Landau, et al., 1992, Journal of Virology 66:5110–3) or the vector pUHD 10.3 which contains a tetracycline inducible promoter (Gossen, et al., 1992, Proceedings of the National Academy of Sciences of the United States of America 89:5547–51). A hemagglutinin epitope tag (HA) or a c-myc epitope tag (MT) were fused in frame to the carboxy-terminus of the Tpl-2 open reading frame as described (Ceci, et al., 1997, Genes & Development 11:688–700; Patriotis, et al., 1994, Proc. Natl. Acad. Sci. USA 91:9755–9).

For cell culture, COS-1, 293 and REF52 cells were maintained in Dulbecco's modified Eagle's medium (DMEM), (Gibco/BRL) supplemented with 10% fetal bovine serum (FBS) (Gibco/BRL) and PSK [penicillin (50 U/ml), streptomycin (50 μg/ml) and kanamycin (100 μg/ml)]. NIH3T3 cells were maintained in DMEM supplemented with 10% calf serum (CS) (Gibco/BRL), and PSK. COS-1 cells were transiently transfected as previously described (Patriotis, et al., 1994, Proc. Natl. Acad. Sci. USA 91:9755–9), using the DEAE-dextran/Chloroquine method (McCutchan, et al., 1968, Journal of the National Cancer Institute 41:351–7). Briefly, ~3.5×$10^5$ cells were seeded in 60 mm petri dishes and, forty-eight hours later, they were transfected with 6 μg of DNA (2 μg each of the expression constructs supplemented with vector DNA to a final total of 6 μg). 293 cells were transiently transfected using Lipofectamin (Gibco/BRL) according to the instructions provided by the manufacturer. Twenty-four hours later the transfected cells were cultured in serum-free DMEM and they were harvested after an additional 24 h period. Selected cultures were stimulated for 20 min prior to harvesting with EGF (40 ng/ml), TNF-α (40 ng/ml) or IL-1β (40 ng/ml) or were exposed to UV light (254 nm, 40J/m$^2$). To stably express Tpl-2 or Tpl-2K167M in NIH3T3 cells we used MSV-SRα-based retrovirus constructs (Landau, et al., 1992 Journal of Virology 66:5110–3). To inducibly express Tpl-2 or Tpl-2K167M, pUHD10.3-based constructs were stably transfected into NIH3T3.S26 cells expressing tTA (Gossen, et al., 1992, Proceedings of the National Academy of Sciences of the United States of America 89:5547–51) or REF52 cells expressing rtTA (Gossen, et al., 1995, Science 268:1766–9).

To demonstrate cell death and flow cytometry, NIH3T3, 293 or REF52 cells were seeded in 35 mm petri dishes at 0.75×$10^5$ cells per dish, and they were cultured for 48 h in complete media. Cells were then washed with phosphate buffered saline (PBS) and they were placed in media containing 0.5% or 10% serum in the presence or absence of murine or human TNF-α (50 ng/ml) for up to 48 h. Subsequently, they were trypsinized and harvested by centrifugation for 8 min at 600×g. The pelleted cells were washed with PBS, recentrifuged and resuspended in 1 ml PBS. The live-to-dead cell ratios were determined by trypan blue exclusion and light microscopy or by staining with 5 μg/ml propidium iodide (PI) and flow cytometry (Sherley, et al., 1988, Journal of Biological Chemistry 263:8350–8). A portion of the cells was incubated with ethidium bromide (75 μM) in FACS buffer [3.4 mM Na-citrate, 10 mM NaCl, 0.1%(v/v) Nonidet P-40], and their DNA content was determined also by flow cytometry. The data obtained by flow cytometry were analyzed using the Cell Quest software program (Beckton Dickinson).

For immunoprecipitation and in vitro kinase assays, cells were washed with ice-cold PBS and they were lysed on ice for 20 min in 0.5 ml of an NP-40 lysis buffer [20 mM Tris.Cl, pH 8.0, 137 mM NaCl, 0.5%(v/v) Nonidet P-40, 10% (v/v) glycerol, 10 mM NaF, 1 mM sodium orthovanadate, 1 mM phenylmethyl-sulfonyl fluoride, 2.5 nM okadaic acid (Sigma) 0.5 mM dithiothreitol, 1×complete protease inhibitors (Boehringer-Mannheim)]. The cell lysates were clarified by centrifugation at 12,000×g at 4° C. for 10 min. Subsequently, they were pre-cleared by incubation with 20 μl of a 50% suspension of protein A/protein G (1:1)-agarose (Gibco BRL) for 30 min at 4° C. Following removal of the agarose beads by centrifugation at 12,000×g at 4° C. for 10 min, the pre-cleared lysates were incubated for 3 h at 4° C. with the anti-Tpl-2 antibody PT492 (1/250 dilution), the anti-c-myc tag antibody 9E10.2 (1/250 dilution), the anti-HA antibody HA.11 (1/250 dilution) or the anti-TRADD antibody SC1164 (1/250 dilution) in the presence of 40 μl 50% protein A/protein G (1:1)-agarose. The immunoprecipitate/agarose-bead complexes were collected by centrifugation at 6,000×g for 2 min at 4° C., and they were washed, also at 4° C., three times with 1 ml lysis buffer. Immunoprecipitate/agarose-bead complexes used for carrying out in vitro kinase assays were further washed twice with 1 ml kinase wash buffer containing 20 mM HEPES, pH 7.5, 5 mM MgCl$_2$ and 1 mM dithiothreitol.

In vitro kinase assays were carried out as previously described (Sherley, et al., 1988, Journal of Biological Chemistry 263:8350–8). Briefly, pelleted immunoprecipitates were incubated with 10 μCi γ-$^{32}$P[ATP] (Amersham; 3000 Ci/mmol) for 20 min at room temperature in a volume of 20 μl and buffer conditions optimum for the corresponding protein kinase: Tpl-2 kinase assays were carried out in 20 mM HEPES, pH 7.5, 12.5 mM β-glycerophosphate, 10 mM MgCl$_2$, 5 mM MnCl$_2$, 0.5 mM Ethylene glycol-bis(β-aminoethyl ether)N,N,N',N'-tetraacetic acid (EGTA), 0.5 mM NaF, 1 mM dithiothreitol, 3 μM cold ATP, 1 μg aprotinin, and 1 μg leupeptin. JNK1 kinase assays were carried out in 12.5 mM HEPES, pH 7.5, 12.5 mM β-glycerophosphate, 7.5 mM MgCl$_2$, 0.5 mM Ethylene glycol-bis(β-aminoethyl ether)N,N,N',N'-tetraacetic acid (EGTA), 0.5 mM NaF, 0.5 mM sodium orthovanadate, 1 mM dithiothreitol, 20 μM cold ATP, 1 μg aprotinin and 1 μg leupeptin; the exogenous substrate was GST/N5-89Jun (2 μg/reaction). The kinase reaction was stopped by adding 7 μl 4×sample loading buffer (1 M urea, 62.5 mM Tris.HCl, pH 6.8, 100 mM dithiothreitol, 3% SDS, 10% glycerol, and 0.03% bromophenol blue). ERK1 activity was measured by an "in-gel" assay as described previously (Sherley, et al., 1988, Journal of Biological Chemistry 263:8350–8).

SDS-PAGE and electroblotting were carried out as previously described (Sherley, et al., 1988, Journal of Biological Chemistry 263:8350–8). The antibodies and the dilutions at which they were used were as follows: anti-Tpl-2 (PT492) (1/1000 dilution), anti-c-myc tag (9E10.2) (1/1500 dilution), anti-HA tag (HA.11) (1/1000 dilution), anti-IκB-β (KD21-5) (1/1000 dilution) and anti-IκB-P (SC945-G) (1/1000 dilution). Excess antibody was removed by two 10-min and three 5-min washes in PBS containing 0.1% (v/v) Tween-20. Antigen-bound antibody was detected by a 60-min room temperature incubation in a 1/5000–1/10000 dilution of the corresponding secondary antibody conjugated with horseradish peroxidase (Amersham). The unbound secondary antibody was removed using the same washing procedure we used to remove the excess primary antibody with three additional 10-min washes in PBS. The binding of the secondary antibody was detected by enhanced chemiluminescence (ECL, Amersham). Immunoblots were exposed to Reflection NEF film (NEN, DuPont) for 1–10 min.

To measure caspase activity, NIH3T3 cells stably infected with Tpl-2 wt.SRα, or Tpl-2K167M.SRα expression constructs, or vector only, were seeded in 60 mm petri dishes at ~10$^6$ cells per dish and cultured in complete media for 24 h. Following treatment with human TNF-α for 2, 8, 16 and 24 h the cells were scraped off the dish in 450 μl of a buffer containing 25 mM HEPES, pH 7.5,5 mM EDTA, 1 mM EGTA, 5 mM MgCl$_2$, 5 mM DTT, 10 μg/ml aprotinin (Sigma), 10 μg/ml leupeptin (Sigma), 10 μg/ml pepstatin (Sigma) and 1 mM phenylmethyl-sulfonyl fluoride. The harvested cells were rocked at 4° C. for 20 min and lysed by sonication for 30 sec at 4° C. The cell lysates were then clarified by centrifugation at 12,000×g at 4° C., quick-frozen in liquid nitrogen and stored at −70° C. After thawing, protein concentration was determined by the Bradford assay (BioRad). Cell lysates containing 50 μg of protein were incubated for 30 min at 37° C. with the fluorogenic substrate z-DEVD-AFC (15 μM), that mimics the cleavage site on PARP (Enzyme Systems & Products), in a buffer containing 25 mM HEPES, pH 7.5, 10% sucrose, 0.1% CHAPS and 10 mM dithiothreitol. Aspartase activity was determined by measuring fluorescent emission following cleavage of the fluorogenic substrate. The signal was measured using a Perkin Elmer LS 50 Luminescence spectrometer (excitation 400 nm, emission 505 nm).

For nuclear extracts and electrophoretic mobility shift assays (EMSA), NIH3T3 cells infected with the SRα vector or SRα-based expression constructs of Tpl-2 wt and Tpl-2K167M were seeded in 60 mm petri dishes at a density of ~0.75×10$^6$ cells per dish. The cells were stimulated with human TNF-α (40 ng/ml) and individual cultures were lysed at sequential time points (0, 5, 10, 15, and 60 min) following TNF-α treatment. The lysis buffer contained 10 mM HEPES, pH 7.9, 10 mM KCl, 0.2 mM EDTA and 0.5% NP-40. Cell nuclei were pelleted by centrifugation at 2000×g for 2 min at 4° C., and nuclear proteins were extracted using a buffer containing 20 mM HEPES, pH 7.9, 25% glycerol, 0.4 M NaCl, 0.2 mM EDTA, 0.5 mM DTT and 1× complete protease inhibitors (Boehringer-Mannheim). The supernatants representing the cytosolic fraction of the lysates were clarified by centrifugation at 12000×g for 10 min at 4° C., and they were subjected to SDS-PAGE and Western blotting. Protein concentration in the nuclear and cytoplasmic fractions was measured by the Bradford assay (BioRad). Electrophoretic mobility shift assays (EMSAs) were carried out by incubating the nuclear extracts with a γ-$^{32}$P[ATP]-end-labeled (56) NF-κB-specific double-stranded oligonucleotide derived from the HV LTR (ACAAGGGACTTTCCGCTGGGGACTTTCCAGGG) (SEQ ID NO:11). Incubation was carried out using 2.5 μg of protein and 10$^5$ cpm (~0.5 ng) of labeled oligonucleotides in 20 μl of binding buffer (4 mM Tris.HCl pH 7.5, 80 mM NaCl, 0.5 mM ZnSO$_4$, 5% glycerol, 1 mM DTT and 0.2 mg/ml polydeoxyinosinic-deoxycytidylic acid) at room temperature for 15 min. The DNA-protein complexes were separated from the unbound oligonucleotides in a 6% non-denaturing polyacrylamide gel. For transient transfections and chloramphenicol acetyl-transferase (CAT) assays, 10$^7$ EL4 cells were transiently transfected by electroporation with 6 μg of the NF-κB.CAT or the mutant mNF-κB.CAT reporter constructs together with 2.5 μg of a pCMV5 Tpl-2 wt construct or pCMV5. NF-κB.CAT contains the CAT gene under the control of a minimal TK promoter with one copy of the NF-κB binding site derived from the IL-2 promoter (TCGACAGAGGGGAATCTCCCAGAGGC) (SEQ ID NO:12) placed upstream. mNF-κB.CAT is an identical construct with a mutated NF-κB binding site (TCGACTCTGGGAAATGTCCCTGAGGC) (SEQ D NO:13) that fails to bind NF-κB. Both reporter constructs were provided by Dr. R. Bravo (Bristol-Myers Squibb). The electroporated DNA was supplemented with pBluescript to a total of 20 μg per transfection. Electroporations were carried out in quadruplicate at 260 mV/960 μF. At 44 h cells were harvested and CAT assays were performed (Sherley, et al., 1988, Journal of Biological Chemnistry 263:8350–8). Selected cultures were treated with 10 nM of phorbol 12-myristate 13-acetate (PMA) 8 h prior to harvesting. The acetyl-transferase reaction was carried out for 3 h. The acetylated and non-acetylated forms of [$^{14}$C]-chloramphenicol (Amersham) were separated on TLC plates (Sigma). Chloramphenicol acetylation was quantitated using a Fuji PhosphorImager and Fuji MacBas V2.2 software. Data are presented as the mean and standard deviation of the results of four transfections.

Figure 9:
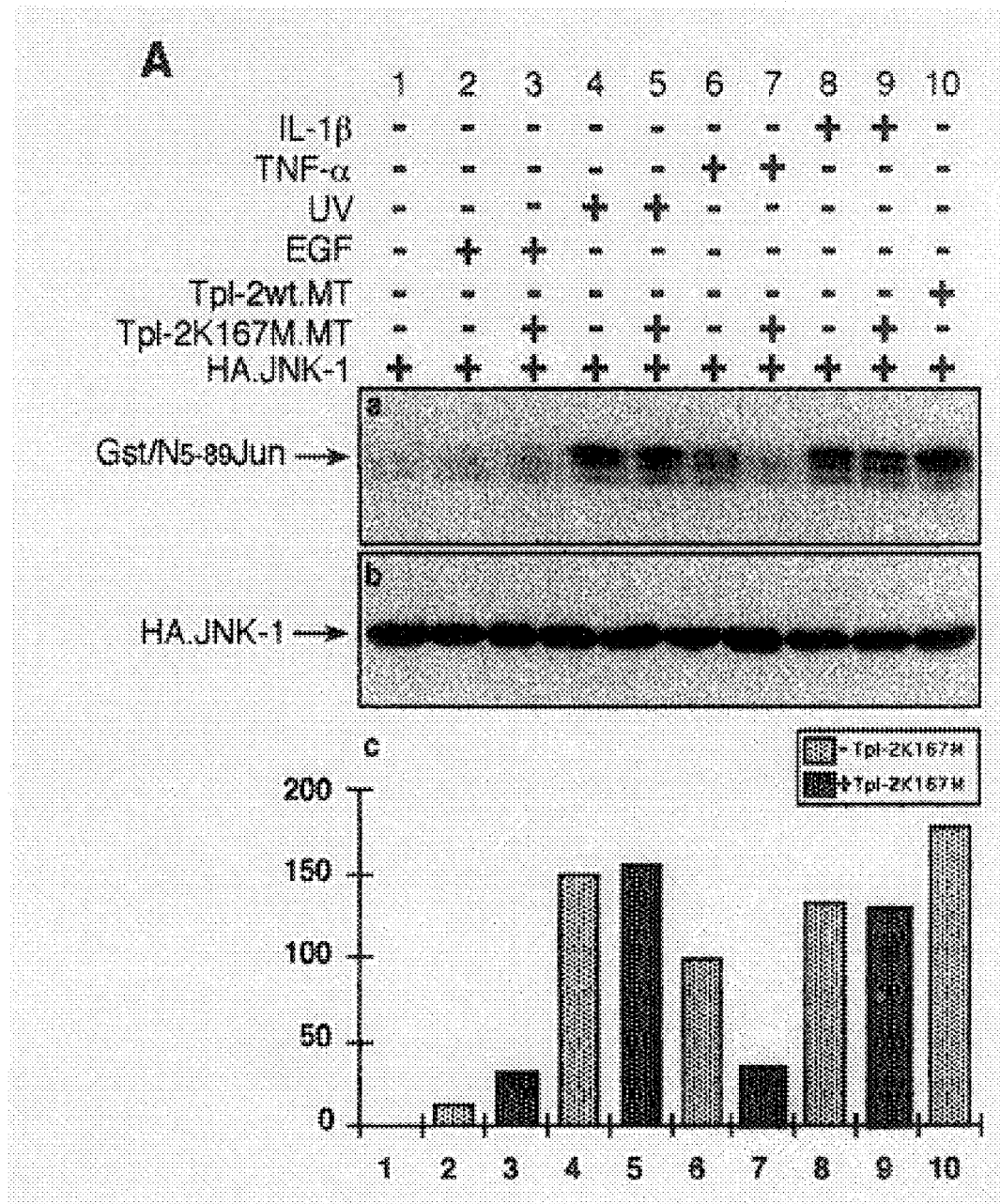
FIG. 9 shows results on in vitro kinase assays to demonstrate that Tpl2 tnasduces TNFα.signals.

As shown in FIG. 9 Tpl-2 transduced TNF-α signals. The kinase-dead mutant Tpl-2K167M inhibited TNF-α but not EGF, UV-irradiation or IL-1β-induced SAPK activation (A). In vitro lo kinase assay of HA•JNK1 immunoprecipitated from lysates of COS-1 cells transfected with HA•JNK1 alone or in combination with Tpl-2K167M or Tpl-2 wt(a). Transfected cells were lysed before (lanes 1 and 10) or after treatment with EGF (lanes 2 and 3), UV-irradiation (lanes 4 and 5), TNF-α (lanes 6 and 7) or IL-1β (lanes 8 and 9)(a). Western blot of the same immunoprecipitates, used in the kinase assay in a, probed with the anti-HA.11 monoclonal antibody (b). Relative HA•JNK1 kinase activity was determined by dividing the phosphoimager-measured $^{32}$P counts in the HA•JNK1 substrate GST/N5-89Jun by the densitometry-measured value of HA•JNK1 expression (c). The relative activation of JNK1 was corrected by subtracting the background JNK1 activity in lane 1. The in vitro kinase activity of HA•JNK1 induced by TNF-α (lane 6) was considered as 100%. This analysis was carried out using the Photoshop NIH-image software.

Figure 10:
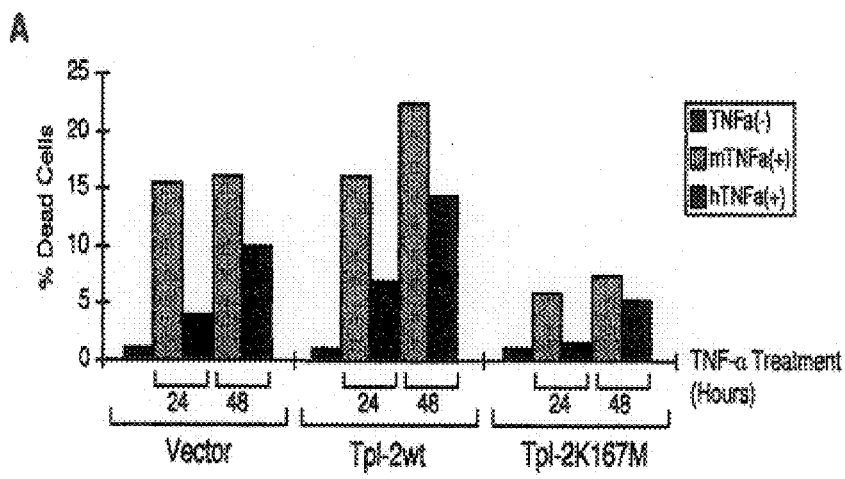
FIG. 10 shows that wild type Tpl2 potentiates and the kinase-dead Tpl2 inhibits a TNFα induced response in cells.
Figure 10:
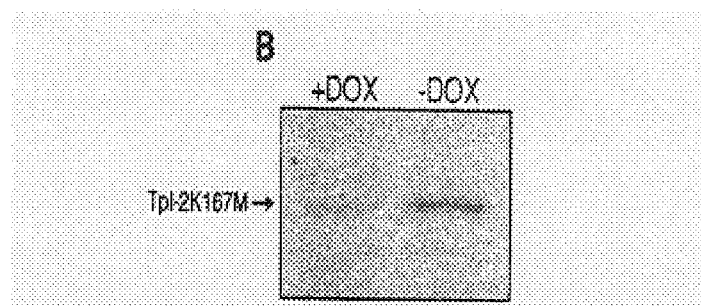
Figure 10:
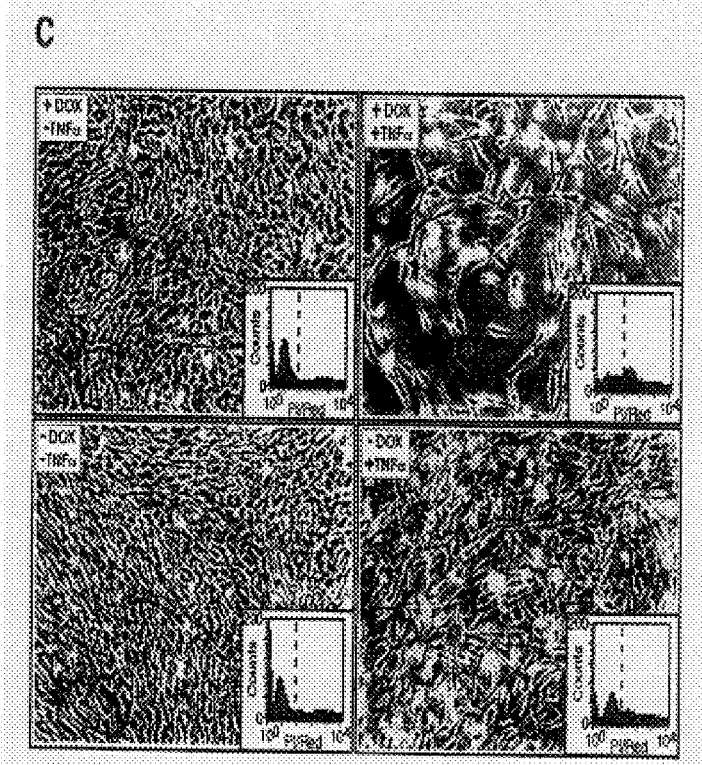

Wild-type Tpl-2 potentiated whereas the kinase-dead Tpl-2 inhibited TNF-α-induced apoptosis in NIH3T3 cells. See FIG. 10 NIH3T3 cells infected with SRα (Vector), Tpl-2 wt.SRα (Tpl-2 wt) or Tpl-2K167M.SRα (Tpl-2K167M) were treated with murine TNF-α (mTNF-α) or human TNF-α (hTNF-α) for 24 or 48 h. Cells were trypsinized and stained with PI. The ratio of live (non-staining) to dead (staining) cells was determined by flow cytometry (A). The results shown are representative of those obtained from three separate experiments with three independent cultures infected with each of the indicated retroviral constructs. Western blot of lysates of NIH3T3.S26 cells expressing Tpl-2K167M.HA from a tetracycline-tTA regulated promoter. Cells were cultured with or without doxycycline (DOX). The blot was probed with the anti-HA monoclonal antibody (B). The NIH3T3.S26 cells in C were cultured in the presence (upper panel) or absence (lower panel) of DOX for 24 h (C). Prior to photography, cells were cultured for an additional 36 h in the absence (left panel) or in the presence (right panel) of human TNF-α. The insets represent flow-cytometric profiles of these cells harvested following photography and stained with PI. The dotted line separates live (left) from dead (right) cells.

Figure 11:
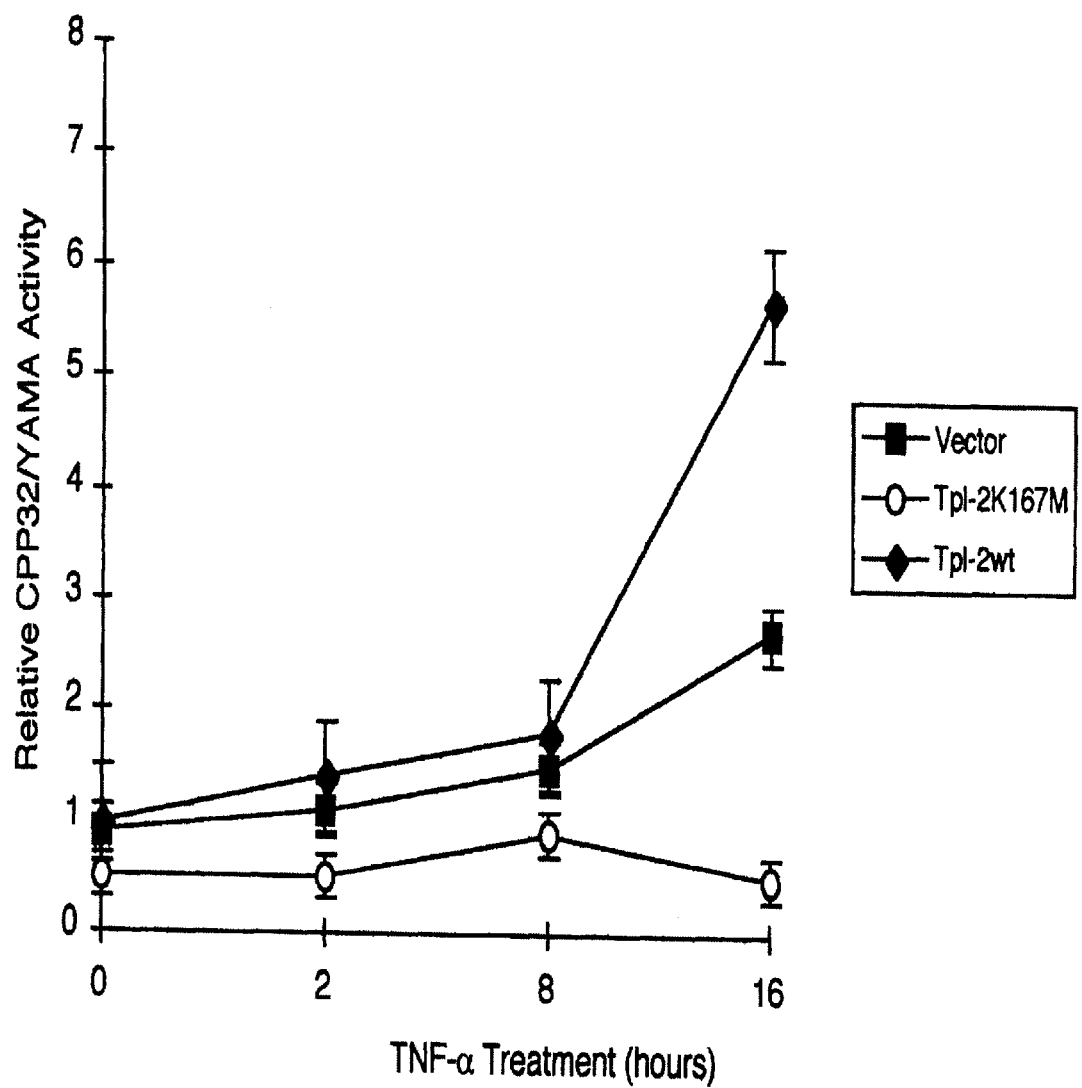
FIG. 11 shows that wild type Tpl2 enhances and the kinase-dead Tpl2 inhibits TNFα induced CPP32/YAMA activity.

Wild-type Tpl-2 enhanced whereas the kinase-dead Tpl-2 inhibited TNF-α-induced caspase-3 activation in NIH3T3 cells. See FIG. 11 Relative caspase-3 activity in lysates of NIH3T3 cells infected with SRα (Vector), Tpl-2K167M.SRα (Tpl-2K167M) or Tpl-2 wt.SRα (Tpl-2 wt) and treated with human TNF-α for the indicated lengths of time caspase-3 activity was determined by measuring the fluorescent signal emitted following cleavage of the fluorogenic tetrapeptide substrate z-DEVD-AFC. Assays were carried out in triplicate.

Figure 12:
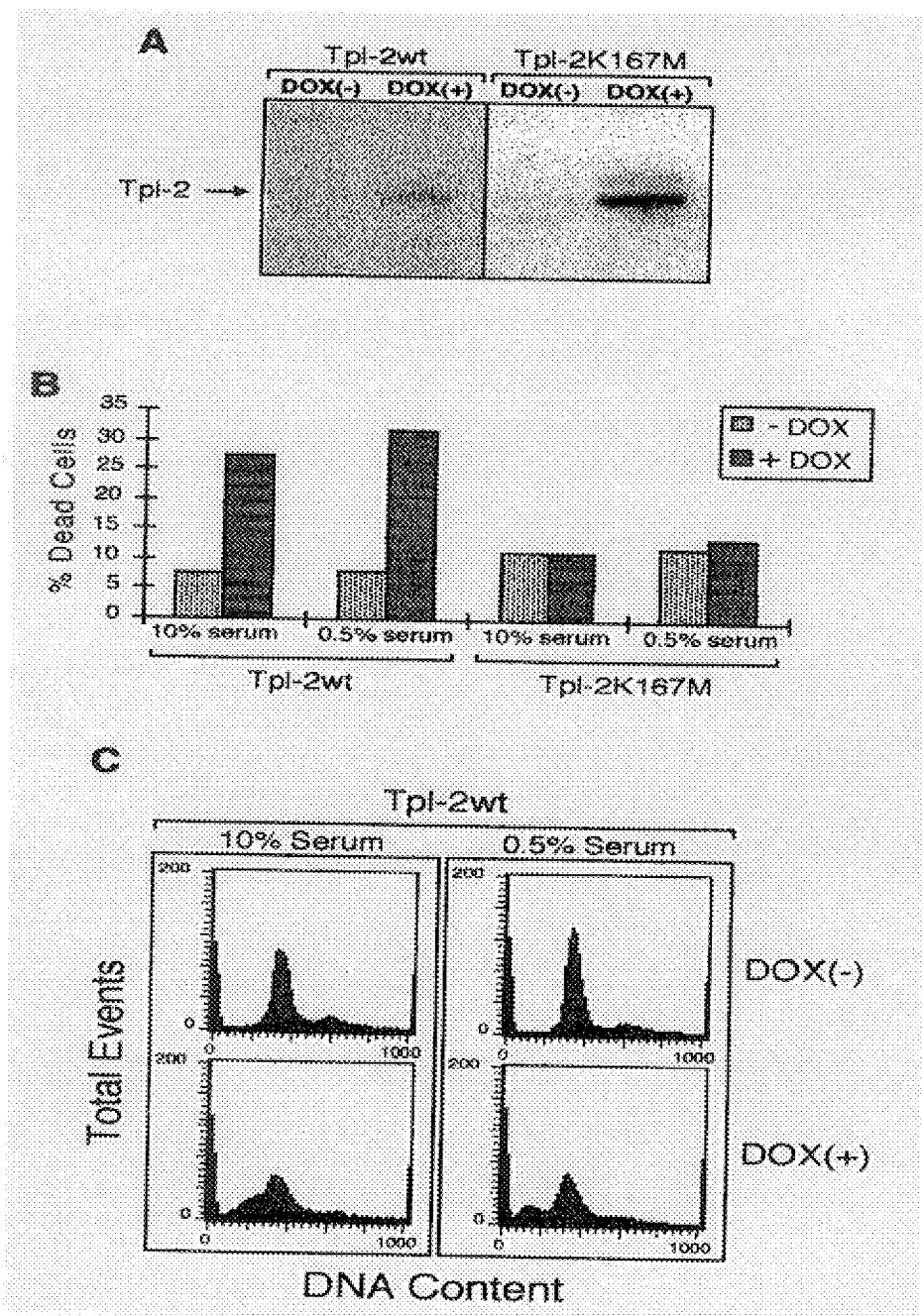
FIG. 12 shows results on the inducible expression of Tpl2 in REF52.

REF52 cells expressing wild-type Tpl-2 from a tetracycline inducible promoter did undergo apoptosis following Tpl-2 induction. See FIG. 12 shown in FIG. 12A are Western blots of lysates of REF52 cells expressing Tpl-2 wt.HA or Tpl-2K167M.HA from a tetracycline-rtTA regulated promoter. Cells were cultured with or without DOX. Blots were probed with the anti-HA.11 monoclonal antibody. Percentage of dead cells in REF52 cells inducibly expressing Tpl-2 wt or Tpl-2K167M. REF52 cells expressing (DOX+) or not expressing (DOX−) Tpl-2 wt.HA or Tpl-2K167M.HA (panel A) were cultured in media containing normal (10%) or low (0.5%) serum for 48 h prior to harvesting (FIG. 12B) Cells were stained with ethidium bromide and analyzed by flow cytometry. Cell cycle distribution of the cells in B inducibly expressing Tpl-2 wt. The emergence of a subgenomic DNA peak indicates cell death by apoptosis (C).

Figure 13:
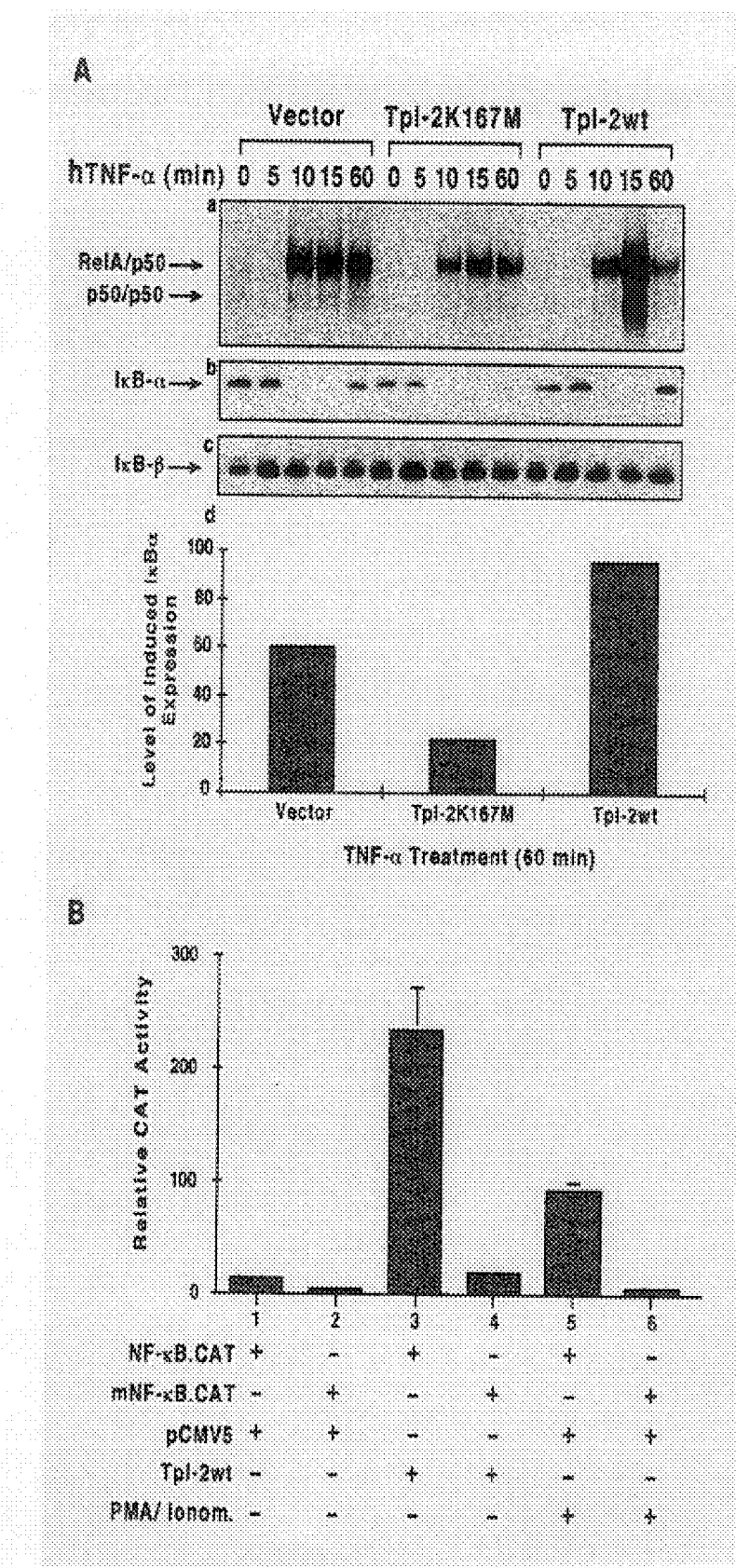
FIG. 13 shows that wild type Tpl2 enhances and the kinase-dead Tpl2 inhibits TNFα induced NF-κB activation in NIH3T3 cells.

Wild-type Tpl-2 enhanced whereas the kinase-dead Tpl-2 inhibited TNF-α-induced NF-κB activation in NIH3T3 cells. See FIG. 13. EMSA of a $^{32}$P-labeled double-stranded NF-κB specific oligonucleotide probe derived from the HIV LTR following its incubation with nuclear extracts from NIH3T3 cells treated with human TNF-α for the indicated lengths of time (a). The cells were infected with SRα (Vector), Tpl-2K167M.SRα (Tpl-2K167M) or Tpl-2 wt.SRα (Tpl-2 wt) retrovirus constructs. Western blots of cytosolic extracts of the same cells shown in a, probed with anti-IκB-α (b) and anti-IκB-P (c) polyclonal antibodies (b and c). IκB-α protein levels at 60 min following TNF-α treatment (d). The relative expression of IκB-α at this time point was determined by NIH image-assisted densitometry of the corresponding bands in b. Activation of NF-κB by overexpressed Tpl-2 in EL4 cells. EL4 cells were transiently co-transfected in quadruplicate with NF-κB.CAT or mNF-κB.CAT reporter constructs and pCMV5 or a pCMV5-based expression construct of Tpl-2 wt as indicated. Control cells, co-transfected with the vector and the reporter constructs were treated with PMA plus ionomycin. The results show the CAT activity in lysates of the transfected cells 44 h later (e).

Figure 14:
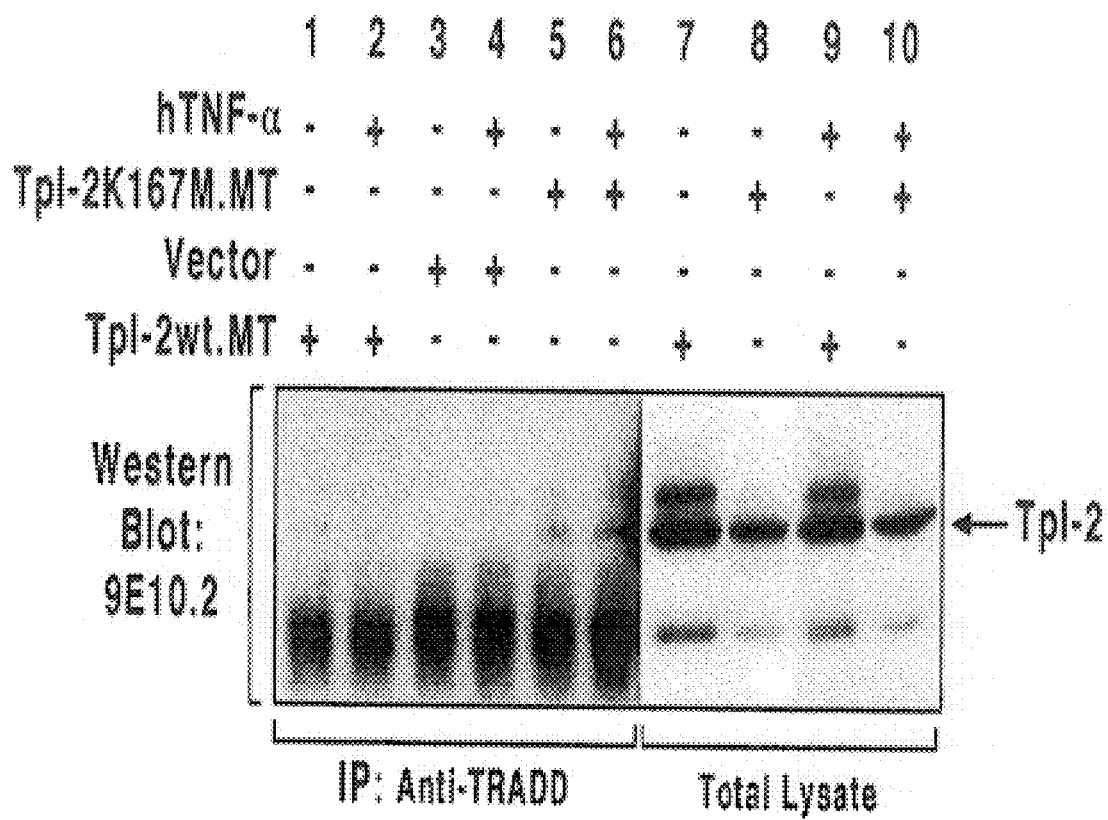
FIG. 14 shows that Tpl2 interacts with TRADD and TRAF2 in 293 cells.

Tpl-2 interacted with TRADD in 293 cells. See FIG. 14 Tpl-2 activation by TNF-α abrogated the interaction. Western blots of anti-TRADD (lanes 1–6) immunoprecipitates of lysates of 293 cells transiently transfected with a Tpl-2 wt.MT pCMV5 expression construct (lanes 1 and 2), pCMV5 (lanes 3 and 4) or a Tpl-2K167M.MT pCMV5 construct (lanes 5 and 6) were probed with the anti-c-myc tag monoclonal antibody 9E10.2. The indicated cultures were treated with human (h) TNF-α (lanes 2, 4 and 6) prior to lysis and immunoprecipitation. To determine the expression of Tpl-2 wt.MT and Tpl-2K167M.MT, total cell lysates derived from the same cells were analyzed by Western blotting using the anti-c-myc tag antibody (lanes 7–10).

All publications and references, including but not limited to patent applications, cited in this specification, are herein incorporated by reference in their entirety as if each individual publication or reference were specifically and individually indicated to be incorporated by reference herein as being fully set forth. While this invention has been described with a reference to specific embodiments, it will be obvious to those of ordinary skill in the art that variations in these methods and compositions may be used and that it is intended that the invention may be practiced otherwise than as specifically described herein. Accordingly, this invention includes all modifications encompassed within the spirit and scope of the invention as defined by the claims.

What is claimed is:

1. A transgenic mouse whose genome comprises a homozygous inactivated Tpl2 gene, wherein said inactivation is by the insertion of an exogenous sequence into said gene or by replacement of part of the endogenous Tpl2 gene with an exogenous sequence and wherein said mouse does not produce functional Tpl2 and exhibits a phenotype of resistance to LPS induced endotoxin shock or TNFα-mediated inflammatory disease.

2. The transgenic mouse of claim 1, wherein said mouse exhibits a phenotype of resistance to LPS induced endotoxin shock.

3. The transgenic mouse of claim 1, wherein said mouse exhibits a phenotype of resistance to TNFα-mediated inflammation.

4. Spleen cells or macrophages isolated from the transgenic mouse of claim 1.

5. A transgenic mouse whose genome comprises a homozygous disruption of the endogenous Tpl-2 gene, wherein said mouse does not produce functional Tpl2 and exhibits a phenotype of resistance to LPS induced endotoxin shock or TNFα-mediated inflammatory disease.

6. The transgenic mouse of claim 5, wherein said mouse exhibits a phenotype of resistance to LPS induced endotoxin shock or TNFα-mediated inflammatory disease.

7. The transgenic mouse of claim 5, wherein said mouse exhibits a phenotype of resistance to TNFα-mediated inflammatory disease.

8. Spleen cells or macrophages isolated from the transgenic mouse of claim 5.

* * * * *

UNITED STATES PATENT AND TRADEMARK OFFICE
CERTIFICATE OF CORRECTION

PATENT NO. : 6,660,906 B1
DATED : February 25, 2004
INVENTOR(S) : Tsichlis

It is certified that error appears in the above-identified patent and that said Letters Patent is hereby corrected as shown below:

Drawings,
Sheet 3, Figure 3, please replace Figure 3 with Figure 3 shown below

Figure 3

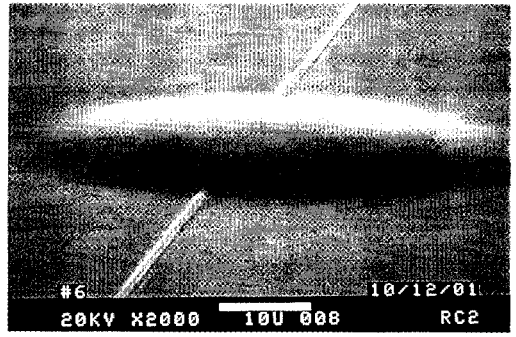

Signed and Sealed this

Twenty-fourth Day of August, 2004

JON W. DUDAS
*Director of the United States Patent and Trademark Office*